(12) United States Patent
Dekhtyar et al.

(10) Patent No.: US 9,447,051 B2
(45) Date of Patent: Sep. 20, 2016

(54) DIAMINOPYRIMIDINES AND USES THEREOF

(71) Applicant: AbbVie inc., North Chicago, IL (US)

(72) Inventors: Tatyana Dekhtyar, Libertyville, IL (US); Arthur Gomtsyan, Vernon Hills, IL (US); M-Akhteruzzaman Molla, Gurnee, IL (US); Anil Vasudevan, Union Grove, WI (US); Iok Chan Ng, Arlington Heights, IL (US); Mikhail Chafeev, Abbott Park, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/379,155

(22) PCT Filed: Feb. 15, 2013

(86) PCT No.: PCT/US2013/026446
§ 371 (c)(1),
(2) Date: Aug. 15, 2014

(87) PCT Pub. No.: WO2013/123401
PCT Pub. Date: Aug. 22, 2013

(65) Prior Publication Data
US 2015/0025095 A1 Jan. 22, 2015

Related U.S. Application Data

(60) Provisional application No. 61/600,374, filed on Feb. 17, 2012.

(51) Int. Cl.
| | | |
|---|---|---|
| *C07D 239/32* | (2006.01) |
| *A61K 31/505* | (2006.01) |
| *C07D 239/48* | (2006.01) |
| *C07D 403/12* | (2006.01) |
| *C07D 401/14* | (2006.01) |
| *C07D 405/14* | (2006.01) |
| *C07D 401/12* | (2006.01) |
| *C07D 409/14* | (2006.01) |
| *C07D 413/12* | (2006.01) |
| *C07D 417/14* | (2006.01) |
| *A61K 45/06* | (2006.01) |
| *A61K 31/506* | (2006.01) |
| *C07D 413/14* | (2006.01) |

(52) U.S. Cl.
CPC .......... *C07D 239/48* (2013.01); *A61K 31/505* (2013.01); *A61K 31/506* (2013.01); *A61K 45/06* (2013.01); *C07D 239/32* (2013.01); *C07D 401/12* (2013.01); *C07D 401/14* (2013.01); *C07D 403/12* (2013.01); *C07D 405/14* (2013.01); *C07D 409/14* (2013.01); *C07D 413/12* (2013.01); *C07D 413/14* (2013.01); *C07D 417/14* (2013.01)

(58) Field of Classification Search
CPC C07D 239/32; C07D 239/48; C07D 401/12; A61K 31/505; A61K 31/506
USPC .................. 544/317, 323, 324; 514/274, 275
See application file for complete search history.

(56) References Cited

U.S. PATENT DOCUMENTS

| | | |
|---|---|---|
| 2003/0225073 A1 | 12/2003 | Bebbington et al. |
| 2004/0002496 A1 | 1/2004 | Bebbington et al. |
| 2004/0009974 A1 | 1/2004 | Bebbington et al. |
| 2004/0009981 A1 | 1/2004 | Bebbington et al. |

FOREIGN PATENT DOCUMENTS

| | | | |
|---|---|---|---|
| GB | 810846 A | | 3/1959 |
| WO | WO 03/055489 | * | 7/2003 |
| WO | WO-2005058869 A1 | | 6/2005 |
| WO | WO 2006/124874 | * | 11/2006 |
| WO | WO 2009/007753 | * | 1/2009 |

OTHER PUBLICATIONS

Martyn et al., Synthesis and antiplasmodial activity of novel 2,4-diaminopyrimidines, Bioorganic & Medicinal Chemistry Letters, vol. 20, No. 1, pp. 228-231, 2010.*
Turner et al., Respiratory syncytial virus: current and emerging treatment options, ClinicoEconomics and Outcomes Research, pp. 217-225 (2014).*
Bawage et al., Recent Advances in Diagnosis, Prevention, and Treatment of Human Respiratory Syncitial Virus, Advances in Virology, pp. 1-26, 2013.*
Allen L.V., et al., Ansel's Pharmaceutical Dosage forms and Drug Delivery Systems, Troy D.B., et al., eds., 8th Edition, Lippincott Williams & Wilkins, 2005.
Greene T.W., et al., Protective Groups in Organic Synthesis, 3rd Edition, John Wiley and Sons, Inc., 1999.
Hoover J.E., Remington's Pharmaceutical Sciences, 15th Edition, 1975, Mack Publishing Co.
International Search Report for Application No. PCT/US2013/026446, mailed on Apr. 4, 2013, 5 pages.
Nikitenko A., et al., "Pyrimidine Containing Rsv Fusion Inhibitors." Bioorganic & Medicinal Chemistry Letters, 2005, vol. 15 (2), pp. 427-430.

* cited by examiner

*Primary Examiner* — Deepak Rao
(74) *Attorney, Agent, or Firm* — Laura E. Johannes

(57) ABSTRACT

This disclosure relates to: (a) compounds and salts thereof that, inter alia, inhibit RSV infection and/or replication; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

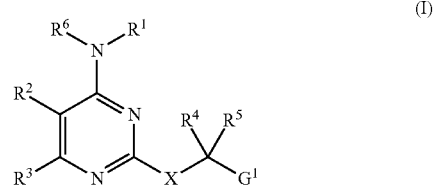

8 Claims, No Drawings

DIAMINOPYRIMIDINES AND USES THEREOF

TECHNICAL FIELD

This disclosure is directed to: (a) compounds and salts thereof that, inter alia, are useful for inhibiting human respiratory syncytial virus (RSV) infection and/or replication; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

BACKGROUND

Human respiratory syncytial virus (RSV) is a pneumovirus in the Paramyxoviridae family. It is an enveloped, nonsegmented, negative-stranded RNA virus. Its 15.2 kb genome has been completely sequenced and it contains 10 mRNAs encoding 11 distinct proteins. RSV has three transmembrane surface proteins (F, G, SH) essential for attachment and entry, two nonstructural proteins (NS1, NS2), a matrix (M) protein, a nucleocapsid (N) protein that encapsidates the viral RNA genome, a phosphoprotein (P), and an RNA polymerase (L). In addition, the RSV M2 mRNA encodes both the M2-1 and M2-2 proteins.

RSV is the leading cause of serious lower respiratory tract infection in infants and young children. Most infected infants and children suffer only mild symptoms, but 25-40% of them develop lower respiratory signs indicative of a viral bronchiolitis or pneumonia. Severe lower respiratory tract RSV infection can lead to consequences of different severity, ranging from increased risk of developing childhood asthma to death. Following RSV infection, immunity is incomplete and re-infections can occur throughout life. It is estimated that RSV causes approximately 60 million infections and 160,000 deaths worldwide each year. RSV infection results in up to 125,000 hospitalizations of infants annually in the United States, which is equivalent to approximately 0.1-0.2% of hospital admission of infants from this age group. The infants most at risk of severe RSV disease are those born prematurely, and those with bronchopulmonary dysplasia, congenital heart disease, or immunodeficiency. Hospital admission rates with these conditions range between 5% and 30%. The mortality rate among children admitted to hospital is approximately 3% for those with heart and lung diseases and up to 1% for those without these risk factors. RSV infection is also a significant cause of morbidity in the elderly and immunocompromised populations. In the hospitalized elderly, mortality can be as high as 10-20%, and in the severely immunocompromised patients with RSV pneumonia, the rate is approximately 50%.

RSV epidemics occur every winter in temperate climates. There are two groups (also referred to as subgroups) of RSV, A and B. Both groups A and B may co-circulate within an epidemic, but their relative proportion may vary from year to year. The predominant epidemic group may also change in different years, with group A having a somewhat higher incidence of being the predominant group. The sequence homology between the two groups varies in the different viral proteins. For example, the F and N proteins are highly conserved with 91% and 96% amino acid identity between the two groups, respectively. The sequence of the G protein, on the other hand, is significantly different between the two groups, with the amino acid identity being only 53%. There is conflicting data regarding the virulence differences between the two groups of RSV. Some studies found no difference in the clinical severity of the illness caused by the two groups, while others reported that group A appeared to be associated with more severe disease.

At present, there is no clinically approved vaccine or effective antiviral therapy for the treatment of RSV. Attempts to develop a safe and efficacious RSV vaccine have not been successful thus far partly due to challenges associated with the treatment of at-risk subjects (including infants, the elderly and the immunocompromised) who usually have low tolerance to the side effects of a vaccine and who tend to mount reduced immune responses due to their immature or weaker immune systems.

Ribavirin has been used to treat RSV infection but requires a prolonged aerosol administration, and there are doubts as to its safety and its efficacy in the treatment of RSV infection. In addition, ribavirin is associated with undesirable side effects such as anemia, fatigue, irritability, skin rash, nasal stuffiness, sinusitis, cough and even birth defects.

Palivizumab/Synagis® is a humanized murine monoclonal antibody directed against the RSV F protein that has been used as passive immunoprophylaxis to prevent the spread of the virus to the lower respiratory tract. Although palivizumab has been used successfully to reduce the frequency of hospitalizations for RSV infection in high risk populations, the antibody has only been approved for prophylactic use in infants who are at risk of developing serious symptoms from RSV infection, such as those born prematurely, and/or with congenital heart or lung disease.

Therefore, there is a significant need for compounds for the prevention and treatment of RSV infection and for therapies that extend safe and effective treatment to at-risk adults and children with acute RSV infections.

SUMMARY

Disclosed herein are compounds of formula (I), and methods of making such compounds,

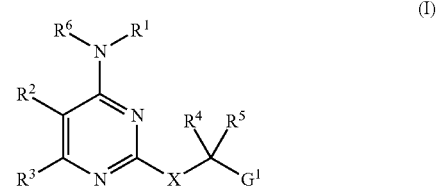

(I)

wherein:

$R^1$ is $C_1$-$C_6$-alkyl, $C_1$-$C_6$-haloalkyl, $C_3$-$C_8$-cycloalkyl, $C_3$-$C_8$-cycloalkyl-$C_1$-$C_6$-alkyl, phenyl, bicyclic aryl, phenyl-$C_1$-$C_6$-alkyl, heterocyclyl, heterocyclyl-$C_1$-$C_6$-alkyl, mono cyclic heteroaryl, or monocyclic heteroaryl-$C_1$-$C_6$-alkyl; wherein the $C_3$-$C_8$-cycloalkyl, the $C_3$-$C_8$-cycloalkyl of $C_3$-$C_8$-cycloalkyl-$C_1$-$C_6$-alkyl, heterocyclyl, and heterocyclyl of heterocyclyl-$C_1$-$C_6$-alkyl are optionally substituted with 1, 2, 3, or 4 substituents selected from the group consisting of $C_1$-$C_{10}$-alkyl, $C_2$-$C_{10}$-alkenyl, $C_2$-$C_{10}$-alkynyl, $C_1$-$C_{10}$-haloalkyl, $C_2$-$C_{10}$-haloalkenyl, $C_2$-$C_{10}$-haloalkynyl, halogen, oxo, cyano, hydroxy, —O—$C_1$-$C_6$-alkyl, —O—$C_1$-$C_6$-haloalkyl, —$C_1$-$C_3$-alkylene-O—H, —$C_1$-$C_3$-alkylene-O—$C_1$-$C_6$-alkyl, —$C_1$-$C_3$-alkylene-O—$C_1$-$C_6$-haloalkyl, —$C_1$-$C_3$-alkylene-NH$_2$, —NH$_2$, —C(O)O—$C_1$-$C_6$-alkyl, —N($R^{b1}$)C(O)$R^{b1}$, —CON($R^{a1}$)($R^{b1}$), —C(O)$R^{b1}$, —OC(O)R$^{b1}$, —OS(O)$_2$N(R$^{a1}$)(R$^{b1}$), —CO$_2$H, —CO$_2$R$^{b1}$, —N(R$^{b1}$)C(O)N(R$^{b1}$)$_2$, —S—R$^{b1}$, —S(O)$_2$R$^{b1}$, —S(O)R$^{b1}$, —SO$_2$N(R$^{a1}$)(R$^{b1}$), —N(R$^{a1}$)(R$^{b1}$), —N(R$^{b1}$)S(O)$_2$R$^{b1}$, —N(R$^{b1}$)C(O)O(R$^{b1}$), —N(R$^{b1}$)S(O)$_2$O(R$^{b1}$), -L$^{1a}$-O—R$^{b1}$, -L$^{1a}$-CN, -L$^{1a}$-N(R$^{b1}$)C(O)R$^{b1}$, -L$^{1a}$-CON(R$^{a1}$)(R$^{b1}$), -L$^{1a}$-C(O)R$^{b1}$, -L$^{1a}$-OC(O)R$^{b1}$, -L$^{1a}$-CO$_2$H, -L$^{1a}$-CO$_2$R$^{b1}$, -L$^{1a}$-N(R$^{b1}$)C(O)N(R$^{b1}$)$_2$, -L$^{1a}$-S—R$^{b1}$, -L$^{1a}$-S(O)$_2$R$^{b1}$, -L$^{1a}$-S(O)R$^{b1}$, -L$^{1a}$-SO$_2$N(R$^{a1}$)(R$^{b1}$), -L$^{1a}$-N(R$^{a1}$)(R$^{b1}$), -L$^{1a}$-N(R$^{b1}$)S(O)$_2$R$^{b1}$, and -L$^{1a}$-N(R$^{b1}$)C(O)O(R$^{b1}$);
wherein the phenyl, the bicyclic aryl, the phenyl of phenyl-C$_1$-C$_6$-alkyl, the monocyclic heteroaryl and monocyclic heteroaryl of monocyclic heteroaryl-C$_1$-C$_6$-alkyl are optionally substituted with 1, 2, 3, 4, or 5 substituents selected from the group consisting of halogen, C$_1$-C$_6$-alkyl, C$_1$-C$_6$-haloalkyl, —OCH$_2$O—, —O—R$^b$, —CN, —N(R$^b$)C(O)R$^b$, —CON(R$^a$)(R$^b$), —C(O)R$^b$, —OC(O)R$^b$, —OS(O)$_2$N(R$^a$)(R$^b$), —CO$_2$H, —CO$_2$R$^b$, —N(R$^b$)C(O)N(R$^b$)$_2$, —S—R$^b$, —S(O)$_2$R$^b$, —S(O)R$^b$, —SO$_2$N(R$^a$)(R$^b$), —N(R$^a$)(R$^b$), —N(R$^b$)S(O)$_2$R$^b$, —N(R$^b$)C(O)O(R$^b$), —N(R$^b$)S(O)$_2$O(R$^b$), -L$^1$-O—R$^b$, -L$^1$-CN, -L$^1$-N(R$^b$)C(O)R$^b$, -L$^1$-CON(R$^a$)(R$^b$), -L$^1$-C(O)R$^b$, -L$^1$-OC(O)R$^b$, -L$^1$-CO$_2$H, -L$^1$-CO$_2$R$^b$, -L$^1$-N(R$^b$)C(O)N(R$^b$)$_2$, -L$^1$-S—R$^b$, -L$^1$-S(O)$_2$R$^b$, -L$^1$-S(O)R$^b$, -L$^1$-SO$_2$N(R$^a$)(R$^b$), -L$^1$-N(R$^a$)(R$^b$), -L$^1$-N(R$^b$)S(O)$_2$R$^b$, and -L$^1$-N(R$^b$)C(O)O(R$^b$);

$R^2$ is methyl or ethyl;

$R^3$ is methyl or ethyl;

$R^4$ and $R^5$ are independently selected from the group consisting of hydrogen, C$_1$-C$_6$-alkyl, and C$_1$-C$_6$-haloalkyl;

$R^6$ is selected from the group consisting of hydrogen, C$_1$-C$_6$-alkyl, and C$_1$-C$_6$-haloalkyl;

$G^1$ is phenyl or monocyclic heteroaryl, wherein the phenyl or monocyclic heteroaryl are optionally substituted with 1, 2, 3, 4, or 5 substituents selected from the group consisting of halogen, C$_1$-C$_6$-alkyl, C$_1$-C$_6$-haloalkyl, —O—R$^f$, —CN, —N(R$^f$)C(O)R$^f$, —CON(R$^e$)(R$^f$), —C(O)R$^f$, —OC(O)R$^f$, —CO$_2$H, —CO$_2$R$^f$, —N(R$^f$)C(O)N(R$^f$)$_2$, —S—R$^f$, —S(O)$_2$R$^f$, —S(O)R$^f$, —SO$_2$N(R$^e$)(R$^f$), —N(R$^e$)(R$^f$), —N(R$^f$)S(O)$_2$R$^f$, —N(R$^f$)C(O)O(R$^f$), -L$^3$-O—R$^f$, -L$^3$-CN, -L$^3$-N(R$^f$)C(O)R$^f$, -L$^3$-CON(R$^e$)(R$^f$), -L$^3$-C(O)R$^f$, -L$^3$-OC(O)R$^f$, -L$^3$-CO$_2$H, -L$^3$-CO$_2$R$^f$, -L$^3$-N(R$^f$)C(O)N(R$^f$)$_2$, -L$^3$-S—R$^f$, -L$^3$-S(O)$_2$R$^f$, -L$^3$-S(O)R$^f$, -L$^3$-SO$_2$N(R$^e$)(R$^f$), -L$^3$-N(R$^e$)(R$^f$), -L$^3$-N(R$^f$)S(O)$_2$R$^f$, and -L$^3$-N(R$^f$)C(O)O(R$^f$);

X is selected from O, S, NR$^g$, or C(R$^h$R$^i$);

$R^a$, at each occurrence, is each independently hydrogen, C$_1$-C$_6$-alkyl, C$_1$-C$_6$-haloalkyl, or C$_3$-C$_8$-cycloalkyl, wherein the C$_3$-C$_8$-cycloalkyl is optionally substituted with 1, 2, 3, or 4 substituents selected from the group consisting of halogen, oxo, C$_1$-C$_3$alkyl, and C$_1$-C$_3$-haloalkyl;

$R^{a1}$, at each occurrence, is each independently hydrogen, C$_1$-C$_6$-alkyl, C$_1$-C$_6$-haloalkyl, or C$_3$-C$_8$-cycloalkyl, wherein the C$_3$-C$_8$-cycloalkyl is optionally substituted with 1, 2, 3, or 4 substituents selected from the group consisting of halogen, oxo, C$_1$-C$_3$alkyl, and C$_1$-C$_3$-haloalkyl;

$R^b$ is each independently hydrogen, C$_1$-C$_6$-alkyl, or C$_1$-C$_6$-haloalkyl;

$R^{b1}$ is each independently hydrogen, C$_1$-C$_6$-alkyl, or C$_1$-C$_6$-haloalkyl;

$R^e$, at each occurrence, is each independently hydrogen, C$_1$-C$_6$-alkyl, C$_1$-C$_6$-haloalkyl, or C$_3$-C$_8$-cycloalkyl, wherein the C$_3$-C$_8$-cycloalkyl is optionally substituted with 1, 2, 3, or 4 substituents selected from the group consisting of halogen, oxo, C$_1$-C$_3$alkyl, and C$_1$-C$_3$-haloalkyl;

$R^f$ is each independently hydrogen, C$_1$-C$_6$-alkyl, or C$_1$-C$_6$-haloalkyl;

$R^g$ is hydrogen or C$_1$-C$_6$-alkyl.

$R^h$ and $R^i$ are independently hydrogen, C$_1$-C$_6$-alkyl, or C$_1$-C$_6$-haloalkyl;

$L^1$, at each occurrence, is each independently C$_1$-C$_6$-alkylene or C$_3$-C$_8$-cycloalkyl, wherein L$^1$ is each optionally substituted with 1, 2, 3, or 4 halogen or 1 or 2 hydroxy;

$L^{1a}$, at each occurrence, is each independently C$_1$-C$_6$-alkylene or C$_3$-C$_8$-cycloalkyl, wherein L$^{1a}$ is each optionally substituted with 1, 2, 3, or 4 halogen or 1 or 2 hydroxy; and $L^3$, at each occurrence, is each independently C$_1$-C$_6$-alkylene or C$_3$-C$_8$-cycloalkyl, wherein L$^3$ is each optionally substituted with 1, 2, 3, or 4 halogen.

This disclosure also relates to pharmaceutical compositions comprising therapeutically effective amount of one or more compound(s) described herein or pharmaceutically acceptable salts, solvates, or salts of solvates thereof, in combination with one or more pharmaceutically acceptable carrier(s).

This disclosure also is directed to compositions (including pharmaceutical compositions) that comprise one or more of the disclosed compounds and/or salts, and, optionally, one or more additional therapeutic agents.

This disclosure also is directed to kits that comprise one or more of the disclosed compounds and/or salts, and, optionally, one or more additional therapeutic agents.

This disclosure also is directed to methods of use of the compounds, salts, compositions, and/or kits to, for example, inhibit replication of an RNA virus (including RSV).

This disclosure also is directed to a use of one or more of the disclosed compounds and/or salts to prepare a medicament. The medicament optionally can comprise one or more additional therapeutic agents. In some embodiments, the medicament is useful for treating RSV infection.

The compounds, compositions comprising the compounds, pharmaceutically acceptable salts, solvates, or salts of the solvates thereof, and methods for treating or preventing conditions and disorders by administering the compounds or compositions thereof, are further described herein. These and other objectives are described further in the following paragraphs. These objectives should not be deemed to narrow the scope of the disclosure.

DETAILED DESCRIPTION

This detailed description is intended only to acquaint others skilled in the art with the disclosed embodiments, their principles, and their practical application so that others skilled in the art may adapt and apply the embodiments in their numerous forms, as they may be best suited to the requirements of particular uses. This description and its specific examples are intended for purposes of illustration only. This disclosure, therefore, is not limited to the embodiments described in this patent application, and may be variously modified.

The present disclosure describes compounds of formula (I) and methods of preparing such compounds,

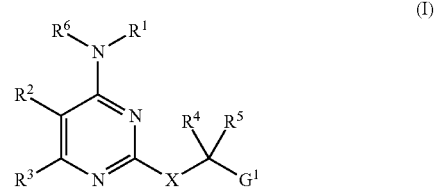

(I)

wherein $R^1$, $R^2$, $R^3$, $R^4$, $R^5$, $R^6$, $G^1$ and X are as defined herein. Compositions comprising such compounds and methods for treating conditions and disorders using such compounds and compositions are also disclosed.

In various embodiments, compounds described herein may contain variables that occur more than one time in any substituent or in the compound described or any other formulae herein. Definition of a variable on each occurrence is independent of its definition at another occurrence. Further, combinations of variables are permissible only if such combinations result in stable compounds. Stable compounds are compounds that can be isolated from a reaction mixture.

DEFINITIONS

The term "alkenyl", means a straight or branched hydrocarbon chain containing at least one carbon-carbon double bond. The term "$C_2$-$C_{10}$-alkenyl" means an alkenyl group containing 2-10 carbon atoms. Non-limiting examples of alkenyl include buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon and contains at least one carbon-carbon double. "$C_2$-$C_6$-alkenylene" means an alkenylene group containing 2-6 carbon atoms. Representative examples of alkenylene include, but are not limited to, —C(=CH$_2$)—, —CH=CH— and —CH$_2$CH=CH—.

The term "alkyl" as used herein, means a straight or branched, saturated hydrocarbon chain. For example "$C_1$-$C_{10}$-alkyl" means a straight or branched chain, saturated hydrocarbon containing 1 to 10 carbon atoms. For example "$C_1$-$C_3$-alkyl" means a straight or branched chain, saturated hydrocarbon containing 1 to 3 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched, saturated hydrocarbon chain. Examples of alkylene include, but are not limited to, —CH$_2$—, —CH$_2$CH$_2$—, —CH$_2$CH$_2$CH$_2$—, —CH$_2$CH$_2$CH$_2$CH$_2$—, —CH(CH$_3$)—, and —CH$_2$CH(CH$_3$)CH$_2$—.

The term "alkynyl", means a straight or branched chain hydrocarbon group containing at least one carbon-carbon triple bond. The term "$C_2$-$C_{10}$-alkynyl" means an alkynyl group containing from 2 to 10 carbon atoms. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. For example, "$C_6$-$C_{10}$-aryl" refers to an aryl group that may have from six to ten carbon atoms. The bicyclic aryl is naphthyl, or a phenyl fused to a monocyclic cycloalkyl, or a phenyl fused to a monocyclic cycloalkenyl. Non-limiting examples of the aryl groups include dihydroindenyl, indenyl, naphthyl, dihydronaphthalenyl, and tetrahydronaphthalenyl. The aryl groups can be unsubstituted or substituted, and the bicyclic aryl is attached to the parent molecular moiety through any substitutable carbon atom contained within the bicyclic ring system.

The term "arylalkyl," as used herein, refers to an aryl group attached to the parent molecular moiety through an alkyl group.

The term "cyano" means —CN, which also may be depicted as —C≡N.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be attached to the parent molecular moiety through any substitutable atom contained within the ring systems, and can be unsubstituted or substituted.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. Tricyclic cycloalkyls are exemplified by a bicyclic cycloalkyl fused to a monocyclic cycloalkyl. The monocyclic or bicyclic cycloalkyl ring may contain one or two alkylene bridges, each consisting of one, two, or three carbon atoms, each linking two non-adjacent carbon atoms of the ring system. Non-limiting examples of such bridged cycloalkyl ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "cycloalkylalkyl," as used herein, refers to a cycloalkyl group attached to the parent molecular moiety through an alkyl group.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. The term "$C_1$-$C_{10}$-haloalkyl" means a $C_1$-$C_{10}$ alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, trifluorobutyl (such as, but not limited to, 4,4,4-trifluorobutyl), and trifluoropropyl (such as, but not limited thereto, 3,3,3-trifluoropropyl).

The term "haloalkenyl", as used herein, refers to an alkenyl group, as defined herein, substituted by one, two, three, or four halogen atoms.

The term "haloalkynyl", as used herein, refers to an alkynyl group, as defined herein, substituted by one, two, three, or four halogen atoms.

The term "heterocycle", "heterocyclyl", or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contain zero, one, two, or three double bonds and one, two, or three heteroatoms selected from the group consisting of O, N, and S, Non-limiting examples of monocyclic heterocycles include azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl (including, but not limited thereto, pyrrolidin-1-yl, pyrrolidin-2-yl, pyrrolidin-3-yl), tetrahydrofuranyl (including, but not limited thereto, tetrahydrofuran-3-yl), tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Non-limiting examples of bicyclic heterocycles include benzopyranyl, benzothiopyranyl, 2,3-dihydrobenzofuranyl, 2,3-dihydrobenzothienyl, benzo[d][1,3]dioxolyl, chromanyl and 2,3-dihydro-1H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle. The monocyclic and the bicyclic heterocycles may contain an alkenylene bridge of two, three, or four carbon atoms, or one or two alkylene bridges of 1, 2, 3, or 4 carbon atoms, or combinations thereof, wherein each bridge links two non-adjacent atoms of the ring system. Non-limiting examples of such bridged heterocycles include octahydro-2,5-epoxypentalene, azabicyclo[2.2.1]heptyl (including 2-azabicyclo[2.2.1]hept-2-yl), hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles can be unsubstituted or substituted, and are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quaternized. The term "N-heterocyclyl" refers to a nitrogen-containing heterocyclic group attached to the parent molecular moiety through a nitrogen atom.

The term "heterocyclylalkyl," as used herein, refers to a heterocyclyl group attached to the parent molecular moiety through an alkyl group.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl (including, but not limited thereto, furan-2-yl), imidazolyl (including, but not limited thereto, 1H-imidazol-1-yl), isoxazolyl, isothiazolyl, oxadiazolyl, 1,3-oxazolyl, pyridinyl (e.g. pyridin-4-yl, pyridin-2-yl, pyridin-3-yl), pyridazinyl, pyrimidinyl, pyrazinyl, pyrazolyl, pyrrolyl, tetrazolyl, thiadiazolyl, 1,3-thiazolyl, thienyl (including, but not limited thereto, thien-2-yl, thien-3-yl), triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Non-limiting examples of bicyclic heteroaryl groups include benzofuranyl, benzothienyl, benzoxazolyl, benzimidazolyl, benzoxadiazolyl, 6,7-dihydro-1,3-benzothiazolyl, furo[3,2-c]pyridazinyl, furo[3,2-d]pyrimidinyl, furo[2,3-b]pyrazinyl, furo[2,3-c]pyridazinyl, furo[2,3-d]pyrimidinyl, furo[3,2-b]pyridinyl, furo[3,2-c]pyridinyl, furo[2,3-c]pyridinyl, furo[2,3-b]pyridine, imidazo[2,1-b]oxazolyl, imidazo[1,2-a]pyridinyl, imidazo[2,1-b][1,3,4]thiadiazolyl, imidazo[2,1-b][1,3,4]thiadiazolyl, imidazo[1,2-d][1,2,4]thiadiazolyl, imidazo[2,1-b]thiazolyl, indazolyl, indolizinyl, indolyl, isoindolyl, isoquinolinyl, naphthyridinyl, pyrazolo[1,5-a]pyridinyl, pyrazolo[1,5-c]pyrimidinyl, pyrazolo[1,5-a]pyrimidinyl, pyrazolo[5,1-c][1,2,4]triazinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any substitutable carbon atom or any substitutable nitrogen atom contained within the ring systems.

The term "heteroarylalkyl," as used herein, refers to a heteroaryl group attached to the parent molecular moiety through an alkyl group.

The term "heteroatom" as used herein, means a nitrogen, oxygen, or sulfur atom.

The term "hydroxyl" or "hydroxy" means a —OH group.

The term "monocyclic heteroarylalkyl," as used herein, refers to a monocyclic heteroaryl group attached to the parent molecular moiety through an alkyl group.

The term "oxo" as used herein, means a =O group.

The term "phenylalkyl," as used herein, refers to a phenyl group attached to the parent molecular moiety through an alkyl group.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkoxyalkyl indicates that only the alkoxy component of the alkoxyalkyl substituent is substituted with one or more halogen radicals. If halogen substitution may alternatively or additionally occur on the alkyl component, the substituent would instead be described as "halogen-substituted alkoxyalkyl" rather than "haloalkoxyalkyl." And finally, if the halogen substitution may only occur on the alkyl component, the substituent would instead be described as "alkoxyhaloalkyl."

If substituents are described as being "independently selected" from a group, each substituent is selected independent of the other. Each substituent, therefore, may be identical to or different from the other substituent(s).

When words are used to describe a substituent, the rightmost-described component of the substituent is the component that has the free valence.

When a chemical formula is used to describe a substituent, the dash on the left side of the formula indicates the portion of the substituent that has the free valence.

When a chemical formula is used to describe a linking element between two other elements of a depicted chemical structure, the leftmost dash of the substituent indicates the portion of the substituent that is bound to the left element in the depicted structure. The rightmost dash, on the other hand, indicates the portion of the substituent that is bound to the right element in the depicted structure. To illustrate, if the depicted chemical structure is W-L-Y and L is described as —C(O)—N(H)—, then the chemical would be W—C(O)—N(H)—Y.

Compounds of formula (I) are as described herein.

Particular values of variable groups in compounds of formula (I) are as follows. Such values may be used where appropriate with any of the other values, definitions, claims or embodiments defined herein.

In certain embodiments, $R^1$ is $C_1$-$C_6$-alkyl, $C_1$-$C_6$-haloalkyl, $C_3$-$C_8$-cycloalkyl, $C_3$-$C_8$-cycloalkyl-$C_1$-$C_6$-alkyl, phenyl, bicyclic aryl, phenyl-$C_1$-$C_6$-alkyl, heterocyclyl, heterocyclyl-$C_1$-$C_6$-alkyl, monocyclic heteroaryl, or monocyclic heteroaryl-$C_1$-$C_6$-alkyl; wherein the $C_3$-$C_8$-cycloalkyl, the $C_3$-$C_8$-cycloalkyl of $C_3$-$C_8$-cycloalkyl-$C_1$-$C_6$-alkyl, heterocyclyl, and heterocyclyl of heterocyclyl-$C_1$-$C_6$-alkyl are optionally substituted with 1, 2, 3, or 4 substituents selected from the group consisting of $C_1$-$C_{10}$-alkyl, $C_2$-$C_{10}$-alkenyl, $C_2$-$C_{10}$-alkynyl, $C_1$-$C_{10}$-haloalkyl, $C_2$-$C_{10}$-haloalkenyl, $C_2$-$C_{10}$-haloalkynyl, halogen, oxo, cyano, hydroxy, —O—$C_1$-$C_6$-alkyl, —O—$C_1$-$C_6$-haloalkyl, —$C_1$-$C_3$-alkylene-O—H, —$C_1$-$C_3$-alkylene-O—$C_1$-$C_6$-alkyl, —$C_1$-$C_3$-alkylene-O—$C_1$-$C_6$-haloalkyl, —$C_1$-$C_3$-alkylene-NH$_2$, —NH$_2$, —C(O)O—$C_1$-$C_6$-alkyl, —N($R^{b1}$)C(O)$R^{b1}$, —CON($R^{a1}$)($R^{b1}$), —C(O)$R^{b1}$, —OC(O)$R^{b1}$, —OS(O)$_2$N($R^{a1}$)($R^{b1}$), —CO$_2$H, —CO$_2R^{b1}$, —N($R^{b1}$)C(O)N($R^{b1}$)$_2$, —S—$R^{b1}$, —S(O)$_2R^{b1}$, —S(O)$R^{b1}$, —SO$_2$N($R^{a1}$)($R^{b1}$), —N($R^{a1}$)($R^{b1}$), —N($R^{b1}$)S(O)$_2R^{b1}$, —N($R^{b1}$)C(O)O$R^{b1}$, —N($R^{b1}$)S(O)$_2$O($R^{b1}$), -$L^{1a}$-O—$R^{b1}$, -$L^{1a}$-CN, -$L^{1a}$-N($R^{b1}$)C(O)$R^{b1}$, -$L^{1a}$-CON($R^{a1}$)($R^{b1}$), -$L^{1a}$-C(O)$R^{b1}$, -$L^{1a}$-OC(O)$R^{b1}$, -$L^{1a}$-CO$_2$H, -$L^{1a}$-CO$_2R^{b1}$, -$L^{1a}$-N($R^{b1}$)C(O)N($R^{b1}$)$_2$, -$L^{1a}$-S—$R^{b1}$, -$L^{1a}$-S(O)$_2R^{b1}$, -$L^{1a}$-S(O)$R^{b1}$, -$L^{1a}$-SO$_2$N($R^{a1}$)($R^{b1}$), -$L^{1a}$-N($R^{a1}$)($R^{b1}$), -$L^{1a}$-N($R^{b1}$)S(O)$_2R^{b1}$, and -$L^{1a}$-N($R^{b1}$)C(O)O($R^{b1}$); wherein the phenyl, the bicyclic aryl, the phenyl of phenyl-$C_1$-$C_6$-alkyl, the monocyclic heteroaryl and monocyclic heteroaryl of monocyclic heteroaryl-$C_1$-$C_6$-alkyl are optionally substituted with 1, 2, 3, 4, or 5 substituents selected from the group consisting of halogen, $C_1$-$C_6$-alkyl, $C_1$-$C_6$-haloalkyl, —OCH$_2$O—, —O—$R^b$, —CN, —N($R^b$)C(O)$R^b$, —CON($R^a$)($R^b$), —C(O)$R^b$, —OC(O)$R^b$, —OS(O)$_2$N($R^a$)($R^b$), —CO$_2$H, —CO$_2$R$^b$, —N(R$^b$)C(O)N(R$^b$)$_2$, —S—R$^b$, —S(O)$_2$R$^b$, —S(O)R$^b$, —SO$_2$N(R$^a$)(R$^b$), —N(R$^a$)(R$^b$), —N(R$^b$)S(O)$_2$R$^b$, —N(R$^b$)C(O)O(R$^b$), —N(R$^b$)S(O)$_2$O(R$^b$), -L$^1$-O—R$^b$, -L$^1$-CN, -L$^1$-N(R$^b$)C(O)R$^b$, -L$^1$-CON(R$^a$)(R$^b$), -L$^1$-C(O)R$^b$, -L$^1$-OC(O)R$^b$, -L$^1$-CO$_2$H, -L$^1$-CO$_2$R$^b$, -L$^1$-N(R$^b$)C(O)N(R$^b$)$_2$, -L$^1$-S—R$^b$, -L$^1$-S(O)$_2$R$^b$, -L$^1$-S(O)R$^b$, -L$^1$-SO$_2$N(R$^a$)(R$^b$), -L$^1$-N(R$^a$)(R$^b$), -L$^1$-N(R$^b$)S(O)$_2$R$^b$, and -L$^1$-N(R$^b$)C(O)O(R$^b$); wherein L$^1$, L$^{1a}$, R$^a$, R$^{a1}$, R$^b$ and R$^{b1}$ are as described herein.

In certain embodiments, R$^1$ is C$_1$-C$_6$-alkyl or C$_1$-C$_6$-haloalkyl.

In certain embodiments, R$^1$ is C$_3$-C$_8$-cycloalkyl, C$_3$-C$_8$-cycloalkyl-C$_1$-C$_6$-alkyl, phenyl, bicyclic aryl, phenyl-C$_1$-C$_6$-alkyl, heterocyclyl, heterocyclyl-C$_1$-C$_6$-alkyl, monocyclic heteroaryl, or monocyclic heteroaryl-C$_1$-C$_6$-alkyl; wherein the C$_3$-C$_8$-cycloalkyl, the C$_3$-C$_8$-cycloalkyl of C$_3$-C$_8$-cycloalkyl-C$_1$-C$_6$-alkyl, heterocyclyl, and heterocyclyl of heterocyclyl-C$_1$-C$_6$-alkyl are optionally substituted with 1, 2, 3, or 4 substituents selected from the group consisting of C$_1$-C$_{10}$-alkyl, C$_2$-C$_{10}$-alkenyl, C$_2$-C$_{10}$-alkynyl, C$_1$-C$_{10}$-haloalkyl, C$_2$-C$_{10}$-haloalkenyl, C$_2$-C$_{10}$-haloalkynyl, halogen, oxo, cyano, hydroxy, —O—C$_1$-C$_6$-alkyl, —O—C$_1$-C$_6$-haloalkyl, —C$_1$-C$_3$-alkylene-O—H, —C$_1$-C$_3$-alkylene-O—C$_1$-C$_6$-alkyl, —C$_1$-C$_3$-alkylene-O—C$_1$-C$_6$-haloalkyl, —C$_1$-C$_3$-alkylene-NH$_2$, —NH$_2$, —C(O)O—C$_1$-C$_6$-alkyl, —N(R$^{b1}$)C(O)R$^{b1}$, —CON(R$^{a1}$)(R$^{b1}$), —C(O)R$^{b1}$, —OC(O)R$^{b1}$, —OS(O)$_2$N(R$^{a1}$)(R$^{b1}$), —CO$_2$H, —CO$_2$R$^{b1}$, —N(R$^{b1}$)C(O)N(R$^{b1}$)$_2$, —S—R$^{b1}$, —S(O)$_2$R$^{b1}$, —S(O)R$^{b1}$, —SO$_2$N(R$^{a1}$)(R$^{b1}$), —N(R$^{a1}$)(R$^{b1}$), —N(R$^{b1}$)S(O)$_2$R$^{b1}$, —N(R$^{b1}$)C(O)O(R$^{b1}$), —N(R$^{b1}$)S(O)$_2$O(R$^{b1}$), -L$^{1a}$-O—R$^{b1}$, -L$^{1a}$-CN, -L$^{1a}$-N(R$^{b1}$)C(O)R$^{b1}$, -L$^{1a}$-CON(R$^{a1}$)(R$^{b1}$), -L$^{1a}$-C(O)R$^{b1}$, -L$^{1a}$-OC(O)R$^{b1}$, -L$^{1a}$-CO$_2$H, -L$^{1a}$-CO$_2$R$^{b1}$, -L$^{1a}$-N(R$^{b1}$)C(O)N(R$^{b1}$)$_2$, -L$^{1a}$-S—R$^{b1}$, -L$^{1a}$-S(O)$_2$R$^{b1}$, -L$^{1a}$-S(O)R$^{b1}$, -L$^{1a}$-SO$_2$N(R$^{a1}$)(R$^{b1}$), -L$^{1a}$-N(R$^{a1}$)(R$^{b1}$), -L$^{1a}$-N(R$^{b1}$)S(O)$_2$R$^{b1}$, and -L$^{1a}$-N(R$^{b1}$)C(O)O(R$^{b1}$); wherein the phenyl, the bicyclic aryl, the phenyl of phenyl-C$_1$-C$_6$-alkyl, the monocyclic heteroaryl and monocyclic heteroaryl of monocyclic heteroaryl-C$_1$-C$_6$-alkyl are optionally substituted with 1, 2, 3, 4, or 5 substituents selected from the group consisting of halogen, C$_1$-C$_6$-alkyl, C$_1$-C$_6$-haloalkyl, —OCH$_2$O—, —O—R$^b$, —CN, —N(R$^b$)C(O)R$^b$, —CON(R$^a$)(R$^b$), —C(O)R$^b$, —OC(O)R$^b$, —OS(O)$_2$N(R$^a$)(R$^b$), —CO$_2$H, —CO$_2$R$^b$, —N(R$^b$)C(O)N(R$^b$)$_2$, —S—R$^b$, —S(O)$_2$R$^b$, —S(O)R$^b$, —SO$_2$N(R$^a$)(R$^b$), —N(R$^a$)(R$^b$), —N(R$^b$)S(O)$_2$R$^b$, —N(R$^b$)C(O)O(R$^b$), —N(R$^b$)S(O)$_2$O(R$^b$), -L$^1$-O—R$^b$, -L$^1$-CN, -L$^1$-N(R$^b$)C(O)R$^b$, -L$^1$-CON(R$^a$)(R$^b$), -L$^1$-C(O)R$^b$, -L$^1$-OC(O)R$^b$, -L$^1$-CO$_2$H, -L$^1$-CO$_2$R$^b$, -L$^1$-N(R$^b$)C(O)N(R$^b$)$_2$, -L$^1$-S—R$^b$, -L$^1$-S(O)$_2$R$^b$, -L$^1$-S(O)R$^b$, -L$^1$-SO$_2$N(R$^a$)(R$^b$), -L$^1$-N(R$^a$)(R$^b$), -L$^1$-N(R$^b$)S(O)$_2$R$^b$, and -L$^1$-N(R$^b$)C(O)O(R$^b$); wherein L$^1$, L$^{1a}$, R$^a$, R$^{a1}$, R$^b$ and R$^{b1}$ are as described herein.

In certain embodiments, R$^1$ is C$_3$-C$_8$-cycloalkyl, phenyl, bicyclic aryl, heterocyclyl, or monocyclic heteroaryl; wherein the C$_3$-C$_8$-cycloalkyl and heterocyclyl are optionally substituted with 1, 2, 3, or 4 substituents selected from the group consisting of C$_1$-C$_{10}$-alkyl, C$_2$-C$_{10}$-alkenyl, C$_2$-C$_{10}$-alkynyl, C$_1$-C$_{10}$-haloalkyl, C$_2$-C$_{10}$-haloalkenyl, C$_2$-C$_{10}$-haloalkynyl, halogen, oxo, cyano, hydroxy, O—C$_1$-C$_6$-alkyl, —O—C$_1$-C$_6$-haloalkyl, —C$_1$-C$_3$-alkylene-O—H, —C$_1$-C$_3$-alkylene-O—C$_1$-C$_6$-alkyl, —C$_1$-C$_3$-alkylene-O—C$_1$-C$_6$-haloalkyl, —C$_1$-C$_3$-alkylene-NH$_2$, —NH$_2$, —C(O)O—C$_1$-C$_6$-alkyl, —N(R$^{b1}$)C(O)R$^{b1}$, —CON(R$^{a1}$)(R$^{b1}$), —C(O)R$^{b1}$, —OC(O)R$^{b1}$, —OS(O)$_2$N(R$^{a1}$)(R$^{b1}$), —CO$_2$H, —CO$_2$R$^{b1}$, —N(R$^{b1}$)C(O)N(R$^{b1}$)$_2$, —S—R$^{b1}$, —S(O)$_2$R$^{b1}$, —S(O)R$^{b1}$, —SO$_2$N(R$^{a1}$)(R$^{b1}$), —N(R$^{a1}$)(R$^{b1}$), —N(R$^{b1}$)S(O)$_2$R$^{b1}$, —N(R$^{b1}$)C(O)O(R$^{b1}$), —N(R$^{b1}$)S(O)$_2$O(R$^{b1}$), -L$^{1a}$-O—R$^{b1}$, -L$^{1a}$-CN, -L$^{1a}$-N(R$^{b1}$)C(O)R$^{b1}$, -L$^{1a}$-CON(R$^{a1}$)(R$^{b1}$), -L$^{1a}$-C(O)R$^{b1}$, -L$^{1a}$-OC(O)R$^{b1}$, -L$^{1a}$-CO$_2$H, -L$^{1a}$-CO$_2$R$^{b1}$, -L$^{1a}$-N(R$^{b1}$)C(O)N(R$^{b1}$)$_2$, -L$^{1a}$-S—R$^{b1}$, -L$^{1a}$-S(O)$_2$R$^{b1}$, -L$^{1a}$-S(O)R$^{b1}$, -L$^{1a}$-SO$_2$N(R$^{a1}$)(R$^{b1}$), -L$^{1a}$-N(R$^{a1}$)(R$^{b1}$), -L$^{1a}$-N(R$^{b1}$)S(O)$_2$R$^{b1}$, and -L$^{1a}$-N(R$^{b1}$)C(O)O(R$^{b1}$); wherein the phenyl, the bicyclic aryl, and the monocyclic heteroaryl are optionally substituted with 1, 2, 3, 4, or 5 substituents selected from the group consisting of halogen, C$_1$-C$_6$-alkyl, C$_1$-C$_6$-haloalkyl, —OCH$_2$O—, —O—R$^b$, —CN, —N(R$^b$)C(O)R$^b$, —CON(R$^a$)(R$^b$), —C(O)R$^b$, —OC(O)R$^b$, —OS(O)$_2$N(R$^a$)(R$^b$), —CO$_2$H, —CO$_2$R$^b$, —N(R$^b$)C(O)N(R$^b$)$_2$, —S—R$^b$, —S(O)$_2$R$^b$, —S(O)R$^b$, —SO$_2$N(R$^a$)(R$^b$), —N(R$^a$)(R$^b$), —N(R$^b$)S(O)$_2$R$^b$, —N(R$^b$)C(O)O(R$^b$), —N(R$^b$)S(O)$_2$O(R$^b$), -L$^1$-O—R$^b$, -L$^1$- CN, -L$^1$-N(R$^b$)C(O)R$^b$, -L$^1$-CON(R$^a$)(R$^b$), -L$^1$-C(O)R$^b$, -L$^1$-OC(O)R$^b$, -L$^1$-CO$_2$H, -L$^1$-CO$_2$R$^b$, -L$^1$-N(R$^b$)C(O)N(R$^b$)$_2$, -L$^1$-S—R$^b$, -L$^1$-S(O)$_2$R$^b$, -L$^1$-S(O)R$^b$, -L$^1$-SO$_2$N(R$^a$)(R$^b$), -L$^1$-N(R$^a$)(R$^b$), -L$^1$-N(R$^b$)S(O)$_2$R$^b$, and -L$^1$-N(R$^b$)C(O)O(R$^b$); wherein L$^1$, -L$^{1a}$, R$^a$, R$^{a1}$, R$^b$ and R$^{b1}$ are as described herein.

In certain embodiments, R$^1$ is C$_3$-C$_8$-cycloalkyl or heterocyclyl; wherein the C$_3$-C$_8$-cycloalkyl and heterocyclyl are optionally substituted with 1, 2, 3, or 4 substituents selected from the group consisting of C$_1$-C$_{10}$-alkyl, C$_2$-C$_{10}$-alkenyl, C$_2$-C$_{10}$-alkynyl, C$_1$-C$_{10}$-haloalkyl, C$_2$-C$_{10}$-haloalkenyl, C$_2$-C$_{10}$-haloalkynyl, halogen, oxo, cyano, hydroxy, —O—C$_1$-C$_6$-alkyl, —O—C$_1$-C$_6$-haloalkyl, —C$_1$-C$_3$-alkylene-O—H, —C$_1$-C$_3$-alkylene-O—C$_1$-C$_6$-alkyl, —C$_1$-C$_3$-alkylene-O—C$_1$-C$_6$-haloalkyl, —C$_1$-C$_3$-alkylene-NH$_2$, —NH$_2$, —C(O)O—C$_1$-C$_6$-alkyl, —N(R$^{b1}$)C(O)R$^{b1}$, —CON(R$^{a1}$)(R$^{b1}$), —C(O)R$^{b1}$, —OC(O)R$^{b1}$, —OS(O)$_2$N(R$^{a1}$)(R$^{b1}$), —CO$_2$H, —CO$_2$R$^{b1}$, —N(R$^{b1}$)C(O)N(R$^{b1}$)$_2$, —S—R$^{b1}$, —S(O)$_2$R$^{b1}$, —S(O)R$^{b1}$, —SO$_2$N(R$^{a1}$)(R$^{b1}$), —N(R$^{a1}$)(R$^{b1}$), —N(R$^{b1}$)S(O)$_2$R$^{b1}$, —N(R$^{b1}$)C(O)O(R$^{b1}$), —N(R$^{b1}$)S(O)$_2$O(R$^{b1}$), -L$^{1a}$-O—R$^{b1}$, -L$^{1a}$-CN, -L$^{1a}$-N(R$^{b1}$)C(O)R$^{b1}$, -L$^{1a}$-CON(R$^{a1}$)(R$^{b1}$), -L$^{1a}$-C(O)R$^{b1}$, -L$^{1a}$-OC(O)R$^{b1}$, -L$^{1a}$-CO$_2$H, -L$^{1a}$-CO$_2$R$^{b1}$, -L$^{1a}$-N(R$^{b1}$)C(O)N(R$^{b1}$)$_2$, -L$^{1a}$-S—R$^{b1}$, -L$^{1a}$-S(O)$_2$R$^{b1}$, -L$^{1a}$-S(O)R$^{b1}$, -L$^{1a}$-SO$_2$N(R$^{a1}$)(R$^{b1}$), -L$^{1a}$-N(R$^{a1}$)(R$^{b1}$), -L$^{1a}$-N(R$^{b1}$)S(O)$_2$R$^{b1}$, and -L$^{1a}$-N(R$^{b1}$)C(O)O(R$^{b1}$); wherein L$^{1a}$, R$^{a1}$ and R$^{b1}$ are as described herein.

In certain embodiments, R$^1$ is C$_3$-C$_8$-cycloalkyl selected from the group consisting of cyclobutane, cyclopentane, cyclohexane, cycloheptane and norbornyl; wherein the C$_3$-C$_8$-cycloalkyl is optionally substituted with 1, 2, 3, or 4 substituents selected from the group consisting of C$_1$-C$_{10}$-alkyl, C$_2$-C$_{10}$-alkenyl, C$_2$-C$_{10}$-alkynyl, C$_1$-C$_{10}$-haloalkyl, C$_2$-C$_{10}$-haloalkenyl, C$_2$-C$_{10}$-haloalkynyl, halogen, oxo, cyano, hydroxy, —O—C$_1$-C$_6$-alkyl, —O—C$_1$-C$_6$-haloalkyl, —C$_1$-C$_3$-alkylene-O—H, —C$_1$-C$_3$-alkylene-O—C$_1$-C$_6$-alkyl, —C$_1$-C$_3$-alkylene-O—C$_1$-C$_6$-haloalkyl, —C$_1$-C$_3$-alkylene-NH$_2$, —NH$_2$, —C(O)O—C$_1$-C$_6$-alkyl, —N(R$^{b1}$)C(O)R$^{b1}$, —CON(R$^{a1}$)(R$^{b1}$), —C(O)R$^{b1}$, —OC(O)R$^{b1}$, —OS(O)$_2$N(R$^{a1}$)(R$^{b1}$), —CO$_2$H, —CO$_2$R$^{b1}$, —N(R$^{b1}$)C(O)N(R$^{b1}$)$_2$, —S—R$^{b1}$, —S(O)$_2$R$^{b1}$, —S(O)R$^{b1}$, —SO$_2$N(R$^{a1}$)(R$^{b1}$), —N(R$^{a1}$)(R$^{b1}$), —N(R$^{b1}$)S(O)$_2$R$^{b1}$, —N(R$^{b1}$)C(O)O(R$^{b1}$), —N(R$^{b1}$)S(O)$_2$O(R$^{b1}$), -L$^{1a}$-O—R$^{b1}$, -L$^{1a}$-CN, -L$^{1a}$-N(R$^{b1}$)C(O)R$^{b1}$, -L$^{1a}$-CON(R$^{a1}$)(R$^{b1}$), -L$^{1a}$-C(O)R$^{b1}$, -L$^{1a}$-OC(O)R$^{b1}$, -L$^{1a}$-CO$_2$H, -L$^{1a}$-CO$_2$R$^{b1}$, -L$^{1a}$-N(R$^{b1}$)C(O)N(R$^{b1}$)$_2$, -L$^{1a}$-S—R$^{b1}$, -L$^{1a}$-S(O)$_2$R$^{b1}$, -L$^{1a}$-S(O)R$^{b1}$, -L$^{1a}$-SO$_2$N(R$^{a1}$)(R$^{b1}$), -L$^{1a}$-N(R$^{a1}$)(R$^{b1}$), -L$^{1a}$-N(R$^{b1}$)S(O)$_2$R$^{b1}$, and -L$^{1a}$-N(R$^{b1}$)C(O)O(R$^{b1}$); wherein L$^{1a}$, R$^{a1}$ and R$^{b1}$ are as described herein.

In certain embodiments, R$^1$ is C$_3$-C$_8$-cycloalkyl selected from the group consisting of cyclobutane, cyclopentane, cyclohexane, cycloheptane and norbornyl; wherein the C$_3$-C$_8$-cycloalkyl is optionally substituted with 1, 2, or 3, or 4 substituents selected from the group consisting of halogen, hydroxy, hydroxymethyl, methyl, and trifluoromethyl.

In certain embodiments, $R^1$ is heterocyclyl selected from the group consisting of tetrahydro-2H-pyran-4-yl, 3,4-dihydro-2H-chromen-4-yl, tetrahydrothiophen-3-yl and piperidin-4-yl; wherein the heterocyclyl is optionally substituted with 1, 2, 3, or 4 substituents selected from the group consisting of $C_1$-$C_{10}$-alkyl, $C_2$-$C_{10}$-alkenyl, $C_2$-$C_{10}$-alkynyl, $C_1$-$C_{10}$-haloalkyl, $C_2$-$C_{10}$-haloalkenyl, $C_2$-$C_{10}$-haloalkynyl, halogen, oxo, cyano, hydroxy, —O—$C_1$-$C_6$-alkyl, —O—$C_1$-$C_6$-haloalkyl, —$C_1$-$C_3$-alkylene-O—H, —$C_1$-$C_3$-alkylene-O—$C_1$-$C_6$-alkyl, —$C_1$-$C_3$-alkylene-O—$C_1$-$C_6$-haloalkyl, —$C_1$-$C_3$-alkylene-NH$_2$, —NH$_2$, —C(O)O—$C_1$-$C_6$-alkyl, —N($R^{b1}$)C(O)$R^{b1}$, —CON($R^{a1}$)($R^{b1}$), —C(O)$R^{b1}$, —OC(O)$R^{b1}$, —OS(O)$_2$N($R^{a1}$)($R^{b1}$), —CO$_2$H, —CO$_2R^{b1}$, —N($R^{b1}$)C(O)N($R^{b1}$)$_2$, —S—$R^{b1}$, —S(O)$_2R^{b1}$, —S(O)$R^{b1}$, —SO$_2$N($R^{a1}$)($R^{b1}$), —N($R^{a1}$)($R^{b1}$), —N($R^{b1}$)S(O)$_2R^{b1}$, —N($R^{b1}$)C(O)O($R^{b1}$), —N($R^{b1}$)S(O)$_2$O($R^{b1}$), -$L^{1a}$-O—$R^{b1}$, -$L^{1a}$-CN, -$L^{1a}$-N($R^{b1}$)C(O)$R^{b1}$, -$L^{1a}$-CON($R^{a1}$)($R^{b1}$), -$L^{1a}$-C(O)$R^{b1}$, -$L^{1a}$-OC(O)$R^{b1}$, -$L^{1a}$-CO$_2$H, -$L^{1a}$-CO$_2R^{b1}$, -$L^{1a}$-N($R^{b1}$)C(O)N($R^{b1}$)$_2$, -$L^{1a}$-S—$R^{b1}$, -$L^{1a}$-S(O)$_2R^{b1}$, -$L^{1a}$-S(O)$R^{b1}$, -$L^{1a}$-SO$_2$N($R^{a1}$)($R^{b1}$), -$L^{1a}$-N($R^{a1}$)($R^{b1}$), -$L^{1a}$-N($R^{b1}$)S(O)$_2R^{b1}$, and -$L^{1a}$-N($R^{b1}$)C(O)O($R^{b1}$); wherein $L^{1a}$, $R^{a1}$ and $R^{b1}$ are as described herein.

In certain embodiments, $R^1$ is heterocyclyl selected from the group consisting of tetrahydro-2H-pyran-4-yl, 3,4-dihydro-2H-chromen-4-yl, tetrahydrothiophen-3-yl and piperidin-4-yl; wherein the heterocyclyl is optionally substituted with 1, 2, or 3, or 4 substituents selected from the group consisting of oxo, methyl, and —C(O)O—$C_1$-$C_6$-alkyl.

In certain embodiments, $R^1$ is phenyl, bicyclic aryl, or monocyclic heteroaryl; wherein the phenyl, the bicyclic aryl, and the monocyclic heteroaryl are optionally substituted with 1, 2, 3, 4, or 5 substituents selected from the group consisting of halogen, $C_1$-$C_6$-alkyl, $C_1$-$C_6$-haloalkyl, —OCH$_2$O—, —O—$R^b$, —CN, —N($R^b$)C(O)$R^b$, —CON($R^a$)($R^b$), —C(O)$R^b$, —OC(O)$R^b$, —OS(O)$_2$N($R^a$)($R^b$), —CO$_2$H, —CO$_2R^b$, —N($R^b$)C(O)N($R^b$)$_2$, —S—$R^b$, —S(O)$_2R^b$, —S(O)$R^b$, —SO$_2$N($R^a$)($R^b$), —N($R^a$)($R^b$), —N($R^b$)S(O)$_2R^b$, —N($R^b$)C(O)O($R^b$), —N($R^b$)S(O)$_2$O($R^b$), -$L^1$-O—$R^b$, -$L^1$-CN, -$L^1$-N($R^b$)C(O)$R^b$, -$L^1$-CON($R^a$)($R^b$), -$L^1$-C(O)$R^b$-$L^1$-CO$_2$H, -$L^1$-CO$_2R^b$, -$L^1$-N($R^b$)C(O)N($R^b$)$_2$, -$L^1$-S—$R^b$, -$L^1$-S(O)$_2R^b$, -$L^1$-S(O)$R^b$, -$L^1$-SO$_2$N($R^a$)($R^b$), -$L^1$-N($R^a$)($R^b$), -$L^1$-N($R^b$)S(O)$_2R^b$, and -$L^1$-N($R^b$)C(O)O($R^b$); wherein $L^1$, $R^a$, and $R^b$ are as described herein.

In certain embodiments, $R^1$ is phenyl; wherein the phenyl is optionally substituted with 1, 2, 3, 4, or 5 substituents selected from the group consisting of halogen, $C_1$-$C_6$-alkyl, $C_1$-$C_6$-haloalkyl, —OCH$_2$O—, —O—$R^b$, —CN, —N($R^b$)C(O)$R^b$, —CON($R^a$)($R^b$), —C(O)$R^b$, —OC(O)$R^b$, —OS(O)$_2$N($R^a$)($R^b$), —CO$_2$H, —CO$_2R^b$, —N($R^b$)C(O)N($R^b$)$_2$, —S—$R^b$, —S(O)$_2R^b$, —S(O)$R^b$, —SO$_2$N($R^a$)($R^b$), —N($R^a$)($R^b$), —N($R^b$)S(O)$_2R^b$, —N($R^b$)C(O)O($R^b$), —N($R^b$)S(O)$_2$O($R^b$), -$L^1$-O—$R^b$, -$L^1$-CN, -$L^1$-N($R^b$)C(O)$R^b$, -$L^1$-CON($R^a$)($R^b$), -$L^1$-C(O)$R^b$-$L^1$-CO$_2$H, -$L^1$-CO$_2R^b$, -$L^1$-N($R^b$)C(O)N($R^b$) S—$R^b$, -$L^1$-S(O)$_2R^b$, -$L^1$-S(O)$R^b$, -$L^1$-SO$_2$N($R^a$)($R^b$), -$L^1$-N($R^a$)($R^b$), -$L^1$-N($R^b$)S(O)$_2R^b$, and -$L^1$-N($R^b$)C(O)O($R^b$); wherein $L^1$, $R^a$, and $R^b$ are as described herein.

In certain embodiments, $R^1$ is phenyl; wherein the phenyl is optionally substituted with 1, 2, 3, 4, or 5 substituents selected from the group consisting of halogen, $C_1$-$C_6$-alkyl, $C_1$-$C_6$-haloalkyl, —OCH$_2$O—, —O—$R^b$; wherein $R^b$ is as described in the Summary.

In certain embodiments, $R^1$ is bicyclic aryl selected from the group consisting of 2,3-dihydro-1H-inden-1-yl, 1,2,3,4-tetrahydronaphthalen-1-yl, and 2,3-dihydro-1H-inden-2-yl; wherein the bicyclic aryl is optionally substituted with 1, 2, 3, 4, or 5 substituents selected from the group consisting of halogen, $C_1$-$C_6$-alkyl, $C_1$-$C_6$-haloalkyl, —OCH$_2$O—, —O—$R^b$, —CN, —N($R^b$)C(O)$R^b$, —CON($R^a$)($R^b$), —C(O)$R^b$, —OC(O)$R^b$, —OS(O)$_2$N($R^a$)($R^b$), —CO$_2$H, —CO$_2R^b$, —N($R^b$)C(O)N($R^b$)$_2$, —S—$R^b$, —S(O)$_2R^b$, —S(O)$R^b$, —SO$_2$N($R^a$)($R^b$), —N($R^a$)($R^b$), —N($R^b$)S(O)$_2R^b$, —N($R^b$)C(O)O($R^b$), —N($R^b$)S(O)$_2$O($R^b$), -$L^1$-O—$R^b$, -$L^1$-CN, -$L^1$-N($R^b$)C(O)$R^b$, -$L^1$-CON($R^a$)($R^b$), -$L^1$-C(O)$R^b$, -$L^1$-OC(O)$R^b$, -$L^1$-CO$_2$H, -$L^1$-CO$_2R^b$, -$L^1$-N($R^b$)C(O)N($R^b$)$_2$, -$L^1$-S—$R^b$, -$L^1$-S(O)$_2R^b$, -$L^1$-S(O)$R^b$, -$L^1$-SO$_2$N($R^a$)($R^b$), -$L^1$-N($R^a$)($R^b$), -$L^1$-N($R^b$)S(O)$_2R^b$, and -$L^1$-N($R^b$)C(O)O($R^b$); wherein $L^1$, $R^a$, and $R^b$ are as described herein.

In certain embodiments, $R^1$ is bicyclic aryl selected from the group consisting of 2,3-dihydro-1H-inden-1-yl, 1,2,3,4-tetrahydronaphthalen-1-yl, and 2,3-dihydro-1H-inden-2-yl.

In certain embodiments, $R^1$ is monocyclic heteroaryl; wherein the monocyclic heteroaryl is optionally substituted with 1, 2, 3, or 4 substituents selected from the group consisting of halogen, $C_1$-$C_6$-alkyl, $C_1$-$C_6$-haloalkyl, —OCH$_2$O—, —O—$R^b$, —CN, —N($R^b$)C(O)$R^b$, —CON($R^a$)($R^b$), —C(O)$R^b$, —OC(O)$R^b$, —OS(O)$_2$N($R^a$)($R^b$), —CO$_2$H, —CO$_2R^b$, —N($R^b$)C(O)N($R^b$)$_2$, —S—$R^b$, —S(O)$_2R^b$, —S(O)$R^b$, —SO$_2$N($R^a$)($R^b$), —N($R^a$)($R^b$), —N($R^b$)S(O)$_2R^b$, —N($R^b$)C(O)O($R^b$), —N($R^b$)S(O)$_2$O($R^b$), -$L^1$-O—$R^b$, -$L^1$-CN, -$L^1$-N($R^b$)C(O)$R^b$, -$L^1$-CON($R^a$)($R^b$), -$L^1$-C(O)$R^b$, -$L^1$-OC(O)$R^b$, -$L^1$-CO$_2$H, -$L^1$-CO$_2R^b$, -$L^1$-N($R^b$)C(O)N($R^b$)$_2$, -$L^1$-S—$R^b$, -$L^1$-S(O)$_2R^b$, -$L^1$-S(O)$R^b$, -$L^1$-SO$_2$N($R^a$)($R^b$), -$L^1$-N($R^a$)($R^b$), -$L^1$-N($R^b$)S(O)$_2R^b$, and -$L^1$-N($R^b$)C(O)O($R^b$); wherein $L^1$, $R^a$, and $R^b$ are as described herein.

In certain embodiments, $R^1$ is monocyclic heteroaryl; wherein the monocyclic heteroaryl is selected from the group consisting of pyrazolyl, pyridinyl, thiadiazolyl, and isoxazolyl optionally substituted with 1, 2, or 3 methyl.

In certain embodiments, $R^1$ is $C_3$-$C_8$-cycloalkyl-$C_1$-$C_6$-alkyl, phenyl-$C_1$-$C_6$-alkyl, heterocyclyl-$C_1$-$C_6$-alkyl, or monocyclic heteroaryl-$C_1$-$C_6$-alkyl; wherein the $C_3$-$C_8$-cycloalkyl of $C_3$-$C_8$-cycloalkyl-$C_1$-$C_6$-alkyl and heterocyclyl of heterocyclyl-$C_1$-$C_6$-alkyl are optionally substituted with 1, 2, 3, or 4 substituents selected from the group consisting of $C_1$-$C_{10}$-alkyl, $C_2$-$C_{10}$-alkenyl, $C_2$-$C_{10}$-alkynyl, $C_1$-$C_{10}$-haloalkyl, $C_2$-$C_{10}$-haloalkenyl, $C_2$-$C_{10}$-haloalkynyl, halogen, oxo, cyano, hydroxy, —O—$C_1$-$C_6$-alkyl, —O—$C_1$-$C_6$-haloalkyl, —$C_1$-$C_3$-alkylene-O—H, —$C_1$-$C_3$-alkylene-O—$C_1$-$C_6$-alkyl, —$C_1$-$C_3$-alkylene-O—$C_1$-$C_6$-haloalkyl, —$C_1$-$C_3$-alkylene-NH$_2$, —NH$_2$, —C(O)O—$C_1$-$C_6$-alkyl, —N($R^{b1}$)C(O)$R^{b1}$, —CON($R^{a1}$)($R^{b1}$), —C(O)$R^{b1}$, —OC(O)$R^{b1}$, —OS(O)$_2$N($R^{a1}$)($R^{b1}$), —CO$_2$H, —CO$_2R^{b1}$, —N($R^{b1}$)C(O)N($R^{b1}$)$_2$, —S—$R^{b1}$, —S(O)$_2R^{b1}$, —S(O)$R^{b1}$, —SO$_2$N($R^{a1}$)($R^{b1}$), —N($R^{a1}$)($R^{b1}$), —N($R^{b1}$)S(O)$_2R^{b1}$, —N($R^{b1}$)C(O)O($R^{b1}$), —N($R^{b1}$)S(O)$_2$O($R^{b1}$), -$L^{1a}$-O—$R^{b1}$, -$L^{1a}$-CN, -$L^{1a}$-N($R^{b1}$)C(O)$R^{b1}$, -$L^{1a}$-CON($R^{a1}$)($R^{b1}$), -$L^{1a}$-C(O)$R^{b1}$, -$L^{1a}$-OC(O)$R^{b1}$, -$L^{1a}$-CO$_2$H, -$L^{1a}$-CO$_2R^{b1}$, -$L^{1a}$-N($R^{b1}$)C(O)N($R^{b1}$)$_2$, -$L^{1a}$-S—$R^{b1}$, -$L^{1a}$-S(O)$_2R^{b1}$, -$L^{1a}$-S(O)$R^{b1}$, -$L^{1a}$-SO$_2$N($R^{a1}$)($R^{b1}$), -$L^{1a}$-N($R^{a1}$)($R^{b1}$), -$L^{1a}$-N($R^{b1}$)S(O)$_2R^{b1}$, and -$L^{1a}$-N($R^{b1}$)C(O)O($R^{b1}$); wherein the phenyl of phenyl-$C_1$-$C_6$-alkyl and monocyclic heteroaryl of monocyclic heteroaryl-$C_1$-$C_6$-alkyl are optionally substituted with 1, 2, 3, 4, or 5 substituents selected from the group consisting of halogen, $C_1$-$C_6$-alkyl, $C_1$-$C_6$-haloalkyl, —OCH$_2$O—, —O—$R^b$, —CN, —N($R^b$)C(O)$R^b$, —CON($R^a$)($R^b$), —C(O)$R^b$, —OC(O)$R^b$, —OS(O)$_2$N($R^a$)($R^b$), —CO$_2$H, —CO$_2R^b$, —N($R^b$)C(O)N($R^b$)$_2$, —S—$R^b$, —S(O)$_2R^b$, —S(O)$R^b$, —SO$_2$N($R^a$)($R^b$), —N($R^a$)($R^b$), —N(R$^b$)S(O)$_2$R$^b$, —N(R$^b$)C(O)O(R$^b$), —N(R$^b$)S(O)$_2$O(R$^b$), -L$^1$-O—R$^b$, -L$^1$-CN, -L$^1$-N(R$^b$)C(O)R$^b$, -L$^1$-CON(R$^a$)(R$^b$), -L$^1$-C(O)R$^b$, -L$^1$-OC(O)R$^b$, -L$^1$-CO$_2$H, -L$^1$-CO$_2$R$^b$, -L$^1$-N(R$^b$)C(O)N(R$^b$)$_2$, -L$^1$-S—R$^b$, -L$^1$-S(O)R$^b$-L$^1$-S(O)R$^b$, -L$^1$-SO$_2$N(R$^a$)(R$^b$), -L$^1$-N(R$^a$)(R$^b$), -L$^1$-N(R$^b$)S(O)$_2$R$^b$, and -L$^1$-N(R$^b$)C(O)O(R$^b$); wherein L$^1$, -L$^{1a}$, R$^a$, R$^{a1}$, R$^b$ and R$^{b1}$ are as described herein.

In certain embodiments, R$^1$ is C$_3$-C$_8$-cycloalkyl-C$_1$-C$_6$-alkyl or heterocyclyl-C$_1$-C$_6$-alkyl; wherein the C$_3$-C$_8$-cycloalkyl of C$_3$-C$_8$-cycloalkyl-C$_1$-C$_6$-alkyl and heterocyclyl of heterocyclyl-C$_1$-C$_6$-alkyl are optionally substituted with 1, 2, 3, or 4 substituents selected from the group consisting of C$_1$-C$_{10}$-alkyl, C$_2$-C$_{10}$-alkenyl, C$_2$-C$_{10}$-alkynyl, C$_1$-C$_{10}$-haloalkyl, C$_2$-C$_{10}$-haloalkenyl, C$_2$-C$_{10}$-haloalkynyl, halogen, oxo, cyano, hydroxy, —O—C$_1$-C$_6$-alkyl, —O—C$_1$-C$_6$-haloalkyl, —C$_1$-C$_3$-alkylene-O—H, —C$_1$-C$_3$-alkylene-O—C$_1$-C$_6$-alkyl, —C$_1$-C$_3$-alkylene-O—C$_1$-C$_6$-haloalkyl, —C$_1$-C$_3$-alkylene-NH$_2$, —NH$_2$, —C(O)O—C$_1$-C$_6$-alkyl, —N(R$^{b1}$)C(O)R$^{b1}$, —CON(R$^{a1}$)(R$^{b1}$), —C(O)R$^{b1}$, —OC(O)R$^{b1}$, —OS(O)$_2$N(R$^{a1}$)(R$^{b1}$), —CO$_2$H, —CO$_2$R$^{b1}$, —N(R$^{b1}$)C(O)N(R$^{b1}$)$_2$, —S—R$^{b1}$, —S(O)$_2$R$^{b1}$, —S(O)R$^{b1}$, —SO$_2$N(R$^{a1}$)(R$^{b1}$), —N(R$^{a1}$)(R$^{b1}$), —N(R$^{b1}$)S(O)$_2$R$^{b1}$, —N(R$^{b1}$)C(O)O(R$^{b1}$), —N(R$^{b1}$)S(O)$_2$O(R$^{b1}$), -L$^{1a}$-O—R$^{b1}$, -L$^{1a}$-CN, -L$^{1a}$-N(R$^{b1}$)C(O)R$^{b1}$, -L$^{1a}$-CON(R$^{a1}$)(R$^{b1}$), -L$^{1a}$-C(O)R$^{b1}$, -L$^{1a}$-OC(O)R$^{b1}$, -L$^{1a}$-CO$_2$H, -L$^{1a}$-CO$_2$R$^{b1}$, -L$^{1a}$-N(R$^{b1}$)C(O)N(R$^{b1}$)$_2$, -L$^{1a}$-S—R$^{b1}$, -L$^{1a}$-S(O)$_2$R$^{b1}$, -L$^{1a}$-S(O)R$^{b1}$, -L$^{1a}$-SO$_2$N(R$^{a1}$)(R$^{b1}$), -L$^{1a}$-N(R$^{a1}$)(R$^{b1}$), -L$^{1a}$-N(R$^{b1}$)S(O)$_2$R$^{b1}$, and -L$^{1a}$-N(R$^{b1}$)C(O)O(R$^{b1}$); wherein L$^{1a}$, R$^{a1}$, and R$^{b1}$ are as described herein.

In certain embodiments, R$^1$ is C$_3$-C$_8$-cycloalkyl-C$_1$-C$_6$-alkyl or heterocyclyl-C$_1$-C$_6$-alkyl; wherein the C$_3$-C$_8$-cycloalkyl-C$_1$-C$_6$-alkyl and heterocyclyl-C$_1$-C$_6$-alkyl are selected from the group consisting of cyclopentylmethyl, cyclohexylmethyl and tetrahydrofuranylmethyl.

In certain embodiments, R$^1$ is phenyl-C$_1$-C$_6$-alkyl or monocyclic heteroaryl-C$_1$-C$_6$-alkyl; wherein the phenyl of phenyl-C$_1$-C$_6$-alkyl and monocyclic heteroaryl of monocyclic heteroaryl-C$_1$-C$_6$-alkyl are optionally substituted with 1, 2, 3, 4, or 5 substituents selected from the group consisting of halogen, C$_1$-C$_6$-alkyl, C$_1$-C$_6$-haloalkyl, —OCH$_2$O—, —O—R$^b$, —CN, —N(R$^b$)C(O)R$^b$, —CON(R$^a$)(R$^b$), —C(O)R$^b$, —OC(O)R$^b$, —OS(O)$_2$N(R$^a$)(R$^b$), —CO$_2$H, —CO$_2$R$^b$, —N(R$^b$)C(O)N(R$^b$)$_2$, —S—R$^b$, —S(O)$_2$R$^b$, —S(O)R$^b$, —SO$_2$N(R$^a$)(R$^b$), —N(R$^a$)(R$^b$), —N(R$^b$)S(O)$_2$R$^b$, —N(R$^b$)C(O)O(R$^b$), —N(R$^b$)S(O)$_2$O(R$^b$), -L$^1$-O—R$^b$, -L$^1$-CN, -L$^1$-N(R$^b$)C(O)R$^b$, -L$^1$-CON(R$^a$)(R$^b$), -L$^1$-C(O)R$^b$, -L$^1$-OC(O)R$^b$, -L$^1$-CO$_2$H, -L$^1$-CO$_2$R$^b$, -L$^1$-N(R$^b$)C(O)N(R$^b$)$_2$, -L$^1$-S—R$^b$, -L$^1$-S(O)$_2$R$^b$, -L$^1$-S(O)R$^b$, -L$^1$-SO$_2$N(R$^a$)(R$^b$), -L$^1$-N(R$^a$)(R$^b$), -L$^1$-N(R$^b$)S(O)$_2$R$^b$, and -L$^1$-N(R$^b$)C(O)O(R$^b$); wherein L$^1$, R$^a$, and R$^b$ are as described herein.

In certain embodiments, R$^1$ is phenyl-C$_1$-C$_6$-alkyl; wherein the phenyl-C$_1$-C$_6$-alkyl is benzyl; wherein the phenyl of phenyl-C$_1$-C$_6$-alkyl is optionally substituted with halogen or C$_1$-C$_6$-alkyl.

In certain embodiments, R$^2$ is methyl or ethyl.
In certain embodiments, R$^2$ is methyl.
In certain embodiments, R$^2$ is ethyl.
In certain embodiments, R$^3$ is methyl or ethyl.
In certain embodiments, R$^3$ is methyl.
In certain embodiments, R$^3$ is ethyl.
In certain embodiments, R$^2$ is methyl and R$^3$ is methyl.
In certain embodiments, R$^2$ is methyl and R$^3$ is ethyl.
In certain embodiments, R$^2$ is ethyl and R$^3$ is methyl.
In certain embodiments, R$^2$ is ethyl and R$^3$ is ethyl.
In certain embodiments, R$^4$ and R$^5$ are independently selected from hydrogen, C$_1$-C$_6$-alkyl, or C$_1$-C$_6$-haloalkyl.

In certain embodiments, R$^4$ and R$^5$ are each hydrogen.
In certain embodiments, R$^4$ and R$^5$ are independently selected from C$_1$-C$_6$-alkyl or C$_1$-C$_6$-haloalkyl.
In certain embodiments, R$^4$ is hydrogen and R$^5$ is selected from C$_1$-C$_6$-alkyl or C$_1$-C$_6$-haloalkyl.
In certain embodiments, R$^6$ is selected from the group consisting of hydrogen, C$_1$-C$_6$-alkyl, and C$_1$-C$_6$-haloalkyl.
In certain embodiments, R$^6$ is hydrogen.
In certain embodiments, R$^6$ is C$_1$-C$_6$-alkyl.
In certain embodiments, R$^6$ is C$_1$-C$_6$-haloalkyl.

In certain embodiments, G$^1$ is phenyl or monocyclic heteroaryl, wherein the phenyl or monocyclic heteroaryl are optionally substituted with 1, 2, 3, 4, or 5 substituents selected from the group consisting of halogen, C$_1$-C$_6$-alkyl, C$_1$-C$_6$-haloalkyl, —O—R$^f$, —CN, —N(R$^f$)C(O)R$^f$, —CON(R$^e$)(R$^f$), —C(O)R$^f$, —OC(O)R$^f$, —CO$_2$H, —CO$_2$R$^f$, —N(R$^f$)C(O)N(R$^f$)$_2$, —S—R$^f$, —S(O)$_2$R$^f$, —S(O)R$^f$, —SO$_2$N(R$^e$)(R$^f$), —N(R$^e$)(R$^f$), —N(R$^f$)S(O)$_2$R$^f$, —N(R$^f$)C(O)O(R$^f$), -L$^3$-O—R$^f$, -L$^3$-CN, -L$^3$-N(R$^f$)C(O)R$^f$, -L$^3$-CON(R$^e$)(R$^f$), -L$^3$-C(O)R$^f$, -L$^3$-OC(O)R$^f$, -L$^3$-CO$_2$H, -L$^3$-CO$_2$R$^f$, -L$^3$-N(R$^f$)C(O)N(R$^f$)$_2$, -L$^3$-S—R$^f$, -L$^3$-S(O)$_2$R$^f$, -L$^3$-S(O)R$^f$, -L$^3$-SO$_2$N(R$^e$)(R$^f$), -L$^3$-N(R$^e$)(R$^f$), -L$^3$-N(R$^f$)S(O)$_2$R$^f$, and -L$^3$-N(R$^f$)C(O)O(R$^f$); wherein L$^3$, R$^e$ and R$^f$ are as described herein.

In certain embodiments, G$^1$ is phenyl, wherein the phenyl is optionally substituted with 1, 2, 3, 4, or 5 substituents selected from the group consisting of halogen, C$_1$-C$_6$-alkyl, C$_1$-C$_6$-haloalkyl, —O—R$^f$, —CN, —N(R$^f$)C(O)R$^f$, —CON(R$^e$)(R$^f$), —C(O)R$^f$, —OC(O)R$^f$, —CO$_2$H, —CO$_2$R$^f$, —N(R$^f$)C(O)N(R$^f$)$_2$, —S—R$^f$, —S(O)$_2$R$^f$, —S(O)R$^f$, —SO$_2$N(R$^e$)(R$^f$), —N(R$^e$)(R$^f$), —N(R$^f$)S(O)$_2$R$^f$, —N(R$^f$)C(O)O(R$^f$), -L$^3$- O—R$^f$, -L$^3$-CN, -L$^3$-N(R$^f$)C(O)R$^f$, -L$^3$-CON(R$^e$)(R$^f$), -L$^3$-C(O)R$^f$, -L$^3$-OC(O)R$^f$, -L$^3$-CO$_2$H, -L$^3$-CO$_2$R$^f$, -L$^3$-N(R$^f$)C(O)N(R$^f$)$_2$, -L$^3$-S—R$^f$, -L$^3$-S(O)$_2$R$^f$, -L$^3$-S(O)R$^f$, -L$^3$-SO$_2$N(R$^e$)(R$^f$), -L$^3$-N(R$^e$)(R$^f$), -L$^3$-N(R$^f$)S(O)$_2$R$^f$, and -L$^3$-N(R$^f$)C(O)O(R$^f$); wherein L$^3$, R$^e$ and R$^f$ are as described herein.

In certain embodiments, G$^1$ is phenyl, wherein the phenyl is optionally substituted with 1, 2, 3, 4, or 5 substituents selected from the group consisting of halogen, C$_1$-C$_6$-alkyl, C$_1$-C$_6$-haloalkyl or —O—R$^f$; wherein R$^f$ is as described in the Summary.

In certain embodiments, G$^1$ is monocyclic heteroaryl, wherein the monocyclic heteroaryl is optionally substituted with 1, 2, 3, 4, or 5 substituents selected from the group consisting of halogen, C$_1$-C$_6$-alkyl, C$_1$-C$_6$-haloalkyl, —O—R$^f$, —CN, —N(R$^f$)C(O)R$^f$, —CON(R$^e$)(R$^f$), —C(O)R$^f$, —OC(O)R$^f$, —CO$_2$H, —CO$_2$R$^f$, —N(R$^f$)C(O)N(R$^f$)$_2$, —S—R$^f$, —S(O)$_2$R$^f$, —S(O)R$^f$, —SO$_2$N(R$^e$)(R$^f$), —N(R$^e$)(R$^f$), —N(R$^f$)S(O)$_2$R$^f$, —N(R$^f$)C(O)O(R$^f$), -L$^3$-O—R$^f$, -L$^3$-CN, -L$^3$-N(R$^f$)C(O)R$^f$, -L$^3$-CON(R$^e$)(R$^f$), -L$^3$-C(O)R$^f$, -L$^3$-OC(O)R$^f$, -L$^3$-CO$_2$H, -L$^3$-CO$_2$R$^f$, -L$^3$-N(R$^f$)C(O)N(R$^f$)$_2$, -L$^3$-S—R$^f$, -L$^3$-S(O)$_2$R$^f$, -L$^3$-S(O)R$^f$, -L$^3$-SO$_2$N(R$^e$)(R$^f$), -L$^3$-N(R$^e$)(R$^f$), -L$^3$-N(R$^f$)S(O)$_2$R$^f$, and -L$^3$-N(R$^f$)C(O)O(R$^f$); wherein L$^3$, R$^e$ and R$^f$ are as described herein.

In certain embodiments, G$^1$ is monocyclic heteroaryl; wherein the monocyclic heteroaryl is selected from the group consisting of pyridyl, pyrazolyl, imidazolyl, isoxazolyl, and thienyl; wherein the monocyclic heteroaryl is optionally substituted with 1, 2, 3, or 4 substituents selected from the group consisting of halogen, C$_1$-C$_6$-alkyl, C$_1$-C$_6$-haloalkyl or —O—R$^f$; wherein R$^f$ is as described in the Summary.

In certain embodiments, X is selected from O, S, NR$^g$, or C(R$^h$R$^i$).

In certain embodiments, X is O or S.

In certain embodiments, X is NR$^g$; wherein R$^g$ is hydrogen or $C_1$-$C_6$-alkyl.

In certain embodiments, X is NR$^g$; wherein R$^g$ is hydrogen.

In certain embodiments, X is NR$^g$; wherein R$^g$ is $C_1$-$C_6$-alkyl.

In certain embodiments, X is C(R$^h$R$^i$); wherein R$^h$ and R$^i$ are independently hydrogen, $C_1$-$C_6$-alkyl, or $C_1$-$C_6$-haloalkyl.

In certain embodiments, X is C(R$^h$R$^i$); wherein R$^h$ and R$^i$ are each hydrogen.

In certain embodiments, X is C(R$^h$R$^i$); wherein R$^h$ is hydrogen and R$^i$ is $C_1$-$C_6$-alkyl, or $C_1$-$C_6$-haloalkyl.

In certain embodiments, X is C(R$^h$R$^i$); wherein R$^h$ and R$^i$ are independently $C_1$-$C_6$-alkyl or $C_1$-$C_6$-haloalkyl.

In one aspect of the disclosure are compounds of formula (I) wherein:

R$^1$ is $C_1$-$C_6$-alkyl, $C_1$-$C_6$-haloalkyl, $C_3$-$C_8$-cycloalkyl, $C_3$-$C_8$-cycloalkyl-$C_1$-$C_6$-alkyl, phenyl, bicyclic aryl, phenyl-$C_1$-$C_6$-alkyl, heterocyclyl, heterocyclyl-$C_1$-$C_6$-alkyl, monocyclic heteroaryl, or monocyclic heteroaryl-$C_1$-$C_6$-alkyl; wherein the $C_3$-$C_8$-cycloalkyl, the $C_3$-$C_8$-cycloalkyl of $C_3$-$C_8$-cycloalkyl-$C_1$-$C_6$-alkyl, heterocyclyl, and heterocyclyl of heterocyclyl-$C_1$-$C_6$-alkyl are optionally substituted with 1, 2, 3, or 4 substituents selected from the group consisting of $C_1$-$C_{10}$-alkyl, $C_2$-$C_{10}$-alkenyl, $C_2$-$C_{10}$-alkynyl, $C_1$-$C_{10}$-haloalkyl, $C_2$-$C_{10}$-haloalkenyl, $C_2$-$C_{10}$-haloalkynyl, halogen, oxo, cyano, hydroxy, —O—$C_1$-$C_6$-alkyl, —O—$C_1$-$C_6$-haloalkyl, —$C_1$-$C_3$-alkylene-O—H, —$C_1$-$C_3$-alkylene-O—$C_1$-$C_6$-alkyl, —$C_1$-$C_3$-alkylene-O—$C_1$-$C_6$-haloalkyl, —$C_1$-$C_3$-alkylene-NH$_2$, —NH$_2$, —C(O)O—$C_1$-$C_6$-alkyl, —N(R$^{b1}$)C(O)R$^{b1}$, —CON(R$^{a1}$)(R$^{b1}$), —C(O)R$^{b1}$, —OC(O)R$^{b1}$, —OS(O)$_2$N(R$^{a1}$)(R$^{b1}$), —CO$_2$H, —CO$_2$R$^{b1}$, —N(R$^{b1}$)C(O)N(R$^{b1}$)$_2$, —S—R$^{b1}$, —S(O)$_2$R$^{b1}$, —S(O)R$^{b1}$, —SO$_2$N(R$^{a1}$)(R$^{b1}$), —N(R$^{a1}$)(R$^{b1}$), —N(R$^{b1}$)S(O)$_2$R$^{b1}$, —N(R$^{b1}$)C(O)O(R$^{b1}$), —N(R$^{b1}$)S(O)$_2$O(R$^{b1}$), -L$^{1a}$-O—R$^{b1}$, -L$^{1a}$-CN, -L$^{1a}$-N(R$^{b1}$)C(O)R$^{b1}$, -L$^{1a}$-CON(R$^{a1}$)(R$^{b1}$), -L$^{1a}$-C(O)R$^{b1}$, -L$^{1a}$-OC(O)R$^{b1}$, -L$^{1a}$-CO$_2$H, -L$^{1a}$-CO$_2$R$^{b1}$, -L$^{1a}$-N(R$^{b1}$)C(O)N(R$^{b1}$)$_2$, -L$^{1a}$-S—R$^{b1}$, -L$^{1a}$-S(O)$_2$R$^{b1}$, -L$^{1a}$-S(O)R$^{b1}$, -L$^{1a}$-SO$_2$N(R$^{a1}$)(R$^{b1}$), -L$^{1a}$-N(R$^{a1}$)(R$^{b1}$), -L$^{1a}$-N(R$^{b1}$)S(O)$_2$R$^{b1}$ and -L$^{1a}$-N(R$^{b1}$)C(O)O(R$^{b1}$); wherein the phenyl, the bicyclic aryl, the phenyl of phenyl-$C_1$-$C_6$-alkyl, the monocyclic heteroaryl and monocyclic heteroaryl of monocyclic heteroaryl-$C_1$-$C_6$-alkyl are optionally substituted with 1, 2, 3, 4, or 5 substituents selected from the group consisting of halogen, $C_1$-$C_6$-alkyl, $C_1$-$C_6$-haloalkyl, —OCH$_2$O—, —O—R$^b$, —CN, —N(R$^b$)C(O)R$^b$, —CON(R$^a$)(R$^b$), —C(O)R$^b$, —OC(O)R$^b$, —OS(O)$_2$N(R$^a$)(R$^b$), —CO$_2$H, —CO$_2$R$^b$, —N(R$^b$)C(O)N(R$^b$)$_2$, —S—R$^b$, —S(O)$_2$R$^b$, —S(O)R$^b$, —SO$_2$N(R$^a$)(R$^b$), —N(R$^a$)(R$^b$), —N(R$^b$)S(O)$_2$R$^b$, —N(R$^b$)C(O)O(R$^b$), —N(R$^b$)S(O)$_2$O(R$^b$), -L$^1$-O—R$^b$, -L$^1$- CN, -L$^1$-N(R$^b$)C(O)R$^b$, -L$^1$-CON(R$^a$)(R$^b$), -L$^1$-C(O)R$^b$, -L$^1$-OC(O)R$^b$, -L$^1$-CO$_2$H, -L$^1$-CO$_2$R$^b$, -L$^1$-N(R$^b$)C(O)N(R$^b$)$_2$, -L$^1$-S—R$^b$, -L$^1$-S(O)$_2$R$^b$, -L$^1$-S(O)R$^b$, -L$^1$-SO$_2$N(R$^a$)(R$^b$), -L$^1$-N(R$^a$)(R$^b$), -L$^1$-N(R$^b$)S(O)$_2$R$^b$, and -L$^1$-N(R$^b$)C(O)O(R$^b$);

R$^2$ is methyl or ethyl;

R$^3$ is methyl or ethyl;

R$^4$ and R$^5$ are independently selected from the group consisting of hydrogen, $C_1$-$C_6$-alkyl, and $C_1$-$C_6$-haloalkyl;

R$^6$ is selected from the group consisting of hydrogen, $C_1$-$C_6$-alkyl, and $C_1$-$C_6$-haloalkyl;

G$^1$ is phenyl or monocyclic heteroaryl, wherein the phenyl or monocyclic heteroaryl are optionally substituted with 1, 2, 3, 4, or 5 substituents selected from the group consisting of halogen, $C_1$-$C_6$-alkyl, $C_1$-$C_6$-haloalkyl, —O—R$^f$, —CN, —N(R$^f$)C(O)R$^f$, —CON(R$^e$)(R$^f$), —C(O)R$^f$, —OC(O)R$^f$, —CO$_2$H, —CO$_2$R$^f$, —N(R$^f$)C(O)N(R$^f$)$_2$, —S—R$^f$, —S(O)$_2$R$^f$, —S(O)R$^f$, —SO$_2$N(R$^e$)(R$^f$), —N(R$^e$)(R$^f$), —N(R$^f$)S(O)$_2$R$^f$, —N(R$^f$)C(O)O(R$^f$), -L$^3$-O—R$^f$, -L$^3$-CN, -L$^3$-N(R$^f$)C(O)R$^f$, -L$^3$-CON(R$^e$)(R$^f$), -L$^3$-C(O)R$^f$, -L$^3$-OC(O)R$^f$, -L$^3$-CO$_2$H, -L$^3$-CO$_2$R$^f$, -L$^3$-N(R$^f$)C(O)N(R$^f$)$_2$, -L$^3$-S—R$^f$, -L$^3$-S(O)$_2$R$^f$, -L$^3$-S(O)R$^f$, -L$^3$-SO$_2$N(R$^e$)(R$^f$), -L$^3$-N(R$^e$)(R$^f$), -L$^3$-N(R$^f$)S(O)$_2$R$^f$, and -L$^3$-N(R$^f$)C(O)O(R$^f$); and X is selected from O or S; wherein L$^1$, L$^{1a}$, L$^3$, R$^a$, R$^{a1}$, R$^b$, R$^{b1}$, R$^e$, and R$^f$ are as described herein.

In one aspect of the disclosure are compounds of formula (I) wherein:

R$^1$ is $C_1$-$C_6$-alkyl, $C_1$-$C_6$-haloalkyl, $C_3$-$C_8$-cycloalkyl, $C_3$-$C_8$-cycloalkyl-$C_1$-$C_6$-alkyl, phenyl, bicyclic aryl, phenyl-$C_1$-$C_6$-alkyl, heterocyclyl, heterocyclyl-$C_1$-$C_6$-alkyl, monocyclic heteroaryl, or monocyclic heteroaryl-$C_1$-$C_6$-alkyl; wherein the $C_3$-$C_8$-cycloalkyl, the $C_3$-$C_8$-cycloalkyl of $C_3$-$C_8$-cycloalkyl-$C_1$-$C_6$-alkyl, heterocyclyl, and heterocyclyl of heterocyclyl-$C_1$-$C_6$-alkyl are optionally substituted with 1, 2, 3, or 4 substituents selected from the group consisting of $C_1$-$C_{10}$-alkyl, $C_2$-$C_{10}$-alkenyl, $C_2$-$C_{10}$-alkynyl, $C_1$-$C_{10}$-haloalkyl, $C_2$-$C_{10}$-haloalkenyl, $C_2$-$C_{10}$-haloalkynyl, halogen, oxo, cyano, hydroxy, —O—$C_1$-$C_6$-alkyl, —O—$C_1$-$C_6$-haloalkyl, —$C_1$-$C_3$-alkylene-O—H, —$C_1$-$C_3$-alkylene-O—$C_1$-$C_6$-alkyl, —$C_1$-$C_3$-alkylene-O—$C_1$-$C_6$-haloalkyl, —$C_1$-$C_3$-alkylene-NH$_2$, —NH$_2$, —C(O)O—$C_1$-$C_6$-alkyl, —N(R$^{b1}$)C(O)R$^{b1}$, —CON(R$^{a1}$)(R$^{b1}$), —C(O)R$^{b1}$, —OC(O)R$^{b1}$, —OS(O)$_2$N(R$^{a1}$)(R$^{b1}$), —CO$_2$H, —CO$_2$R$^{b1}$, —N(R$^{b1}$)C(O)N(R$^{b1}$)$_2$, —S—R$^{b1}$, —S(O)$_2$R$^{b1}$, —S(O)R$^{b1}$, —SO$_2$N(R$^{a1}$)(R$^{b1}$), —N(R$^{a1}$)(R$^{b1}$), —N(R$^{b1}$)S(O)$_2$R$^{b1}$, —N(R$^{b1}$)C(O)O(R$^{b1}$), —N(R$^{b1}$)S(O)$_2$O(R$^{b1}$), -L$^{1a}$-O—R$^{b1}$, -L$^{1a}$-CN, -L$^{1a}$-N(R$^{b1}$)C(O)R$^{b1}$, -L$^{1a}$-CON(R$^{a1}$)(R$^{b1}$), -L$^{1a}$-C(O)R$^{b1}$, -L$^{1a}$-OC(O)R$^{b1}$, -L$^{1a}$-CO$_2$H, -L$^{1a}$-CO$_2$R$^{b1}$, -L$^{1a}$-N(R$^{b1}$)C(O)N(R$^{b1}$)$_2$, -L$^{1a}$-S—R$^{b1}$, -L$^{1a}$-S(O)$_2$R$^{b1}$, -L$^{1a}$-S(O)R$^{b1}$, -L$^{1a}$-SO$_2$N(R$^{a1}$)(R$^{b1}$), -L$^{1a}$-N(R$^{a1}$)(R$^{b1}$), -L$^{1a}$-N(R$^{b1}$)S(O)$_2$R$^{b1}$, and -L$^{1a}$-N(R$^{b1}$)C(O)O(R$^{b1}$); wherein the phenyl, the bicyclic aryl, the phenyl of phenyl-$C_1$-$C_6$-alkyl, the monocyclic heteroaryl and monocyclic heteroaryl of monocyclic heteroaryl-$C_1$-$C_6$-alkyl are optionally substituted with 1, 2, 3, 4, or 5 substituents selected from the group consisting of halogen, $C_1$-$C_6$-alkyl, $C_1$-$C_6$-haloalkyl, —OCH$_2$O—, —O—R$^b$, —CN, —N(R$^b$)C(O)R$^b$, —CON(R$^a$)(R$^b$), —C(O)R$^b$, —OC(O)R$^b$, —OS(O)$_2$N(R$^a$)(R$^b$), —CO$_2$H, —CO$_2$R$^b$, —N(R$^b$)C(O)N(R$^b$)$_2$, —S—R$^b$, —S(O)$_2$R$^b$, —S(O)R$^b$, —SO$_2$N(R$^a$)(R$^b$), —N(R$^a$)(R$^b$), —N(R$^b$)S(O)$_2$R$^b$, —N(R$^b$)C(O)O(R$^b$), —N(R$^b$)S(O)$_2$O(R$^b$), -L$^1$-O—R$^b$, -L$^1$- CN, -L$^1$-N(R$^b$)C(O)R$^b$, -L$^1$-CON(R$^a$)(R$^b$), -L$^1$-C(O)R$^b$, -L$^1$-OC(O)R$^b$, -L$^1$-CO$_2$H, -L$^1$-CO$_2$R$^b$, -L$^1$-N(R$^b$)C(O)N(R$^b$)$_2$, -L$^1$-S—R$^b$, -L$^1$-S(O)$_2$R$^b$, -L$^1$-S(O)R$^b$, -L$^1$-SO$_2$N(R$^a$)(R$^b$), -L$^1$-N(R$^a$)(R$^b$), -L$^1$-N(R$^b$)S(O)$_2$R$^b$, and -L$^1$-N(R$^b$)C(O)O(R$^b$);

R$^2$ is methyl or ethyl;

R$^3$ is methyl or ethyl;

R$^4$ and R$^5$ are independently selected from the group consisting of hydrogen, $C_1$-$C_6$-alkyl, and $C_1$-$C_6$-haloalkyl;

R$^6$ is selected from the group consisting of hydrogen, $C_1$-$C_6$-alkyl, and $C_1$-$C_6$-haloalkyl;

G$^1$ is phenyl or monocyclic heteroaryl, wherein the phenyl or monocyclic heteroaryl are optionally substituted with 1, 2, 3, 4, or 5 substituents selected from the group consisting of halogen, $C_1$-$C_6$-alkyl, $C_1$-$C_6$-haloalkyl, —O—R$^f$, —CN, —N(R$^f$)C(O)R$^f$, —CON(R$^e$)(R$^f$), —C(O)R$^f$, —OC(O)R$^f$, —CO$_2$H, —CO$_2$R$^f$, —N(R$^f$)C(O)N(R$^f$)$_2$, —S—R$^f$, —S(O)$_2$R$^f$, —S(O)R$^f$, —SO$_2$N(R$^e$)(R$^f$), —N(R$^e$)(R$^f$), —N(R$^f$)S(O)$_2$R$^f$, —N(R$^f$)C(O)O(R$^f$), -L$^3$-O—R$^f$, -L$^3$-CN, -L$^3$-N(R$^f$)C(O)R$^f$, -L$^3$-CON(R$^e$)(R$^f$), -L$^3$-C(O)R$^f$, -L$^3$-OC(O)R$^f$, -L$^3$-CO$_2$H, -L$^3$-CO$_2$R$^f$, -L$^3$-N(R$^f$)C(O)N(R$^f$)$_2$, -L$^3$-

S—$R^f$, -$L^3$-S(O)$_2R^f$, -$L^3$-S(O)$R^f$, -$L^3$-SO$_2$N($R^e$)($R^f$), -$L^3$-N($R^e$)($R^f$), -$L^3$-N($R^f$)S(O)$_2R^f$, and -$L^3$-N($R^f$)C(O)O($R^f$); and X is C($R^hR^i$); wherein $L^1$, $L^{1a}$, $L^3$, $R^a$, $R^{a1}$, $R^b$, $R^{b1}$, $R^e$, $R^f$, $R^h$ and $R^i$ are as described herein.

In one aspect of the disclosure are compounds of formula (I) wherein:

$R^1$ is $C_1$-$C_6$-alkyl, $C_1$-$C_6$-haloalkyl, $C_3$-$C_8$-cycloalkyl, $C_3$-$C_8$-cycloalkyl-$C_1$-$C_6$-alkyl, phenyl, bicyclic aryl, phenyl-$C_1$-$C_6$-alkyl, heterocyclyl, heterocyclyl-$C_1$-$C_6$-alkyl, monocyclic heteroaryl, or monocyclic heteroaryl-$C_1$-$C_6$-alkyl; wherein the $C_3$-$C_8$-cycloalkyl, the $C_3$-$C_8$-cycloalkyl of $C_3$-$C_8$-cycloalkyl-$C_1$-$C_6$-alkyl, heterocyclyl, and heterocyclyl of heterocyclyl-$C_1$-$C_6$-alkyl are optionally substituted with 1, 2, 3, or 4 substituents selected from the group consisting of $C_1$-$C_{10}$-alkyl, $C_2$-$C_{10}$-alkenyl, $C_2$-$C_{10}$-alkynyl, $C_1$-$C_{10}$-haloalkyl, $C_2$-$C_{10}$-haloalkenyl, $C_2$-$C_{10}$-haloalkynyl, halogen, oxo, cyano, hydroxy, —O—$C_1$-$C_6$-alkyl, —O—$C_1$-$C_6$-haloalkyl, —$C_1$-$C_3$-alkylene-O—H, —$C_1$-$C_3$-alkylene-O—$C_1$-$C_6$-alkyl, —$C_1$-$C_3$-alkylene-O—$C_1$-$C_6$-haloalkyl, —$C_1$-$C_3$-alkylene-NH$_2$, —NH$_2$, —C(O)O—$C_1$-$C_6$-alkyl, —N($R^{b1}$)C(O)$R^{b1}$, —CON($R^{a1}$)($R^{b1}$), —C(O)$R^{b1}$, —OC(O)$R^{b1}$, —OS(O)$_2$N($R^{a1}$)($R^{b1}$), —CO$_2$H, —CO$_2R^{b1}$, —N($R^{b1}$)C(O)N($R^{b1}$)$_2$, —S—$R^{b1}$, —S(O)$_2R^{b1}$, —S(O)$R^{b1}$, —SO$_2$N($R^{a1}$)($R^{b1}$), —N($R^{a1}$)($R^{b1}$), —N($R^{b1}$)S(O)$_2R^{b1}$, —N($R^{b1}$)C(O)O($R^{b1}$), —N($R^{b1}$)S(O)$_2$O($R^{b1}$), -$L^{1a}$-O—$R^{b1}$, -$L^{1a}$-CN, -$L^{1a}$-N($R^{b1}$)C(O)$R^{b1}$, -$L^{1a}$-CON($R^{a1}$)($R^{b1}$), -$L^{1a}$-C(O)$R^{b1}$, -$L^{1a}$-OC(O)$R^{b1}$, -$L^{1a}$-CO$_2$H, -$L^{1a}$-CO$_2R^{b1}$, -$L^{1a}$-N($R^{b1}$)C(O)N($R^{b1}$)$_2$, -$L^{1a}$-S—$R^{b1}$, -$L^{1a}$-S(O)$_2R^{b1}$, -$L^{1a}$-S(O)$R^{b1}$, -$L^{1a}$-SO$_2$N($R^{a1}$)($R^{b1}$), -$L^{1a}$-N($R^{a1}$)($R^{b1}$), -$L^{1a}$-N($R^{b1}$)S(O)$_2R^{b1}$ and -$L^{1a}$-N($R^{b1}$)C(O)O($R^{b1}$); wherein the phenyl, the bicyclic aryl, the phenyl of phenyl-$C_1$-$C_6$-alkyl, the monocyclic heteroaryl and monocyclic heteroaryl of monocyclic heteroaryl-$C_1$-$C_6$-alkyl are optionally substituted with 1, 2, 3, 4, or 5 substituents selected from the group consisting of halogen, $C_1$-$C_6$-alkyl, $C_1$-$C_6$-haloalkyl, —OCH$_2$O—, —O—$R^b$, —CN, —N($R^b$)C(O)$R^b$, —CON($R^a$)($R^b$), —C(O)$R^b$, —OC(O)$R^b$, —OS(O)$_2$N($R^a$)($R^b$), —CO$_2$H, —CO$_2R^b$, —N($R^b$)C(O)N($R^b$)$_2$, —S—$R^b$, —S(O)$_2R^b$, —S(O)$R^b$, —SO$_2$N($R^a$)($R^b$), —N($R^a$)($R^b$), —N($R^b$)S(O)$_2R^b$, —N($R^b$)C(O)O($R^b$), —N($R^b$)S(O)$_2$O($R^b$), -$L^1$-O—$R^b$, -$L^1$-CN, -$L^1$-N($R^b$)C(O)$R^b$, -$L^1$-CON($R^a$)($R^b$), -$L^1$-C(O)$R^b$, -$L^1$-OC(O)$R^b$, -$L^1$-CO$_2$H, -$L^1$-CO$_2R^b$, -$L^1$-N($R^b$)C(O)N($R^b$)$_2$, -$L^1$-S—$R^b$, -$L^1$-S(O)$_2R^b$, -$L^1$-S(O)$R^b$, -$L^1$-SO$_2$N($R^a$)($R^b$), -$L^1$-N($R^a$)($R^b$), -$L^1$-N($R^b$)S(O)$_2R^b$, and -$L^1$-N($R^b$)C(O)O($R^b$);

$R^2$ is methyl or ethyl;

$R^3$ is methyl or ethyl;

$R^4$ and $R^5$ are independently selected from the group consisting of hydrogen, $C_1$-$C_6$-alkyl, and $C_1$-$C_6$-haloalkyl;

$R^6$ is selected from the group consisting of hydrogen, $C_1$-$C_6$-alkyl, and $C_1$-$C_6$-haloalkyl;

$G^1$ is phenyl or monocyclic heteroaryl, wherein the phenyl or monocyclic heteroaryl are optionally substituted with 1, 2, 3, 4, or 5 substituents selected from the group consisting of halogen, $C_1$-$C_6$-alkyl, $C_1$-$C_6$-haloalkyl, —O—$R^f$, —CN, —N($R^f$)C(O)$R^f$, —CON($R^e$)($R^f$), —C(O)$R^f$, —OC(O)$R^f$, —CO$_2$H, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, —N($R^f$)C(O)O($R^f$), -$L^3$-O—$R^f$, -$L^3$-CN, -$L^3$-N($R^f$)C(O)$R^f$, -$L^3$-CON($R^e$)($R^f$), -$L^3$-C(O)$R^f$, -$L^3$-OC(O)$R^f$, -$L^3$-CO$_2$H, -$L^3$-CO$_2R^f$, -$L^3$-N($R^f$)C(O)N($R^f$)$_2$, -$L^3$-S—$R^f$, -$L^3$-S(O)$_2R^f$, -$L^3$-S(O)$R^f$, -$L^3$-SO$_2$N($R^e$)($R^f$), -$L^3$-N($R^e$)($R^f$), -$L^3$-N($R^f$)S(O)$_2R^f$, and -$L^3$-N($R^f$)C(O)O($R^f$); and X is NR$^g$; wherein $L^{1a}$, $L^3$, $R^{a1}$, $R^{b1}$, $R^e$, $R^f$ and $R^g$ are as described herein.

In one particular subgroup, the present disclosure features compounds of formula (I), wherein $R^1$ is $C_1$-$C_6$-alkyl, $C_1$-$C_6$-haloalkyl, $C_3$-$C_8$-cycloalkyl, or heterocyclyl; wherein the $C_3$-$C_8$-cycloalkyl and heterocyclyl are optionally substituted with 1, 2, 3, or 4 substituents selected from the group consisting of $C_1$-$C_{10}$-alkyl, $C_2$-$C_{10}$-alkenyl, $C_2$-$C_{10}$-alkynyl, $C_1$-$C_{10}$-haloalkyl, $C_2$-$C_{10}$-haloalkenyl, $C_2$-$C_{10}$-haloalkynyl, halogen, oxo, cyano, hydroxy, —O—$C_1$-$C_6$-alkyl, —O—$C_1$-$C_6$-haloalkyl, —$C_1$-$C_3$-alkylene-O—H, —$C_1$-$C_3$-alkylene-O—$C_1$-$C_6$-alkyl, —$C_1$-$C_3$-alkylene-O—$C_1$-$C_6$-haloalkyl, —$C_1$-$C_3$-alkylene-NH$_2$, —NH$_2$, —C(O)O—$C_1$-$C_6$-alkyl, —N($R^{b1}$)C(O)$R^{b1}$, —CON($R^{a1}$)($R^{b1}$), —C(O)$R^{b1}$, —OC(O)$R^{b1}$, —OS(O)$_2$N($R^{a1}$)($R^{b1}$), —CO$_2$H, —CO$_2R^{b1}$, —N($R^{b1}$)C(O)N($R^{b1}$)$_2$, —S—$R^{b1}$, —S(O)$_2R^{b1}$, —S(O)$R^{b1}$, —SO$_2$N($R^{a1}$)($R^{b1}$), —N($R^{a1}$)($R^{b1}$), —N($R^{b1}$)S(O)$_2R^{b1}$, —N($R^{b1}$)C(O)O($R^{b1}$), —N($R^{b1}$)S(O)$_2$O($R^{b1}$), -$L^{1a}$-O—$R^{b1}$, -$L^{1a}$-CN, -$L^{1a}$-N($R^{b1}$)C(O)$R^{b1}$, -$L^{1a}$-CON($R^{a1}$)($R^{b1}$), -$L^{1a}$-C(O)$R^{b1}$, -$L^{1a}$-OC(O)$R^{b1}$, -$L^{1a}$-CO$_2$H, -$L^{1a}$-CO$_2R^{b1}$, -$L^{1a}$-N($R^{b1}$)C(O)N($R^{b1}$)$_2$, -$L^{1a}$-S—$R^{b1}$, -$L^{1a}$-S(O)$_2R^{b1}$, -$L^{1a}$-S(O)$R^{b1}$, -$L^{1a}$-SO$_2$N($R^{a1}$)($R^{b1}$), -$L^{1a}$-N($R^{a1}$)($R^{b1}$), -$L^{1a}$-N($R^{b1}$)S(O)$_2R^{b1}$, and -$L^{1a}$-N($R^{b1}$)C(O)O($R^{b1}$);

$R^2$ is methyl or ethyl;

$R^3$ is methyl or ethyl;

$R^4$ and $R^5$ are independently selected from the group consisting of hydrogen, $C_1$-$C_6$-alkyl, and $C_1$-$C_6$-haloalkyl;

$R^6$ is selected from the group consisting of hydrogen, $C_1$-$C_6$-alkyl, and $C_1$-$C_6$-haloalkyl;

$G^1$ is phenyl or monocyclic heteroaryl, wherein the phenyl or monocyclic heteroaryl are optionally substituted with 1, 2, 3, 4, or 5 substituents selected from the group consisting of halogen, $C_1$-$C_6$-alkyl, $C_1$-$C_6$-haloalkyl, —O—$R^f$, —CN, —N($R^f$)C(O)$R^f$, —CON($R^e$)($R^f$), —C(O)$R^f$, —OC(O)$R^f$, —CO$_2$H, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, —N($R^f$)C(O)O($R^f$), -$L^3$-O—$R^f$, -$L^3$-CN, -$L^3$-N($R^f$)C(O)$R^f$, -$L^3$-CON($R^e$)($R^f$), -$L^3$-C(O)$R^f$, -$L^3$-OC(O)$R^f$, -$L^3$-CO$_2$H, -$L^3$-CO$_2R^f$, -$L^3$-N($R^f$)C(O)N($R^f$)$_2$, -$L^3$-S—$R^f$, -$L^3$-S(O)$_2R^f$, -$L^3$-S(O)$R^f$, -$L^3$-SO$_2$N($R^e$)($R^f$), -$L^3$-N($R^e$)($R^f$), -$L^3$-N($R^f$)S(O)$_2R^f$, and -$L^3$-N($R^f$)C(O)O($R^f$); and X is NR$^g$; wherein $L^{1a}$, $L^3$, $R^{a1}$, $R^{b1}$, $R^e$, $R^f$ and $R^g$ are as described herein.

In one particular subgroup, the present disclosure features compounds of formula (I), wherein $R^1$ is phenyl, bicyclic aryl or monocyclic heteroaryl; wherein the phenyl, the bicyclic aryl, and the monocyclic heteroaryl are optionally substituted with 1, 2, 3, 4, or 5 substituents selected from the group consisting of halogen, $C_1$-$C_6$-alkyl, $C_1$-$C_6$-haloalkyl, —OCH$_2$O—, —O—$R^b$, —CN, —N($R^b$)C(O)$R^b$, —CON($R^a$)($R^b$), —C(O)$R^b$, —OC(O)$R^b$, —OS(O)$_2$N($R^a$)($R^b$), —CO$_2$H, —CO$_2R^b$, —N($R^b$)C(O)N($R^b$)$_2$, —S—$R^b$, —S(O)$_2R^b$, —S(O)$R^b$, —SO$_2$N($R^a$)($R^b$), —N($R^a$)($R^b$), —N($R^b$)S(O)$_2R^b$, —N($R^b$)C(O)O($R^b$), —N($R^b$)S(O)$_2$O($R^b$), -$L^1$-O—$R^b$, -$L^1$-CN, -$L^1$-N($R^b$)C(O)$R^b$, -$L^1$-CON($R^a$)($R^b$), -$L^1$-C(O)$R^b$, -$L^1$-OC(O)$R^b$, -$L^1$-CO$_2$H, -$L^1$-CO$_2R^b$, -$L^1$-N($R^b$)C(O)N($R^b$)$_2$, -$L^1$-S—$R^b$, -$L^1$-S(O)$_2R^b$, -$L^1$-S(O)$R^b$, -$L^1$-SO$_2$N($R^a$)($R^b$), -$L^1$-N($R^a$)($R^b$), -$L^1$-N($R^b$)S(O)$_2R^b$, and -$L^1$-N($R^b$)C(O)O($R^b$);

$R^2$ is methyl or ethyl;

$R^3$ is methyl or ethyl;

$R^4$ and $R^5$ are independently selected from the group consisting of hydrogen, $C_1$-$C_6$-alkyl, and $C_1$-$C_6$-haloalkyl;

$R^6$ is selected from the group consisting of hydrogen, $C_1$-$C_6$-alkyl, and $C_1$-$C_6$-haloalkyl;

$G^1$ is phenyl or monocyclic heteroaryl, wherein the phenyl or monocyclic heteroaryl are optionally substituted with 1, 2, 3, 4, or 5 substituents selected from the group consisting of halogen, $C_1$-$C_6$-alkyl, $C_1$-$C_6$-haloalkyl, —O—$R^f$, —CN, —N($R^f$)C(O)$R^f$, —CON($R^e$)($R^f$), —C(O)$R^f$, —OC(O)$R^f$, —CO$_2$H, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, —N($R^f$)C(O)O($R^f$), -$L^3$-O—$R^f$, -$L^3$-CN, -$L^3$-N($R^f$)C(O)$R^f$, -$L^3$-CON($R^e$)($R^f$), -$L^3$-C(O)$R^f$, -$L^3$-OC(O)$R^f$, -$L^3$-CO$_2$H, -$L^3$-CO$_2R^f$, -$L^3$-N($R^f$)C(O)N($R^f$)$_2$, -$L^3$-S—$R^f$, -$L^3$-S(O)$_2R^f$, -$L^3$-S(O)$R^f$, -$L^3$-SO$_2$N($R^e$)($R^f$), -$L^3$-N($R^e$)($R^f$), -$L^3$-N($R^f$)S(O)$_2R^f$, and -$L^3$-N($R^f$)C(O)O($R^f$); and X is $NR^g$; wherein $L^1$, $L^3$, $R^a$, $R^b$, $R^e$, $R^f$ and $R^g$ are as described herein.

In another particular subgroup, the present disclosure features compounds of formula (I), wherein $R^1$ is $C_3$-$C_8$-cycloalkyl-$C_1$-$C_6$-alkyl, phenyl-$C_1$-$C_6$-alkyl, heterocyclyl-$C_1$-$C_6$-alkyl, or monocyclic heteroaryl-$C_1$-$C_6$-alkyl; wherein the $C_3$-$C_8$-cycloalkyl of $C_3$-$C_8$-cycloalkyl-$C_1$-$C_6$-alkyl and heterocyclyl of heterocyclyl-$C_1$-$C_6$-alkyl are optionally substituted with 1, 2, 3, or 4 substituents selected from the group consisting of $C_1$-$C_{10}$-alkyl, $C_2$-$C_{10}$-alkenyl, $C_2$-$C_{10}$-alkynyl, $C_1$-$C_{10}$-haloalkyl, $C_2$-$C_{10}$-haloalkenyl, $C_2$-$C_{10}$-haloalkynyl, halogen, oxo, cyano, hydroxy, —O—$C_1$-$C_6$-alkyl, —O—$C_1$-$C_6$-haloalkyl, —$C_1$-$C_3$-alkylene-O—H, —$C_1$-$C_3$-alkylene-O—$C_1$-$C_6$-alkyl, —$C_1$-$C_3$-alkylene-O—$C_1$-$C_6$-haloalkyl, —$C_1$-$C_3$-alkylene-NH$_2$, —NH$_2$, —C(O)O—$C_1$-$C_6$-alkyl, —N($R^{b1}$)C(O)$R^{b1}$, —CON($R^{a1}$)($R^{b1}$), —C(O)$R^{b1}$, —OC(O)$R^{b1}$, —OS(O)$_2$N($R^{a1}$)($R^{b1}$), —CO$_2$H, —CO$_2R^{b1}$, —N($R^{b1}$)C(O)N($R^{b1}$)$_2$, —S—$R^{b1}$, —S(O)$_2R^{b1}$, —S(O)$R^{b1}$, —SO$_2$N($R^{a1}$)($R^{b1}$), —N($R^{a1}$)($R^{b1}$), —N($R^{b1}$)S(O)$_2R^{b1}$, —N($R^{b1}$)C(O)O($R^{b1}$), —N($R^{b1}$)S(O)$_2$O($R^{b1}$), -$L^{1a}$-O—$R^{b1}$, -$L^{1a}$-CN, -$L^{1a}$-N($R^{b1}$)C(O)$R^{b1}$, -$L^{1a}$-CON($R^{a1}$)($R^{b1}$), -$L^{1a}$-C(O)$R^{b1}$, -$L^{1a}$-OC(O)$R^{b1}$, -$L^{1a}$-CO$_2$H, -$L^{1a}$-CO$_2R^{b1}$, -$L^{1a}$-N($R^{b1}$)C(O)N($R^{b1}$)$_2$, -$L^{1a}$-S—$R^{b1}$, -$L^{1a}$-S(O)$_2R^{b1}$, -$L^{1a}$-S(O)$R^{b1}$, -$L^{1a}$-SO$_2$N($R^{a1}$)($R^{b1}$), -$L^{1a}$-N($R^{a1}$)($R^{b1}$), -$L^{1a}$-N($R^{b1}$)S(O)$_2R^{b1}$, and -$L^{1a}$-N($R^{b1}$)C(O)O($R^{b1}$); wherein the phenyl of phenyl-$C_1$-$C_6$-alkyl and monocyclic heteroaryl of monocyclic heteroaryl-$C_1$-$C_6$-alkyl are optionally substituted with 1, 2, 3, 4, or 5 substituents selected from the group consisting of halogen, $C_1$-$C_6$-alkyl, $C_1$-$C_6$-haloalkyl, —OCH$_2$O—, —O—$R^b$, —CN, —N($R^b$)C(O)$R^b$, —CON($R^a$)($R^b$), —C(O)$R^b$, —OC(O)$R^b$, —OS(O)$_2$N($R^a$)($R^b$), —CO$_2$H, —CO$_2R^b$, —N($R^b$)C(O)N($R^b$)$_2$, —S—$R^b$, —S(O)$_2R^b$, —S(O)$R^b$, —SO$_2$N($R^a$)($R^b$), —N($R^a$)($R^b$), —N($R^b$)S(O)$_2$O($R^b$), —N($R^b$)C(O)O($R^b$), —N($R^b$)S(O)$_2$O($R^b$), -$L^1$-O—$R^b$, -$L^1$-CN, -$L^1$-N($R^b$)C(O)$R^b$, -$L^1$-CON($R^a$)($R^b$), -$L^1$-C(O)$R^b$, -$L^1$-OC(O)$R^b$, -$L^1$-CO$_2$H, -$L^1$-CO$_2R^b$, -$L^1$-N($R^b$)C(O)N($R^b$)$_2$, -$L^1$-S—$R^b$, -$L^1$-S(O)$_2R^b$, -$L^1$-S(O)$R^b$, -$L^1$-SO$_2$N($R^a$)($R^b$), -$L^1$-N($R^a$)($R^b$), -$L^1$-N($R^b$)S(O)$_2R^b$, and -$L^1$-N($R^b$)C(O)O($R^b$);

$R^2$ is methyl or ethyl;

$R^3$ is methyl or ethyl;

$R^4$ and $R^5$ are independently selected from the group consisting of hydrogen, $C_1$-$C_6$-alkyl, and $C_1$-$C_6$-haloalkyl;

$R^6$ is selected from the group consisting of hydrogen, $C_1$-$C_6$-alkyl, and $C_1$-$C_6$-haloalkyl;

$G^1$ is phenyl or monocyclic heteroaryl, wherein the phenyl or monocyclic heteroaryl are optionally substituted with 1, 2, 3, 4, or 5 substituents selected from the group consisting of halogen, $C_1$-$C_6$-alkyl, $C_1$-$C_6$-haloalkyl, —O—$R^f$, —CN, —N($R^f$)C(O)$R^f$, —CON($R^e$)($R^f$), —C(O)$R^f$, —OC(O)$R^f$, —CO$_2$H, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, —N($R^f$)C(O)O($R^f$), -$L^3$-O—$R^f$, -$L^3$-CN, -$L^3$-N($R^f$)C(O)$R^f$, -$L^3$-CON($R^e$)($R^f$), -$L^3$-C(O)$R^f$, -$L^3$-OC(O)$R^f$, -$L^3$-CO$_2$H, -$L^3$-CO$_2R^f$, -$L^3$-N($R^f$)C(O)N($R^f$)$_2$, -$L^3$-S—$R^f$, -$L^3$-S(O)$_2R^f$, -$L^3$-S(O)$R^f$, -$L^3$-SO$_2$N($R^e$)($R^f$), -$L^3$-N($R^e$)($R^f$), -$L^3$-N($R^f$)S(O)$_2R^f$, and -$L^3$-N($R^f$)C(O)O($R^f$); and X is $NR^g$; wherein $L^1$, $L^{1a}$, $L^3$, $R^a$, $R^{a1}$, $R^b$, $R^{b1}$, $R^e$, $R^f$ and $R^g$ are as described herein.

In certain embodiments, $R^1$ is selected from the group consisting of phenyl, cyclohexyl, cyclopentyl, cycloheptyl, cyclobutyl, norbornyl, indanyl, benzodioxolyl, pyridinyl, pyrazolyl, morpholinyl, thiadiazolyl, tetrahydrothiophenyl, piperidinyl and isoxazolyl.

In certain embodiments, $R^1$ is selected from the group consisting of phenyl and cyclohexyl.

In certain embodiments, $G^1$ is selected from the group consisting of phenyl, pyridinyl, imidazolyl, pyrazolyl and isoxazolyl.

In certain embodiments, $G^1$ is selected from the group consisting of phenyl and pyridinyl.

In certain embodiments, $R^1$ is cyclohexyl, and $G^1$ is pyridinyl.

In certain embodiments, $R^1$ is phenyl, and $G^1$ is pyridinyl.

In certain embodiments, $R^1$ is an optionally substituted cyclohexyl; $R^2$ and $R^3$ are each methyl; $R^4$, $R^5$ and $R^6$ are each hydrogen; X is $NR^g$, wherein $R^g$ is hydrogen; and $G^1$ is an optionally substituted pyridinyl.

In certain embodiments, $R^1$ is an optionally substituted phenyl; $R^2$ and $R^3$ are each methyl; $R^4$, $R^5$ and $R^6$ are each hydrogen; X is $NR^g$, wherein $R^g$ is hydrogen; and $G^1$ is an optionally substituted pyridinyl.

Exemplary compounds include, but are not limited to:

$N^4$-cyclohexyl-5,6-dimethyl-$N^2$-(pyridin-2-ylmethyl)pyrimidine-2,4-diamine;

$N^4$-(2-methylbenzyl)-$N^2$-(pyridin-2-ylmethyl)-6,7-dihydro-5H-cyclopenta[d]pyrimidine-2,4-diamine;

$N^4$-cycloheptyl-6-methyl-$N^2$-(pyridin-2-ylmethyl)pyrimidine-2,4-diamine;

$N^4$-cyclohexyl-6-methyl-$N^2$-(pyridin-2-ylmethyl)pyrimidine-2,4-diamine;

$N^2$-benzyl-$N^4$-cyclohexyl-5,6-dimethylpyrimidine-2,4-diamine;

$N^4$-cyclohexyl-5,6-dimethyl-$N^2$-(pyridin-3-ylmethyl)pyrimidine-2,4-diamine;

2-({[4-(cyclohexylamino)-5,6-dimethylpyrimidin-2-yl]amino}methyl)-6-methylpyridin-3-ol;

$N^4$-cyclohexyl-$N^2$-(4-methoxybenzyl)-5,6-dimethylpyrimidine-2,4-diamine;

$N^4$-cyclohexyl-$N^2$-(4-fluorobenzyl)-5,6-dimethylpyrimidine-2,4-diamine;

$N^4$-cyclohexyl-5,6-dimethyl-$N^2$-[4-(trifluoromethoxy)benzyl]pyrimidine-2,4-diamine;

$N^4$-cyclohexyl-$N^2$-(4-isopropylbenzyl)-5,6-dimethylpyrimidine-2,4-diamine;

$N^4$-cyclohexyl-5,6-dimethyl-$N^2$-[4-(trifluoromethyl)benzyl]pyrimidine-2,4-diamine;

$N^4$-cyclohexyl-$N^2$-(3-fluorobenzyl)-5,6-dimethylpyrimidine-2,4-diamine;

$N^4$-cyclohexyl-5,6-dimethyl-$N^2$-(1H-pyrazol-5-ylmethyl)pyrimidine-2,4-diamine;

$N^4$-cyclohexyl-5,6-dimethyl-$N^2$-[(1R)-1-phenylethyl]pyrimidine-2,4-diamine;

$N^4$-cyclohexyl-5,6-dimethyl-$N^2$-[(1S)-1-phenylethyl]pyrimidine-2,4-diamine;

$N^4$-cyclohexyl-5,6-dimethyl-$N^2$-[(4-methylpyridin-2-yl)methyl]pyrimidine-2,4-diamine;

$N^4$-cyclohexyl-$N^2$-[(4-methoxypyridin-2-yl)methyl]-5,6-dimethylpyrimidine-2,4-diamine;

$N^4$-cyclohexyl-5,6-dimethyl-$N^2$-[(6-methylpyridin-2-yl)methyl]pyrimidine-2,4-diamine;

$N^4$-cyclohexyl-5,6-dimethyl-$N^2$-{[5-(trifluoromethyl)pyridin-2-yl]methyl}pyrimidine-2,4-diamine;

$N^2$-[(4-tert-butylpyridin-2-yl)methyl]-$N^4$-cyclohexyl-5,6-dimethylpyrimidine-2,4-diamine;
$N^4$-cyclohexyl-5,6-dimethyl-$N^2$-(2-thienylmethyl)pyrimidine-2,4-diamine;
$N^4$-cyclohexyl-$N^2$-[(3,5-dimethyl-1,2-oxazol-4-yl)methyl]-5,6-dimethylpyrimidine-2,4-diamine;
$N^4$-cyclohexyl-5,6-dimethyl-$N^2$-[(1-methyl-1H-imidazol-4-yl)methyl]pyrimidine-2,4-diamine;
$N^4$-cyclohexyl-$N^2$-(3-methoxybenzyl)-5,6-dimethylpyrimidine-2,4-diamine;
$N^4$-cyclohexyl-5,6-dimethyl-$N^2$-[(3-methylpyridin-2-yl)methyl]pyrimidine-2,4-diamine;
$N^2$-[(4-chloropyridin-2-yl)methyl]-$N^4$-cyclohexyl-5,6-dimethylpyrimidine-2,4-diamine;
$N^4$-(4,4-difluorocyclohexyl)-5,6-dimethyl-$N^2$-[(4-methylpyridin-2-yl)methyl]pyrimidine-2,4-diamine;
$N^4$-cyclopentyl-5,6-dimethyl-$N^2$-(pyridin-2-ylmethyl)pyrimidine-2,4-diamine;
5,6-dimethyl-$N^2$-(pyridin-2-ylmethyl)-$N^4$-(tetrahydro-2H-pyran-4-yl)pyrimidine-2,4-diamine;
5,6-dimethyl-$N^2$-(pyridin-2-ylmethyl)-$N^4$-[4-(trifluoromethyl)cyclohexyl]pyrimidine-2,4-diamine;
$N^4$-(4,4-difluorocyclohexyl)-5,6-dimethyl-$N^2$-(pyridin-2-ylmethyl)pyrimidine-2,4-diamine;
$N^4$-(2,3-dihydro-1H-inden-1-yl)-5,6-dimethyl-$N^2$-(pyridin-2-ylmethyl)pyrimidine-2,4-diamine;
3-({5,6-dimethyl-2-[(pyridin-2-ylmethyl)amino]pyrimidin-4-yl}amino)cyclopentanol;
5,6-dimethyl-$N^2$-(pyridin-2-ylmethyl)-$N^4$-(1,2,3,4-tetrahydronaphthalen-1-yl)pyrimidine-2,4-diamine;
$N^4$-(3,4-dihydro-2H-chromen-4-yl)-5,6-dimethyl-$N^2$-(pyridin-2-ylmethyl)pyrimidine-2,4-diamine;
cis-4-({5,6-dimethyl-2-[(pyridin-2-ylmethyl)amino]pyrimidin-4-yl}amino)-1-methylcyclohexanol;
trans-4-{5,6-dimethyl-2-[(pyridin-2-ylmethyl)amino]pyrimidin-4-yl}amino)-1-methylcyclohexanol;
$N^4$-(bicyclo[2.2.1]hept-2-yl)-5,6-dimethyl-$N^2$-(pyridin-2-ylmethyl)pyrimidine-2,4-diamine;
5,6-dimethyl-$N^4$-(2-methylcyclohexyl)-$N^2$-(pyridin-2-ylmethyl)pyrimidine-2,4-diamine;
$N^4$-(2,3-dimethylcyclohexyl)-5,6-dimethyl-$N^2$-(pyridin-2-ylmethyl)pyrimidine-2,4-diamine;
2-({5,6-dimethyl-2-[(pyridin-2-ylmethyl)amino]pyrimidin-4-yl}amino)cyclohexanol;
[(1R,2S)-2-({5,6-dimethyl-2-[(pyridin-2-ylmethyl)amino]pyrimidin-4-yl}amino)cyclohexyl]methanol;
$N^4$-(cyclopentylmethyl)-5,6-dimethyl-$N^2$-(pyridin-2-ylmethyl)pyrimidine-2,4-diamine;
$N^4$-cycloheptyl-5,6-dimethyl-$N^2$-(pyridin-2-ylmethyl)pyrimidine-2,4-diamine;
$N^4$-(2,3-dihydro-1H-inden-2-yl)-5,6-dimethyl-$N^2$-(pyridin-2-ylmethyl)pyrimidine-2,4-diamine;
$N^4$-cyclobutyl-5,6-dimethyl-$N^2$-(pyridin-2-ylmethyl)pyrimidine-2,4-diamine;
5,6-dimethyl-$N^4$-(pentan-3-yl)-$N^2$-(pyridin-2-ylmethyl)pyrimidine-2,4-diamine;
$N^4$-(3-fluorophenyl)-5,6-dimethyl-$N^2$-(pyridin-2-ylmethyl)pyrimidine-2,4-diamine;
$N^4$-(4-fluorophenyl)-5,6-dimethyl-$N^2$-(pyridin-2-ylmethyl)pyrimidine-2,4-diamine;
$N^4$-(2-fluorophenyl)-5,6-dimethyl-$N^2$-(pyridin-2-ylmethyl)pyrimidine-2,4-diamine;
5,6-dimethyl-$N^4$-phenyl-$N^2$-(pyridin-2-ylmethyl)pyrimidine-2,4-diamine;
5,6-dimethyl-$N^2$-(pyridin-2-ylmethyl)-$N^4$-[3-(trifluoromethoxy)phenyl]pyrimidine-2,4-diamine;
5,6-dimethyl-$N^2$-(pyridin-2-ylmethyl)-$N^4$-[3-(trifluoromethyl)phenyl]pyrimidine-2,4-diamine;
$N^4$-(2,6-difluorophenyl)-5,6-dimethyl-$N^2$-(pyridin-2-ylmethyl)pyrimidine-2,4-diamine;
5,6-dimethyl-$N^2$-(pyridin-2-ylmethyl)-$N^4$-[4-(trifluoromethoxy)phenyl]pyrimidine-2,4-diamine;
5,6-dimethyl-$N^2$-(pyridin-2-ylmethyl)-$N^4$-[4-(trifluoromethyl)phenyl]pyrimidine-2,4-diamine;
$N^4$-(3,4-difluorophenyl)-5,6-dimethyl-$N^2$-(pyridin-2-ylmethyl)pyrimidine-2,4-diamine;
5,6-dimethyl-$N^2$-(pyridin-2-ylmethyl)-$N^4$-[2-(trifluoromethoxy)phenyl]pyrimidine-2,4-diamine;
$N^4$-(2,5-difluorophenyl)-5,6-dimethyl-$N^2$-(pyridin-2-ylmethyl)pyrimidine-2,4-diamine;
$N^4$-(1,3-benzodioxol-5-yl)-5,6-dimethyl-$N^2$-(pyridin-2-ylmethyl)pyrimidine-2,4-diamine;
$N^4$-(4-chlorophenyl)-5,6-dimethyl-$N^2$-(pyridin-2-ylmethyl)pyrimidine-2,4-diamine;
5,6-dimethyl-$N^4$-(4-methylphenyl)-$N^2$-(pyridin-2-ylmethyl)pyrimidine-2,4-diamine;
$N^4$-(3,5-difluorophenyl)-5,6-dimethyl-$N^2$-(pyridin-2-ylmethyl)pyrimidine-2,4-diamine;
$N^4$-(3-chlorophenyl)-5,6-dimethyl-$N^2$-(pyridin-2-ylmethyl)pyrimidine-2,4-diamine;
$N^4$-(2-chlorophenyl)-5,6-dimethyl-$N^2$-(pyridin-2-ylmethyl)pyrimidine-2,4-diamine;
5,6-dimethyl-$N^4$-(2-methylphenyl)-$N^2$-(pyridin-2-ylmethyl)pyrimidine-2,4-diamine;
$N^4$-(2,6-dimethylphenyl)-5,6-dimethyl-$N^2$-(pyridin-2-ylmethyl)pyrimidine-2,4-diamine;
5,6-dimethyl-$N^4$-(3-methylphenyl)-$N^2$-(pyridin-2-ylmethyl)pyrimidine-2,4-diamine;
$N^4$-(1,1-dioxidotetrahydrothiophen-3-yl)-5,6-dimethyl-$N^2$-(pyridin-2-ylmethyl)pyrimidine-2,4-diamine;
$N^4$-(5-fluoro-2-methylphenyl)-5,6-dimethyl-$N^2$-(pyridin-2-ylmethyl)pyrimidine-2,4-diamine;
$N^4$-(2-fluoro-6-methylphenyl)-5,6-dimethyl-$N^2$-(pyridin-2-ylmethyl)pyrimidine-2,4-diamine;
$N^4$-(4,5-difluoro-2-methylphenyl)-5,6-dimethyl-$N^2$-(pyridin-2-ylmethyl)pyrimidine-2,4-diamine;
5,6-dimethyl-$N^4$-(1-methyl-1H-pyrazol-5-yl)-$N^2$-(pyridin-2-ylmethyl)pyrimidine-2,4-diamine;
$N^4$-(4-fluoro-2-methylphenyl)-5,6-dimethyl-$N^2$-(pyridin-2-ylmethyl)pyrimidine-2,4-diamine;
$N^4$-(3-fluoro-2-methylphenyl)-5,6-dimethyl-$N^2$-(pyridin-2-ylmethyl)pyrimidine-2,4-diamine;
$N^4$-cyclohexyl-$N^4$,5,6-trimethyl-$N^2$-(pyridin-2-ylmethyl)pyrimidine-2,4-diamine;
$N^4$-(3,3-difluorocyclopentyl)-5,6-dimethyl-$N^2$-(pyridin-2-ylmethyl)pyrimidine-2,4-diamine;
trans-4-({5,6-dimethyl-2-[(pyridin-2-ylmethyl)amino]pyrimidin-4-yl}amino)cyclohexanol;
$N^4$-(3,3-difluorocyclohexyl)-5,6-dimethyl-$N^2$-(pyridin-2-ylmethyl)pyrimidine-2,4-diamine;
5,6-dimethyl-$N^4$-(1-methylpiperidin-4-yl)-$N^2$-(pyridin-2-ylmethyl)pyrimidine-2,4-diamine;
tert-butyl 4-({5,6-dimethyl-2-[(pyridin-2-ylmethyl)amino]pyrimidin-4-yl}amino)piperidine-1-carboxylate;
5,6-dimethyl-$N^4$-(piperidin-4-yl)-$N^2$-(pyridin-2-ylmethyl)pyrimidine-2,4-diamine;
$N^4$-(2,6-diisopropylphenyl)-5,6-dimethyl-$N^2$-(pyridin-2-ylmethyl)pyrimidine-2,4-diamine;
3-({5,6-dimethyl-2-[(pyridin-2-ylmethyl)amino]pyrimidin-4-yl}amino)cyclohexanol;
$N^4$-cyclohexyl-5,6-dimethyl-$N^2$-[(5-methylpyridin-2-yl)methyl]pyrimidine-2,4-diamine;

$N^4$-cyclohexyl-5,6-dimethyl-$N^2$-[1-(pyridin-2-yl)ethyl]pyrimidine-2,4-diamine;

$N^4$-(2,4-difluorophenyl)-5,6-dimethyl-$N^2$-(pyridin-2-ylmethyl)pyrimidine-2,4-diamine;

5-ethyl-$N^4$-(4-fluorophenyl)-6-methyl-$N^2$-(pyridin-2-ylmethyl)pyrimidine-2,4-diamine;

$N^4$-(4,4-difluorocyclohexyl)-$N^2$-[(4-ethylpyridin-2-yl)methyl]-5,6-dimethylpyrimidine-2,4-diamine;

5,6-dimethyl-$N^2$-(pyridin-2-ylmethyl)-$N^4$-(tetrahydrofuran-2-ylmethyl)pyrimidine-2,4-diamine;

$N^4$-(cyclohexylmethyl)-5,6-dimethyl-$N^2$-(pyridin-2-ylmethyl)pyrimidine-2,4-diamine;

5,6-dimethyl-$N^4$-(pyridin-3-yl)-$N^2$-(pyridin-2-ylmethyl)pyrimidine-2,4-diamine;

5,6-dimethyl-$N^2$-(pyridin-2-ylmethyl)-$N^4$-(1,3,4-thiadiazol-2-yl)pyrimidine-2,4-diamine;

5,6-dimethyl-$N^4$-(1,2-oxazol-3-yl)-$N^2$-(pyridin-2-ylmethyl)pyrimidine-2,4-diamine;

5,6-dimethyl-$N^4$-(5-methyl-1,2-oxazol-3-yl)-$N^2$-(pyridin-2-ylmethyl)pyrimidine-2,4-diamine; or $N^4$-(4-fluorobenzyl)-5,6-dimethyl-$N^2$-(pyridin-2-ylmethyl)pyrimidine-2,4-diamine.

Isomers

The present disclosure contemplates various stereoisomers and mixtures thereof, and these are specifically included within the scope of this disclosure. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, or (2) direct separation of the mixture of optical enantiomers on chiral chromatographic columns.

Geometric isomers may exist in the disclosed compounds. The present disclosure contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

It is to be understood that compounds disclosed herein may exhibit the phenomenon of tautomerism.

Thus, the formulae drawings within this specification can represent only one of the possible tautomeric or stereoisomeric forms. It is to be understood that the disclosed compounds encompass any tautomeric or stereoisomeric forms, and mixtures thereof, and are not to be limited merely to any one tautomeric or stereoisomeric form utilized within the naming of the compounds or formulae drawings.

Isotopes

The disclosure also include isotopically-labeled compounds, which are identical to disclosed compounds, but for the fact that one or more atoms are replaced by an atom having an atomic mass or mass number different from the atomic mass or mass number usually found in nature. Examples of isotopes suitable for inclusion in the disclosed compounds are hydrogen, carbon, nitrogen, oxygen, phosphorus, fluorine, and chlorine, such as but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^2$H, can afford certain therapeutic advantages resulting from greater metabolic stability, for example increased in vivo half-life or reduced dosage requirements and, hence, may be employed in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of the present disclosure can generally be prepared by conventional techniques known to those skilled in the art or by processes analogous to those described in the accompanying Examples using appropriate isotopically-labeled reagent in place of non-isotopically-labeled reagent.

Salts

This disclosure is also directed, in part, to all salts of the disclosed compounds. A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt may be pharmaceutically acceptable and/or physiologically compatible. The term "pharmaceutically acceptable" is used adjectivally in this disclosure to mean that the modified noun is appropriate for use as a pharmaceutical product or as a part of a pharmaceutical product. Pharmaceutically acceptable salts include, for example, salts commonly used to form alkali metal salts and to form addition salts of free acids or free bases. In general, these salts typically may be prepared by conventional means by reacting, for example, the appropriate acid or base with a disclosed compound.

Pharmaceutically acceptable acid addition salts of the disclosed compounds can be prepared from an inorganic or organic acid. Examples of suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the disclosed compounds include, for example, metallic salts and organic salts. Metallic salts may include alkali metal (group Ia) salts, alkaline earth metal (group IIa) salts, and other physiologically acceptable metal salts. Such salts may be made from aluminum, calcium, lithium, magnesium, potassium, sodium, and zinc. Organic salts can be made from amines, such as tromethamine, diethylamine, N,N'- dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Purity

The disclosed compounds (and salts thereof) with any level of purity (including pure and substantially pure) are within the scope of the present disclosure. The term "substantially pure" in reference to a compound/salt/isomer, means that the preparation/composition containing the compound/salt/isomer contains more than about 85% by weight of the compound/salt/isomer, more than about 90% by weight of the compound/salt/isomer, more than about 95% by weight of the compound/salt/isomer, more than about 97% by weight of the compound/salt/isomer, and more than about 99% by weight of the compound/salt/isomer.

Compositions

The disclosure is also directed, in part, to compositions comprising one or more of the disclosed compounds and/or salts thereof. In some embodiments, the compositions comprise one or more substantially phase pure crystalline forms. The compositions may be pharmaceutical compositions.

In some embodiments, the compositions further comprise one or more additional therapeutic agents. Such therapeutic agents may include, for example, one or more therapeutic agents used to treat respiratory syncytial virus (e.g., the current standard of therapy).

The components of the compositions may depend on the method of administration, and may comprise one or more conventional pharmaceutically acceptable carriers, adjuvants, and/or vehicles (together referred to as "excipients"). Formulation of drugs is generally discussed in, for example, Hoover, J., *Remington's Pharmaceutical Sciences* (Mack Publishing Co., 1975) and Ansel's *Pharmaceutical Dosage Forms and Drug Delivery Systems* (Lippincott Williams & Wilkins, 2005).

The disclosed pharmaceutical compositions may be administered to a patient in need thereof via a variety of routes, such as orally, parenterally, sublingually, rectally, topically or by inhalation. Topical administration may involve the use of transdermal administration such as transdermal patches or iontophoresis devices. Parenteral administration includes, but is not limited to, subcutaneous, intravenous, intramuscular or intrasternal injections, and infusion techniques.

Solid dosage forms for oral administration include, for example, capsules, tablets, pills, powders, and granules. In such solid dosage forms, the disclosed compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs containing inert diluents commonly used in the art (e.g., water). Such compositions may also comprise, for example, wetting, emulsifying, suspending, flavoring (e.g., sweetening), and/or perfuming agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the excipients mentioned for use in the formulations for oral administration. A compound or salt of the invention can be dissolved in water, polyethylene glycol, propylene glycol, ethanol, corn oil, cottonseed oil, peanut oil, sesame oil, benzyl alcohol, sodium chloride, and/or various buffers. The pH may be adjusted, if necessary, with a suitable acid, base, or buffer.

Suppositories for rectal administration may be prepared by, for example, mixing a compound or salt of the invention with a suitable nonirritating excipient that is solid at ordinary temperatures, but liquid at the rectal temperature, and will, therefore, melt in the rectum to release the drug. Suitable excipients include, for example, cocoa butter; synthetic mono-, di-, or triglycerides, fatty acids, and/or polyethylene glycols.

Topical administration includes the use of transdermal administration, such as transdermal patches or iontophoresis devices.

The disclosed compounds or pharmaceutical compositions may be formulated to be suitable for inhalation. The pharmaceutical composition may be in the form of a solution, suspension, powder or other suitable form for pulmonary administration. These compositions may be administered to the lungs by any suitable delivery method such as, for example, in an aerosol, atomized, nebulized, or vaporized form through devices known in the art to affect such delivery. The amount of the disclosed pharmaceutical composition may be controlled by providing a valve to deliver a metered amount such as in a metered dose inhalers (MDI) that delivers a fixed dose in a spray with each actuation of the device. The pharmaceutical compositions may be formulated with one or more suitable propellants, such as, for example, dichlorodifluoromethane, trichlorofluoromethane, dichlorotetrafluoroethane, carbon dioxide or other suitable gas. Capsules and cartridges for use in an inhaler or insufflator may be formulated containing a powder mix of the disclosed compounds or pharmaceutical compositions and a suitable powder base such as lactose or starch.

The pharmaceutical compositions may be formulated with one or more binding agent as a dry powder for inhalation.

The disclosed compounds or pharmaceutical compositions may be in the form of sustained- or controlled-delivery formulations. Techniques for making such sustained- and controlled-delivery formulations are well-known to those skilled in the art. Among these are delivery methods that use liposome carriers, bio-erodible microparticles, porous beads, and semi-permeable polymer matrices.

Other excipients and modes of administration known in the pharmaceutical art also may be used.

The total daily dose of the disclosed compounds or salts thereof (administered in single or divided doses) may be from about 0.001 to about 100 mg/kg, from about 0.001 to about 30 mg/kg, or from about 0.01 to about 10 mg/kg (i.e., mg of the compound or salt per kg body weight). Dosage unit compositions may contain such amounts or submultiples thereof to make up the daily dose. In many instances, the administration of the disclosed compounds or salts thereof will be repeated a plurality of times. Multiple doses per day typically may be used to increase the total daily dose, if desired.

Factors affecting the dosage regimen include the type, age, weight, sex, diet, and condition of the patient; the severity of the pathological condition; the route of administration; pharmacological considerations, such as the activity, efficacy, pharmacokinetic, and toxicology profiles of the particular compound or salt used; whether a drug delivery system is utilized; the period of time during which RSV infection is most likely to occur such as during a defined RSV season; and whether the compound or salt is administered as part of a drug combination. Thus, the dosage regimen actually employed can vary widely, and therefore, can derive from the dosage regimen set forth above.

Kits

This disclosure is also directed, in part, to kits comprising one or more of the disclosed compounds and/or salts thereof. The kits may optionally contain one or more additional therapeutic agents and/or instructions for action such as using the kit.

Methods of Use.

This disclosure is directed, in part, to a method for inhibiting infection and/or replication of an RNA virus. The method comprises exposing the virus to one or more of the disclosed compounds and/or salts thereof. In embodiments, infection and/or replication of the RNA virus are inhibited in vitro. In embodiments, infection and/or replication of the RNA virus are inhibited in vivo. In embodiments, the RNA virus whose infection and/or replication are being inhibited is a single-stranded, negative sense RNA virus. In embodiments, the RNA virus whose infection and/or replication are being inhibited is a virus from the Paramyxoviridae family. In embodiments, the RNA virus whose infection and/or replication is being inhibited is RSV.

The term "inhibiting" means reducing the level of infection and/or RNA virus replication either in vitro or in vivo. The inhibition may act on any stage of viral infection and/or replication, such as (but not exclusively) attachment, penetration, uncoating, genome replication, assembly, maturation or egress from infected cells. The target of the compound might be either a viral or host component (or rarely both) involved in viral infection and/or replication. For example, if a disclosed compound/salt reduces the level of infection and/or RNA virus replication by at least about 10% compared to the level of RNA virus infection and/or replication before the virus is exposed to the compound/salt, then the compound/salt inhibits RNA virus infection and/or replication. In some embodiments, the compound/salt can inhibit RNA virus infection and/or replication by at least about 20%, at least about 30%, at least about 40%, at least about 50%, at least about 60%, at least about 70%, at least about 80%, at least about 90%, or at least about 95%.

This disclosure also is directed, in part, to a method for treating RSV infection in a subject in need of such treatment. These methods comprise administering to the subject one or more of the disclosed compounds and/or salts thereof, and, optionally, one or more additional therapeutic agents. In some embodiments, a therapeutically effective amount of the compound(s) and/or salt(s) thereof is administered to the subject. "Treating" means ameliorating, suppressing, eradicating, preventing, reducing the risk of, and/or delaying the onset of the infection or disease being treated. For example, the disclosed compounds and/or salts thereof may be used for prophylaxis to prevent infection of uninfected subjects, and/or the spread of the virus to the lower respiratory tract in patients already infected with the virus. The term "treating" encompasses administration of the disclosed compounds and/or salts thereof to a patient at risk for RSV infection. Patients at risk for RSV infection may include premature infants, children with bronchopulmonary dysplasia, children with congenital heart or lung disease, the elderly and immunocompromised and other patients who are unable to mount a sufficient immune responses due to their immature or weaker immune systems. The disclosed compounds and/or salts thereof may be administered to patients with a low tolerance to the side effects of current therapies.

The methods of treatment are particularly suitable for use with humans, but may be used with other animals. A "therapeutically effective amount" or "effective amount" is an amount that will substantially achieve the goal of treating the targeted condition.

In embodiments, the disclosed methods comprise combination therapy, wherein the disclosed compound(s) and/or salt(s) is/are co-administered with a second compound, such as, for example, another therapeutic agent used to treat RSV such as, for example, the current standard of therapy, and other antivirals. In these co-administration embodiments, the disclosed compound(s) and/or salt(s) and the second, etc. therapeutic agent(s) may be administered in a substantially simultaneous manner (e.g., within at least about 5 minutes of each other), in a sequential manner, or both. For example, the disclosed compound(s) and/or salt(s) may be administered to a patient before, during or after treatment with the current standard of therapy, if such an administration is deemed medically necessary and/or appropriate.

This disclosure also is directed, in part, to uses of one or more of the disclosed compounds and/or salts, and, optionally, in combination with one or more additional therapeutic agents to prepare a medicament. In some embodiments, the medicament is for co-administration with one or more additional therapeutic agents.

In some embodiments, the medicament is for inhibiting replication of an RNA virus.

In some embodiments, the medicament is for treating RSV.

In embodiments, one or more of the disclosed compounds and/or salts may be used to prevent and/or treat RSV infections caused by one or both groups A or B RSV virus.

In embodiments, one or more of the disclosed compounds and/or salts may be used to inhibiting infection and/or replication of one or both of group A or group B RSV virus.

This disclosure also is directed, in part, to one or more of the disclosed compounds and/or salts of the invention, and, optionally, in combination with one or more additional therapeutic agents, for use in inhibiting replication of an RNA virus or for use in treating RSV infection.

BIOLOGICAL ASSAYS

Cells and Virus

HEp-2 cells and RSV (Group A, Long Strain) were obtained from the American Type Culture Collection (Manassas, Va.).

Antiviral (RSV) Assay

A cytopathetic effect (CPE) protection assay was performed to determine the ability of a compound to protect the cells from viral infection and thus the CPE induced by viral infection. 96-well plates were first seeded with $3 \times 10^3$ HEp-2 cells per well in Dulbecco's modified Eagle's medium (DMEM) containing 10% fetal bovine serum (FBS). One day after the cells were seeded, they were preincubated with serial dilutions of compounds prepared in 100 μL assay medium (DMEM mixed with F12 medium at a 1:1 ratio, supplemented with 2% FBS and 1 mM sodium pyruvate) for 1 hour at 37° C. 100 μL of assay medium containing 0.2 multiplicity of infection (MOI) of RSV was then added to each well of cells. In addition to wells containing infected cells incubated with compounds, each plate also contained replicates of two kinds of controls: (1) Virus control contained cells infected with 0.2 MOI of RSV in assay medium, (2) Uninfected cell control contained cells incubated with assay medium only. After 4 days of incubation at 37° C., the viability of cells was assessed using MTT (Thiazolyl blue tetrazolium bromide, Sigma). A stock solution of MTT, at a concentration of 4 mg/mL in phosphate-buffered saline, was added to all wells at 25 μL per well. Plates were further incubated for 4 hours, and each well was then treated with 50 μL of a solution containing 20% sodium dodecyl sulfate (SDS) and 0.02 N HCl. After an overnight incubation, the plates were measured on a BioTek® microtiter plate reader at wavelengths of 570 nm and 650 nm. The MTT detection is based on the fact that viable (uninfected) cells can reduce the tetrazolium salts into colored formazan products, which can then be quantitated by spectrometry. Based on the spectrometric absorbance of each sample, the percent of protection from CPE, which is an indicator of protection from viral infection, can be calculated for each compound and the 50% effective concentrations ($EC_{50}$) can be calculated using a nonlinear regression curve fitting equation provided by the GraphPad Prism® 4 software. Using the above-described assay, compounds of the present invention showed obvious inhibitory activities against RSV replication. Results are shown in Table 1.

TABLE 1

| Example | RSV $EC_{50}$ (μM) |
|---|---|
| 1 | 0.25 |
| 2 | 2.05 |
| 3 | 2.79 |
| 4 | 23.5 |
| 5 | 0.24 |
| 6 | 0.24 |
| 7 | >12 |
| 8 | >3.7 |
| 9 | >3.0 |
| 10 | >1.5 |
| 11 | >2.0 |
| 12 | >0.95 |
| 13 | >1.0 |
| 14 | 0.84 |

TABLE 1-continued

| Example | RSV $EC_{50}$ (μM) |
|---|---|
| 15 | >1.9 |
| 16 | >3.7 |
| 17 | 0.034 |
| 18 | 0.31 |
| 19 | 0.59 |
| 20 | >8.7 |
| 21 | >6.1 |
| 22 | 0.069 |
| 23 | >10 |
| 24 | 0.045 |
| 25 | >3.4 |
| 26 | >5.8 |
| 27 | 0.042 |
| 28 | 0.061 |
| 29 | 0.92 |
| 30 | 1.1 |
| 31 | >9.6 |
| 32 | 0.22 |
| 33 | 0.18 |
| 34 | 4.3 |
| 35 | 0.12 |
| 36 | 0.53 |
| 37 | 0.36 |
| 38 | 2.4 |
| 39 | 1.25 |
| 40 | 0.065 |
| 41 | 0.04 |
| 42 | 0.3 |
| 43 | 0.19 |
| 44 | 24 |
| 45 | 0.018 |
| 46 | 0.32 |
| 47 | >5.3 |
| 48 | 0.27 |
| 49 | 0.31 |
| 50 | 0.1 |
| 51 | 0.32 |
| 52 | 0.27 |
| 53 | 0.038 |
| 54 | 0.025 |
| 55 | 0.14 |
| 56 | 0.4 |
| 57 | 0.23 |
| 58 | 0.063 |
| 59 | 0.03 |
| 60 | 0.1 |
| 61 | 0.04 |
| 62 | 0.094 |
| 63 | 0.052 |
| 64 | 0.04 |
| 65 | 0.04 |
| 66 | 0.034 |
| 67 | 0.007 |
| 68 | 0.009 |
| 69 | 0.11 |
| 70 | 0.95 |
| 71 | 0.04 |
| 72 | 0.078 |
| 73 | 0.024 |
| 74 | 0.65 |
| 75 | 0.026 |
| 76 | 0.025 |
| 77 | 1.2 |
| 78 | 0.19 |
| 79 | 0.62 |
| 80 | 0.19 |
| 81 | 1.3 |
| 82 | 0.54 |
| 83 | 33 |
| 84 | 0.016 |
| 85 | 1.38 |
| 86 | 1.5 |
| 87 | >32 |
| 88 | 0.038 |
| 89 | 0.48 |
| 90 | 0.51 |
| 91 | 2.2 |
| 92 | 1.1 |

TABLE 1-continued

| Example | RSV EC$_{50}$ (μM) |
|---|---|
| 93 | 0.93 |
| 94 | 2.4 |
| 95 | 5.3 |
| 96 | 15 |
| 97 | 0.14 |

Cytotoxicity (MTT) Assay

Cytotoxicity of the compounds was determined in experiments done in parallel with the antiviral assays. To do this, 100 μL of assay medium was added to the wells of HEp-2 cells pretreated with 100 μL serially diluted compounds as described above. After 4 days of incubation, the viability of the cells was determined by the MTT assay in the same way as detailed in the "Antiviral Assay" method. Results were expressed as 50% toxicity dose (TD$_{50}$) values. Results are shown in Table 2.

Compound Testing Strategy

Compounds were tested to determine both their antiviral and toxicity to determine their therapeutic window. Determination of the EC$_{50}$ and TD$_{50}$ of these active compounds were repeated one additional time to confirm the window. Results are shown in Table 2.

TABLE 2

| Example | RSV EC$_{50}$ (μM) | MTT TD$_{50}$ (μM) | Window (TD$_{50}$/EC$_{50}$) |
|---|---|---|---|
| 1 | 0.15 | 23.00 | 153 |
| 2 | 2.05 | 7.17 | 3 |
| 3 | 2.79 | 8.04 | 3 |
| 4 | 23.5 | 39.00 | 1.6 |

General Synthesis

Additional information about the preparation of compounds of formulas I (and their salts) is provided in the general discussion and/or specific synthesis examples below. In the discussion below, $R^1$, $R^2$, $R^3$, $R^4$, $R^5$, $R^6$, $R^g$, and $G^1$ have the meaning discussed above unless otherwise stated.

The disclosed compounds may be made by methods known in the art including the methods described below and variations thereof

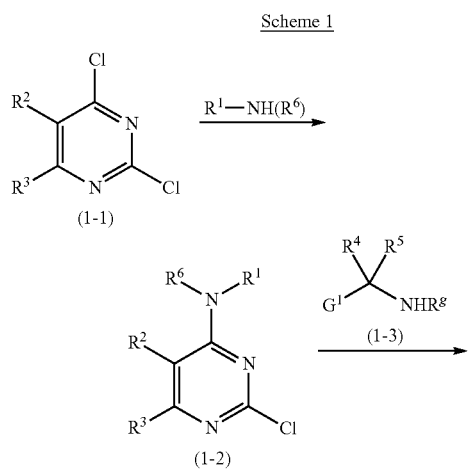

Certain disclosed compounds can be prepared as shown generally in Scheme 1. Dichloropyrimidines of formula (1-1) can be reacted with amines, $R^1$—NH($R^6$), at ambient temperature or heated in a solvent such as ethanol as described by Martyn D C, et al. *Bioorganic and Medicinal Chemistry Letters* 2010; 20: 228-231 to give compounds of formula (1-2). Dichloropyrimidines of formula (1-1) can also be reacted with amines, $R^1$—NH($R^6$), at ambient temperature or heated in a solvent such as N,N-dimethylformamide in the presence of a base such as cesium carbonate or triethylamine to give compounds of formula (1-2). Compounds of formula (1-2) can be reacted with amines of formula (1-3) heated either conventionally or by microwave irradiation in solvents such as acetonitrile, dioxane or isopropanol optionally in the presence of an acid such as hydrochloric acid in dioxane to give compounds of formula (1-4). Compounds of formula (1-4) are representative of compounds of formula (I).

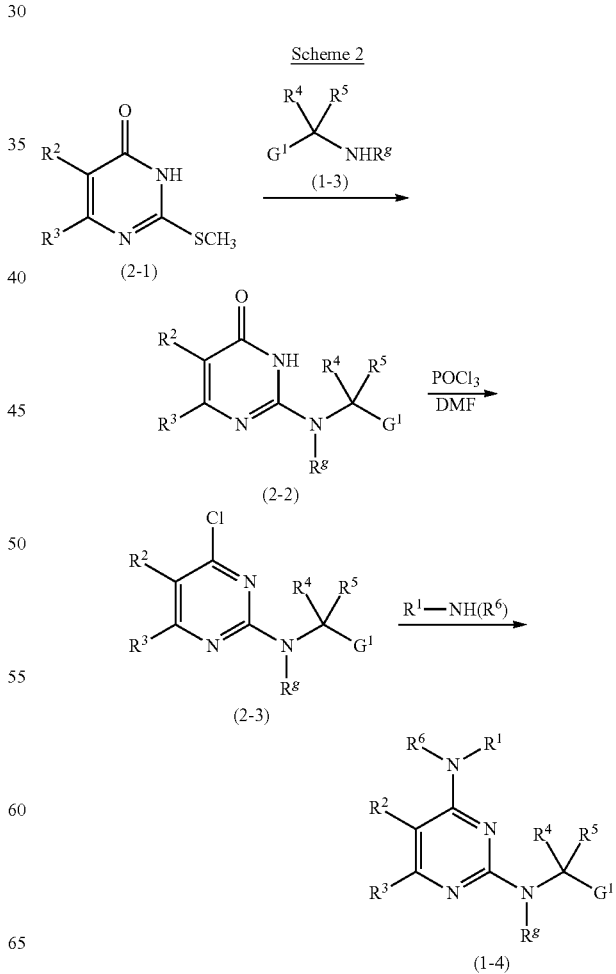

Certain disclosed compounds can be prepared as shown generally in Scheme 2. Compounds of formula (2-1) can be reacted with amines of formula (1-3) heated either conventionally or by microwave irradiation in solvents such as dimethyl sulfoxide to give compounds of formula (2-2). Compounds of formula (2-2) can be reacted with phosphorus (V) oxychloride in the presence of a catalytic amount of N,N-dimethylformamide (DMF) with heating to give compounds of formula (2-3). Compounds of formula (2-3) can be reacted with amines, $R^1$—NH($R^6$), heated in a solvent such as acetonitrile optionally in the presence of an acid catalyst such as hydrochloric acid in dioxane to give compounds of formula (1-4). Compounds of formula (1-4) are representative of compounds of formula (I).

In the foregoing Schemes, compounds are shown wherein an aromatic ring (e.g., phenyl) is substituted with groups in a particular regiochemistry (e.g., para). A starting material or intermediate with para-substitution provides a final product with para-substitution in the foregoing Schemes. It is understood by one of skill in the art that substitution in the foregoing Schemes of a starting material or intermediate with a different regiochemistry (e.g., meta) would provide a final product with a different regiochemistry. For example, replacement of a para-substituted starting material or intermediate in the foregoing Schemes with a meta substituted starting material or intermediate would lead to a meta-substituted product.

If a moiety described herein (e.g., —$NH_2$ or OH) is not compatible with the synthetic methods, the moiety may be protected with a suitable protecting group that is stable to the reaction conditions used in the methods. The protecting group may be removed at any suitable point in the reaction sequence to provide a desired intermediate or target compound. Suitable protecting groups and methods for protecting or deprotecting moieties are well known in the art, examples of which can be found in Greene T W and Wuts P G M, *Protective Groups in Organic Synthesis*, (3$^{rd}$ ed., John Wiley & Sons, NY (1999)). Optimum reaction conditions and reaction times for each individual step may vary depending on the particular reactants employed and substituents present in the reactants used. Solvents, temperatures and other reaction conditions may be readily selected by one of ordinary skill in the art based on the present disclosure.

Other disclosed compounds can be similarly prepared according to the above-described schemes as well as the procedures described in the following disclosure of intermediates, procedures, and examples as appreciated by those skilled in the art. It should be understood that the above-described embodiments and schemes and the following intermediates, general procedures, and examples disclosure are given by way of illustration, not limitation. Various changes and modifications within the scope of the present disclosure will become apparent to those skilled in the art from the present description.

EXAMPLES

Abbreviations: DMSO for dimethyl sulfoxide; and ESI for electrospray ionization.

Example 1

$N^4$-cyclohexyl-5,6-dimethyl-$N^2$-(pyridin-2-ylmethyl)pyrimidine-2,4-diamine

Step A 5,6-dimethyl-2-thioxo-2,3-dihydropyrimidin-4(1H)-one

To a stirred solution of potassium tert-butoxide (15.71 g, 0.140 mol) in tetrahydrofuran (200 mL) was added a solution of ethyl 2-methyl-3-oxobutanoate (20.0 g, 0.14 mol) and thiourea (10.55 g, 0.14 mol) in dry ethanol (150 mL). The resulting mixture was refluxed for 15 minutes and cooled down to ambient temperature. The formed precipitate was collected by filtration, washed with tetrahydrofuran (200 mL), and dissolved in water (200 mL). Acetic acid (100 mL) was added in to the resulting solution. The formed precipitate was collected by filtration and dried to yield 17 g (78.5%) of the titled compound. $^1$H NMR (300 MHz, DMSO-$d_6$) δ ppm 1.74 (s, 3H) 2.09 (s, 3H) 12.19 (s, 1H).

Step B 5,6-dimethylpyrimidine-2,4(1H,3H)-dione

A solution of 5,6-dimethyl-2-thioxo-2,3-dihydropyrimidin-4(1H)-one (14.4 g, 0.09 mol, Step A) and chloroacetic acid (100.0 g, 1.06 mol) in water (43 mL) was refluxed overnight, cooled down to ambient temperature and quenched with water (500 mL). The formed precipitate was collected by filtration and dried to yield 10.3 g (79.7%) of the titled compound. $^1$H NMR (300 MHz, DMSO-$d_6$) δ ppm 1.70 (s, 3H) 2.02 (s, 3H) 10.56 (s, 1H) 10.86 (s, 1H).

Step C 2,4-dichloro-5,6-dimethylpyrimidine

To a stirred solution of 5,6-dimethylpyrimidine-2,4(1H, 3H)-dione (10.3 g, 0.07 mol, Step B) in phosphorus (V) oxychloride (150 mL) was added dimethylformamide (0.2 ml). The resulting mixture was refluxed overnight under argon and cooled down to ambient temperature. The resulting mixture was evaporated. Toluene (200 mL) was added to the residue. The resulting mixture was concentrated. Cold water with ice (400 mL) was added to the residue, and the mixture was extracted with chloroform (3×150 mL). The combined organic layers were washed with brine, dried over magnesium sulfate, filtered and concentrated under reduced pressure. The crude product was purified by column chromatography on silica gel, eluting with ethyl acetate/hexane mixture (1:2-1:1) to yield 9.5 g (73%) of the titled compound. $^1$H NMR (400 MHz, CDCl$_3$) δ ppm 2.35 (s, 3H) 2.55 (s, 3H).

Step D 2-chloro-N-cyclohexyl-5,6-dimethylpyrimidin-4-amine

To a stirred solution of 2,4-dichloro-5,6-dimethylpyrimidine (9.3 g, 0.05 mol, Step C) in dimethylformamide (100 mL) was added cesium carbonate (37.6 g, 0.12 mol). Cyclohexylamine (5.7 g, 0.058 mol) was then added, keeping the temperature of the reaction mixture at 70° C. After 48 hours, the reaction mixture was concentrated, and the residue was quenched with water (200 mL). The resulting mixture was extracted with dichloromethane (3×120 mL). The combined organic layers were washed with brine, dried over magnesium sulfate, filtered, and concentrated. The solvent was removed by distillation, and the crude product was purified by column chromatography on silica gel eluting with ethyl acetate/methanol (10:1-10:2) to yield 4.9 g (38.9%) of the titled compound. $^1$H NMR (300 MHz, DMSO-$d_6$) δ ppm 1.05-1.14 (m, 1H), 1.28-1.33 (m, 4H), 1.61 (d, J=12.36 Hz, 1H), 1.72 (s, 2H), 1.80 (s, 2H), 1.93 (s, 3H), 2.19 (s, 3H), 3.85 (d, J=7.52 Hz, 1H), 6.66 (d, J=7.79 Hz, 1H); MS (ESI) m/z 240.3 (M+1)$^+$.

Step E $N^4$-cyclohexyl-5,6-dimethyl-$N^2$-(pyridin-2-ylmethyl)pyrimidine-2,4-diamine hydrochloride To a stirred solution of 2-chloro-N-cyclohexyl-5,6-dimethylpyrimidin-4-amine (0.1 g, 0.40 mmol) and (pyridin-2-ylmethyl)amine (0.04 g, 0.400 mmol) in acetonitrile (5 mL) was added a 3.5 M solution of hydrogen chloride in dioxane (0.2 mL). The resulting mixture was irradiated in CEM Focused Microwave™ Synthesis System at 160° C. for 120 minutes. The resulting mixture was cooled to ambient temperature. The formed precipitate was collected by filtration and dried to yield 0.07 g (48.2%) of the titled compound as the hydrochloride salt. $^1$H NMR (300 MHz, DMSO-$d_6$) δ ppm 0.99-1.03 (m, 2H), 1.13 (d, J=12.63 Hz, 1H), 1.20-1.26 (m, 2H), 1.51-1.59 (m, 2H), 1.60-1.63 (m, 3H), 1.89 (s, 3H), 2.24 (s, 3H), 3.70 (s, 1H), 4.62 (d, J=5.10 Hz, 2H), 7.24 (dd, J=7.25, 4.84 Hz, 1H), 7.31 (d, J=7.79 Hz, 1H), 7.58 (d, J=7.72 Hz, 1H, 7.74 (t, J=7.66 Hz, 1H), 8.1 (s, 1H), 8.50 (d, J=4.84 Hz, 1H); MS (ESI) m/z 312.3 (M+1)$^+$.

Examples 2-4 can be prepared using the methodology described in Scheme 1 and the reference cited therein.

Example 2

$N^4$-(2-methylbenzyl)-$N^2$-(pyridin-2-ylmethyl)-6,7-dihydro-5H-cyclopenta[d]pyrimidine-2,4-diamine $^1$H NMR (500 MHz, DMSO-$d_6$/$D_2O$) δ ppm 8.43 (d, J=4.9 Hz, 1H), 7.59-7.64 (m, 1H), 7.08-7.25 (m, 5H), 7.02-7.07 (m, 1H), 4.47-4.47 (bs, 2H), 4.41-4.43 (m, 2H), 2.55-2.60 (m, 4H), 2.21-2.22 (m, 3H), 1.94 (p, J=7.4 Hz, 2H); MS (ESI) (ESI+) m/z 346 (M+1)$^+$.

Example 3

$N^4$-cycloheptyl-6-methyl-$N^2$-(pyridin-2-ylmethyl)pyrimidine-2,4-diamine $^1$H NMR (400 MHz, DMSO-$d_6$/$D_2O$, temperature 90° C.) δ ppm 8.48 (d, J=4.0 Hz, 1H), 7.71 (td, J=7.6, 1.8 Hz, 1H), 7.32 (d, J=7.9 Hz, 1H), 7.21-7.26 (m, 1H), 6.59 (s, 2H), 5.71 (s, 1H), 4.58 (s, 2H), 3.75-3.87 (m, 1H), 2.09 (s, 3H), 1.67-1.81 (m, 2H), 1.30-1.63 (m, 10H).

Example 4

$N^4$-cyclohexyl-6-methyl-$N^2$-(pyridin-2-ylmethyl)pyrimidine-2,4-diamine $^1$H NMR (500 MHz, DMSO-$d_6$) δ ppm 12.23-12.39 (m, 1H), 8.52-8.56 (m, 2H), 8.26-8.30 (m, 1H), 7.84 (td, J=7.7, 1.6 Hz, 1H), 7.40 (d, J=7.8 Hz, 1H), 7.34 (dd, J=7.4, 5.0 Hz, 1H), 5.83 (s, 1H), 4.65 (d, J=5.6 Hz, 2H), 2.21 (s, 3H), 1.48-1.70 (m, 5H), 0.92-1.31 (m, 5H).

Example 5

$N^2$-benzyl-$N^4$-cyclohexyl-5,6-dimethylpyrimidine-2,4-diamine

The titled compound was synthesized according to the general procedure described for preparation of $N^4$-cyclohexyl-5,6-dimethyl-$N^2$-(pyridin-2-ylmethyl)pyrimidine-2,4-diamine (Example 1) using benzylamine instead of (pyridin-2-ylmethyl)amine to afford the crude product. The solvent was removed by distillation, and the crude product was purified by HPLC (column: YMC-PACK ODS-AQ C18, 250 mm×20 mm, 10 μm; gradient: 20-50% acetonitrile in 0.02% trifluoroacetic acid/water over fifteen minutes; 50-100% acetonitrile in 0.02% trifluoroacetic acid/water over five minutes; flow rate: 25 mL/min; temperature: 25° C.). The titled compound was obtained as the trifluoroacetic acid salt as a white solid. $^1$H NMR (300 MHz, DMSO-$d_6$) δ ppm 1.03-1.15 (m, 1H), 1.22-1.31 (m, 4H), 1.60 (d, J=12.63 Hz, 1H), 1.68 (s, 4H), 1.86 (s, 3H), 2.21 (s, 3H), 3.86-3.90 (m, 1H), 4.52 (d, J=5.64 Hz, 2H), 7.20-7.25 (m, 1H), 7.27-7.33 (m, 4H), 7.4 (bs, 1H), 8.02 (bs, 1H); MS (ESI) m/z 311.5 (M+1)$^+$.

Example 6

$N^4$-cyclohexyl-5,6-dimethyl-$N^2$-(pyridin-3-ylmethyl)pyrimidine-2,4-diamine

The titled compound was synthesized according to the general procedure described for preparation of $N^4$-cyclohexyl-5,6-dimethyl-$N^2$-(pyridin-2-ylmethyl)pyrimidine-2,4-diamine (Example 1) using 1-pyridin-3-ylmethanamine instead of (pyridin-2-ylmethyl)amine to afford the crude product. The solvent was removed by distillation, and the crude product was purified by HPLC (column: YMC-PACK ODS-AQ C18, 250 mm×20 mm, 10 μm; gradient: 20-50% acetonitrile in 0.02% trifluoroacetic acid/water over fifteen minutes; 50-100% acetonitrile in 0.02% trifluoroacetic acid/water over five minutes; flow rate: 25 mL/min; temperature: 25° C.) to afford the titled compound as the trifluoroacetate as a white solid. $^1$H NMR (400 MHz, CDCl$_3$) δ ppm 1.08-1.34 (m, 5H), 1.50-1.61 (m, 3H) 1.62-1.69 (m, 2H), 1.87 (s, 3H), 2.23 (s, 3H), 3.71-3.79 (m, 1H), 4.63 (d, J=5.10 Hz, 2H), 7.60 (d, J=7.79 Hz, 1H), 7.64 (dd, J=7.66, 5.24 Hz, 1H), 8.05 (d, J=7.79 Hz, 1H), 8.62 (d, J=4.57 Hz, 1H) 8.62-8.69 (m, 1H) 8.71 (s, 1H), 12.61 (bs, 1H); MS (ESI) m/z 312.5 (M+1)$^+$.

Example 7

2-({[4-(cyclohexylamino)-5,6-dimethylpyrimidin-2-yl]amino}methyl)-6-methylpyridin-3-ol The titled compound was synthesized according to the general procedure described for preparation of $N^4$-cyclohexyl-5,6-dimethyl-$N^2$-(pyridin-2-ylmethyl)pyrimidine-2,4-diamine (Example 1) using 2-(aminomethyl)-6-methylpyridin-3-ol instead of (pyridin-2-ylmethyl)amine. The crude product was purified by HPLC (column: YMC-PACK ODS-AQ C18, 250 mm×20 mm, 10 μm; gradient: 20-50% acetonitrile in 0.02% trifluoroacetic acid/water over fifteen minutes; 50-100% acetonitrile in 0.02% trifluoroacetic acid/ water over five minutes; flow rate: 25 mL/min; temperature: 25° C.) to afford the titled compound as the trifluoroacetate salt as a white solid. $^1$H NMR (300 MHz, DMSO-d$_6$) δ ppm 1.21-1.28 (m, 5H), 1.61-1.65 (m, 5H), 1.89 (s, 3H), 2.24 (s, 3H), 3.78 (s, 1H), 4.70 (d, J=4.82 Hz, 2H), 7.38 (d, J=8.55 Hz, 1H), 7.59 (d, J=3.73 Hz, 2H), 8.31 (s, 1H), 12.78 (bs, 1H); MS (ESI) m/z 342.8 (M+1)$^+$.

Example 8

N$^4$-cyclohexyl-N$^2$-(4-methoxybenzyl)-5,6-dimethylpyrimidine-2,4-diamine

The titled compound was synthesized according to the general procedure described for preparation of N$^4$-cyclohexyl-5,6-dimethyl-N$^2$-(pyridin-2-ylmethyl)pyrimidine-2,4-diamine (Example 1) using (4-methoxybenzyl)amine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 1.10-1.13 (m, 1H), 1.24-1.35 (m, 3H), 1.62 (d, J=13.16 Hz, 1H), 1.72 (d, J=9.94 Hz, 4H), 1.87 (s, 3H), 2.22 (s, 3H), 3.72 (s, 3H), 3.94 (s, 1H), 4.46 (d, J=5.37 Hz, 2H), 6.88 (s, 2H), 7.26 (s, 2H), 7.57 (s, 1H), 8.01 (s, 1H), 12.66 (bs, 1H); MS (ESI) m/z 341.7 (M+1)$^+$.

Example 9

N$^4$-cyclohexyl-N$^2$-(4-fluorobenzyl)-5,6-dimethylpyrimidine-2,4-diamine

The titled compound was synthesized according to the general procedure described for preparation of N$^4$-cyclohexyl-5,6-dimethyl-N$^2$-(pyridin-2-ylmethyl)pyrimidine-2,4-diamine (Example 1) using (4-fluorobenzyl)amine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 1.03-1.10 (m, 1H), 1.20-1.34 (m, 2H), 1.59 (s, 1H), 1.68 (t, J=12.22 Hz, 4H), 1.87 (s, 3H), 2.23 (s, 3H), 3.86 (d, J=8.87 Hz, 1H), 4.52 (d, J=5.37 Hz, 2H), 7.14 (t, J=8.60 Hz, 2H), 7.33-7.38 (m, 2H), 7.57 (d, J=7.52 Hz, 1H), 8.10 (s, 1H), 12.78 (bs, 1H); MS (ESI) m/z 329.2 (M+1)$^+$.

Example 10

N$^4$-cyclohexyl-5,6-dimethyl-N$^2$-[4-(trifluoromethoxy)benzyl]pyrimidine-2,4-diamine The titled compound was synthesized according to the general procedure described for preparation of N$^4$-cyclohexyl-5,6-dimethyl-N$^2$-(pyridin-2-ylmethyl)pyrimidine-2,4-diamine (Example 1) using [4-(trifluoromethoxy)benzyl]amine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 1.19-1.28 (m, 3H), 1.59 (d, J=13.59 Hz, 4H), 1.67 (s, 1H), 1.86 (s, 3H), 2.23 (s, 3H), 3.79 (s, 1H), 4.56 (d, J=5.04 Hz, 2H), 7.30 (d, J=8.11 Hz, 2H), 7.40-7.45 (m, 2H), 7.57 (d, J=7.23 Hz, 1H), 8.18 (t, J=5.26 Hz, 1H), 12.85 (bs, 1H); MS (ESI) m/z 394.8 (M+1)$^+$.

Example 11

N$^4$-cyclohexyl-N$^2$-(4-isopropylbenzyl)-5,6-dimethylpyrimidine-2,4-diamine

The titled compound was synthesized according to the general procedure described for preparation of N$^4$-cyclohexyl-5,6-dimethyl-N$^2$-(pyridin-2-ylmethyl)pyrimidine-2,4-diamine (Example 1) using (4-isopropylbenzyl)amine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 1.08 (d, J=15.04 Hz, 1H), 1.17 (d, J=6.72 Hz, 6H), 1.24-1.31 (m, 4H), 1.60 (s, 1H), 1.68 (t, J=11.95 Hz, 4H), 1.87 (s, 3H), 2.22 (s, 3H), 2.84 (t, J=13.90, 6.88 Hz, 1H), 3.89 (d, J=7.52 Hz, 1H), 4.48 (d, J=5.37 Hz, 2H), 7.14-7.28 (m, 4H), 7.55 (d, J=7.52 Hz, 1H), 8.06 (s, 1H), 12.69 (bs, 1H); MS (ESI) m/z 353.0 (M+1)$^+$.

Example 12

N$^4$-cyclohexyl-5,6-dimethyl-N$^2$-[4-(trifluoromethyl)benzyl]pyrimidine-2,4-diamine The titled compound was synthesized according to the general procedure described for preparation of N$^4$-cyclohexyl-5,6-dimethyl-N$^2$-(pyridin-2-ylmethyl)pyrimidine-2,4-diamine (Example 1) using [4-(trifluoromethyl)benzyl]amine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 1.12-1.21 (m, 5H), 1.44-1.59 (m, 5H), 1.86 (s, 3H), 2.24 (s, 3H), 3.71 (d, J=10.74 Hz, 1H), 4.62 (d, J=4.82 Hz, 2H), 7.50-7.58 (m, 3H), 7.67 (d, J=8.11 Hz, 2H), 8.20 (t, J=5.15 Hz, 1H), 12.99 (bs, 1H); MS (ESI) m/z 379.1 (M+1)$^+$.

Example 13

N$^4$-cyclohexyl-N$^2$-(3-fluorobenzyl)-5,6-dimethylpyrimidine-2,4-diamine

The titled compound was synthesized according to the general procedure described for preparation of N$^4$-cyclohexyl-5,6-dimethyl-N$^2$-(pyridin-2-ylmethyl)pyrimidine-2,4-diamine (Example 1) using (3-fluorobenzyl)amine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 1.08 (t, J=13.57 Hz, 1H), 1.19-1.31 (m, 4H), 1.58-1.70 (m, 5H), 1.87 (s, 3H), 2.22 (s, 3H), 3.82 (d, J=6.98 Hz, 1H), 4.53 (d, J=5.91 Hz, 2H), 7.01-7.11 (m, 2H), 7.14 (d, J=7.25 Hz, 2H), 7.32-7.39 (m, 1H), 7.56 (d, J=7.79 Hz, 1H), 8.35 (s, 1H), 12.47 (s, 1H); MS (ESI) m/z 329.0 (M+1)$^+$.

Example 14

N⁴-cyclohexyl-5,6-dimethyl-N²-(1H-pyrazol-5-ylmethyl)pyrimidine-2,4-diamine

The titled compound was synthesized according to the general procedure described for preparation of N⁴-cyclohexyl-5,6-dimethyl-N²-(pyridin-2-ylmethyl)pyrimidine-2,4-diamine (Example 1) using (1H-pyrazol-5-ylmethyl)amine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a light-yellow solid. $^1$H NMR (300 MHz, DMSO-$d_6$) δ ppm 1.28-1.37 (m, 5H), 1.60-1.69 (m, 5H), 1.86 (s, 3H), 2.25 (s, 3H), 3.98 (d, J=10.74 Hz, 1H), 4.52 (d, J=4.82 Hz, 2H), 6.12 (s, 1H), 7.59 (s, 1H), 7.98 (s, 1H), 12.15 (bs, 1H); MS (ESI) m/z 301.5 (M+1)⁺.

Example 15

N⁴-cyclohexyl-5,6-dimethyl-N²-[(1R)-1-phenylethyl]pyrimidine-2,4-diamine

The titled compound was synthesized according to the general procedure described for preparation of N⁴-cyclohexyl-5,6-dimethyl-N²-(pyridin-2-ylmethyl)pyrimidine-2,4-diamine (Example 1) using [(1R)-1-phenylethyl]amine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a light-yellow solid. $^1$H NMR (300 MHz, DMSO-$d_6$) δ ppm 1.03-1.87 (m, 16H), 2.13 (s, 3H), 3.80 (s, 1H), 4.95-5.02 (m, 1H), 6.73 (s, 1H), 7.14-7.41 (m, 5H), 8.38 (s, 1H); MS (ESI) m/z 325.1 (M+1)⁺.

Example 16

N⁴-cyclohexyl-5,6-dimethyl-N²-[(1S)-1-phenylethyl]pyrimidine-2,4-diamine

The titled compound was synthesized according to the general procedure described for preparation of N⁴-cyclohexyl-5,6-dimethyl-N²-(pyridin-2-ylmethyl)pyrimidine-2,4-diamine (Example 1) using [(1S)-1-phenylethyl]amine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a light-yellow solid. $^1$H NMR (300 MHz, DMSO-$d_6$) δ ppm 1.03-1.87 (m, 16H), 2.13 (s, 3H), 3.80 (s, 1H), 4.95-5.02 (m, 1H), 6.73 (s, 1H), 7.14-7.41 (m, 5H), 8.38 (s, 1H); MS (ESI) m/z 325.8 (M+1)⁺.

Example 17

N⁴-cyclohexyl-5,6-dimethyl-N²-[(4-methylpyridin-2-yl)methyl]pyrimidine-2,4-diamine The titled compound was synthesized according to the general procedure described for preparation of N⁴-cyclohexyl-5,6-dimethyl-N²-(pyridin-2-ylmethyl)pyrimidine-2,4-diamine (Example 1) using (4-methylpyridin-2-yl)methanamine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a light-grey solid. $^1$H NMR (300 MHz, DMSO-$d_6$) δ ppm 0.92-1.67 (m, 10H), 1.88 (s, 3H), 2.28 (s, 3H), 2.53 (s, 3H), 3.63 (bs, 1H), 4.92 (d, J=4.30 Hz, 2H), 7.60-7.80 (m, 3H), 8.19 (bs, 1H), 8.66 (d, J=5.64 Hz, 1H), 13.34 (s, 1H); MS (ESI) m/z 326.0 (M+1)⁺.

Example 18

N⁴-cyclohexyl-N²-[(4-methoxypyridin-2-yl)methyl]-5,6-dimethylpyrimidine-2,4-diamine The titled compound was synthesized according to the general procedure described for preparation of N⁴-cyclohexyl-5,6-dimethyl-N²-(pyridin-2-ylmethyl)pyrimidine-2,4-diamine (Example 1) using [(4-methoxypyridin-2-yl)methyl]amine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a light-grey solid. $^1$H NMR (300 MHz, DMSO-$d_6$) δ ppm 1.07 (d, J=11.01 Hz, 3H), 1.23 (d, J=11.01 Hz, 2H), 1.47 (d, J=9.94 Hz, 2H), 1.60 (s, 3H), 1.88 (s, 3H), 2.25 (s, 3H), 4.73 (d, J=5.37 Hz, 2H), 7.22-7.29 (m, 2H), 7.59 (d, J=7.79 Hz, 1H), 8.53-8.56 (m, 2H), 12.88 (bs, 1H); MS (ESI) m/z 342.7 (M+1)⁺.

Example 19

N⁴-cyclohexyl-5,6-dimethyl-N²-[(6-methylpyridin-2-yl)methyl]pyrimidine-2,4-diamine The titled compound was synthesized according to the general procedure described for preparation of N⁴-cyclohexyl-5,6-dimethyl-N²-(pyridin-2-ylmethyl)pyrimidine-2,4-diamine (Example 1) using [(6-methylpyridin-2-yl)methyl]amine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a light-grey solid. $^1$H NMR (300 MHz, DMSO-$d_6$) δ ppm 1.13-1.18 (m, 5H), 1.56-1.59 (m, 5H), 1.87 (s, 3H), 2.21 (s, 3H), 2.49 (s, 3H), 3.63 (d, J=6.72 Hz, 1H), 4.62 (d, J=4.30 Hz, 2H), 7.21-7.23 (m, 2H), 7.56 (d, J=5.64 Hz, 1H), 7.76-7.80 (m, 1H), 8.24 (s, 1H), 12.39 (s, 1H); MS (ESI) m/z 326.5 (M+1)⁺.

Example 20

N⁴-cyclohexyl-5,6-dimethyl-N²-{[5-(trifluoromethyl)pyridin-2-yl]methyl}pyrimidine-2,4-diamine The titled compound was synthesized according to the general procedure described for preparation of N⁴-cyclohexyl-5,6-dimethyl-N²-(pyridin-2-ylmethyl)pyrimidine-2,4-diamine (Example 1) using {[5-(trifluoromethyl)pyridin-2-yl]methyl}amine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a light-grey solid. $^1$H NMR (300 MHz, DMSO-$d_6$) δ ppm 1.04-1.16 (m, 3H), 1.16-1.19 (m, 2H), 1.38 (d, J=10.21 Hz, 2H), 1.55 (s, 3H), 1.86 (s, 3H), 2.26 (bs, 3H) 3.53 (d, J=5.37 Hz, 1H), 4.73 (s, 2H), 7.53 (d, J=7.52 Hz, 2H), 8.15 (d, J=7.79 Hz, 2H), 8.89 (s, 1H), 12.98 (bs, 1H); MS (ESI) m/z 380.0 (M+1)$^+$.

Example 21

N$^2$-[(4-tert-butylpyridin-2-yl)methyl]-N$^4$-cyclohexyl-5,6-dimethylpyrimidine-2,4-diamine The titled compound was synthesized according to the general procedure described for preparation of N$^4$-cyclohexyl-5,6-dimethyl-N$^2$-(pyridin-2-ylmethyl)pyrimidine-2,4-diamine (Example 1) using [(4-tert-butylpyridin-2-yl)methyl]amine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a light-grey solid. $^1$H NMR (300 MHz, DMSO-$d_6$) δ ppm 1.02-1.10 (m, 3H), 1.24 (d, J=11.01 Hz, 11H), 1.42 (d, J=10.48 Hz, 2H), 1.55 (d, J=9.94 Hz, 3H), 1.90 (s, 3H) 2.29 (s, 3H), 3.43 (s, 1H), 4.71 (d, J=5.10 Hz, 2H), 7.52 (s, 2H) 7.59 (d, J=7.52 Hz, 1H), 8.21 (s, 1H), 8.53 (d, J=6.72 Hz, 1H), 12.48 (s, 1H); MS (ESI) m/z 368.1 (M+1)$^+$.

Example 22

N$^4$-cyclohexyl-5,6-dimethyl-N$^2$-(2-thienylmethyl)pyrimidine-2,4-diamine

The titled compound was synthesized according to the general procedure described for preparation of N$^4$-cyclohexyl-5,6-dimethyl-N$^2$-(pyridin-2-ylmethyl)pyrimidine-2,4-diamine (Example 1) using (2-thienylmethyl)amine instead of (pyridin-2-ylmethyl)amine. The crude product was purified by crystallization from ethanol (10 mL) to afford the titled compound as the hydrochloride salt as a light-grey solid. $^1$H NMR (300 MHz, DMSO-$d_6$) δ ppm 1.20-1.35 (m, 5H), 1.65-1.79 (m, 5H), 1.89 (s, 3H), 2.23 (s, 3H), 4.08 (bs, 1H), 4.71 (d, J=4.57 Hz, 2H), 6.96 (s, 1H), 7.05 (s, 1H), 7.40 (d, J=4.57 Hz, 1H), 7.70 (d, J=6.72 Hz, 1H), 8.07 (s, 1H); MS (ESI) m/z 317.7 (M+1)$^+$.

Example 23

N$^4$-cyclohexyl-N$^2$-[(3,5-dimethyl-1,2-oxazol-4-yl)methyl]-5,6-dimethylpyrimidine-2,4-diamine The titled compound was synthesized according to the general procedure described for preparation of N$^4$-cyclohexyl-5,6-dimethyl-N$^2$-(pyridin-2-ylmethyl)pyrimidine-2,4-diamine (Example 1) using [(3,5-dimethylisoxazol-4-yl)methyl]amine instead of (pyridin-2-ylmethyl)amine. The product was purified by HPLC (column: YMC-PACK ODS-AQ C18, 250 mm×20 mm, 10 μm; gradient: 20-50% acetonitrile in 0.02% trifluoroacetic acid/water over fifteen minutes; 50-100% acetonitrile in 0.02% trifluoroacetic acid/water over five minutes; flow rate: 25 mL/min; temperature: 25° C.) to afford the titled compound as the trifluoroacetate salt as a white solid. $^1$H NMR (300 MHz, DMSO-$d_6$) δ ppm 1.23-1.40 (m, 5H), 1.70 (d, J=12.90 Hz, 1H), 1.75-1.82 (m, 2H), 1.91 (s, 3H), 2.00 (d, J=12.63 Hz, 2H), 2.32 (d, J=9.40 Hz, 6H), 2.43 (s, 3H), 4.05-4.10 (m, 1H), 4.38 (d, J=5.64 Hz, 2H), 5.21 (d, J=7.79 Hz, 1H), 9.64 (s, 1H), 14.01 (s, 1H); MS (ESI) m/z 330.9 (M+1)$^+$.

Example 24

N$^4$-cyclohexyl-5,6-dimethyl-N$^2$-[(1-methyl-1H-imidazol-4-yl)methyl]pyrimidine-2,4-diamine The titled compound was synthesized according to the general procedure described for preparation of N$^4$-cyclohexyl-5,6-dimethyl-N$^2$-(pyridin-2-ylmethyl)pyrimidine-2,4-diamine (Example 1) using [(1-methyl-1H-imidazol-4-yl)methyl]amine instead of (pyridin-2-ylmethyl)amine. The product was purified by crystallization from ethanol (10 mL) to afford the titled compound as the hydrochloride salt as a white solid. $^1$H NMR (300 MHz, methanol-$d_4$) δ ppm 1.25-1.38 (m, 5H), 1.70-1.85 (m, 5H), 1.97 (s, 3H), 2.30 (s, 3H) 2.71 (s, 1H), 3.72 (s, 3H), 4.08 (s, 1H), 4.53 (s, 2H), 7.07 (s, 1H), 7.72 (s, 1H); MS m/z 315.7 (M+1)$^+$.

Example 25

N$^4$-cyclohexyl-N$^2$-(3-methoxybenzyl)-5,6-dimethylpyrimidine-2,4-diamine

The titled compound was synthesized according to the general procedure described for preparation of N$^4$-cyclohexyl-5,6-dimethyl-N$^2$-(pyridin-2-ylmethyl)pyrimidine-2,4-diamine (Example 1) using (3-methoxybenzyl)amine instead of (pyridin-2-ylmethyl)amine. The crude product was purified by crystallization from ethanol (10 mL) to afford the titled compound as the hydrochloride salt as a white solid. $^1$H NMR (300 MHz, DMSO-$d_6$) δ ppm 1.15-1.28 (m, 5H), 1.60-1.80 (m, 5H), 1.87 (s, 3H), 2.21 (s, 3H), 3.72 (s, 3H), 3.86 (s, 1H), 4.48 (d, J=5.64 Hz, 2H), 6.75-6.89 (m, 3H), 7.23 (t, J=7.93 Hz, 1H), 7.56 (d, J=7.52 Hz, 1H), 8.40-8.55 (m, J=38.95 Hz, 1H), 12.56 (s, 1H); MS (ESI) m/z 341.5 (M+1)$^+$.

Example 26

N$^4$-cyclohexyl-5,6-dimethyl-N$^2$-[(3-methylpyridin-2-yl)methyl]pyrimidine-2,4-diamine The titled compound was synthesized according to the general procedure described for preparation of N$^4$-cyclohexyl-5,6-dimethyl-N$^2$-(pyridin-2-ylmethyl)pyrimidine-2,4-diamine (Example 1) using [(3-methylpyridin-2-yl)methyl]amine instead of (pyridin-2-ylmethyl)amine. The crude product was purified by crystallization from ethanol (10 mL) to afford the titled compound as the hydrochloride salt as a white solid. $^1$H NMR (300 MHz, DMSO-$d_6$) δ ppm 1.10-1.20 (m, 5H), 1.55-1.75 (m, 5H), 1.89 (s, 3H), 2.25 (s, 3H), 2.33 (s, 3H), 3.83 (s, 1H), 4.63 (d, J=5.10 Hz, 2H), 7.15-7.25 (m, 1H), 7.50-7.65 (m, 2H), 7.91 (s, 1H), 8.34 (d, J=4.03 Hz, 1H), 12.62 (s, 1H); MS (ESI) m/z 326.9 (M+1)$^+$.

Example 27

N$^2$-[(4-chloropyridin-2-yl)methyl]-N$^4$-cyclohexyl-5,6-dimethylpyrimidine-2,4-diamine The titled compound was synthesized according to the general procedure described for preparation of N$^4$-cyclohexyl-5,6-dimethyl-N$^2$-(pyridin-2-ylmethyl)pyrimidine-2,4-diamine (Example 1) using [(4-chloropyridin-2-yl)

methyl]amine instead of (pyridin-2-ylmethyl)amine. The crude product was purified by crystallization from ethanol (10 mL) to afford the titled compound as the hydrochloride salt as a white solid. $^1$H NMR (300 MHz, methanol-$d_4$) δ ppm 1.16-1.28 (m, 5H), 1.55-1.75 (m, 5H), 1.96 (s, 3H), 2.32 (s, 3H), 3.80 (s, 1H), 4.70 (s, 2H), 7.39 (d, J=3.76 Hz, 1H), 7.48 (s, 1H), 8.46 (d, J=5.10 Hz, 1H); MS (ESI) m/z 346.0, 348.1 (M+1)$^+$.

Example 28

$N^4$-(4,4-difluorocyclohexyl)-5,6-dimethyl-$N^2$-[(4-methylpyridin-2-yl)methyl]pyrimidine-2,4-diamine Step A 2-chloro-N-(4,4-difluorocyclohexyl)-5,6-dimethyl-pyrimidin-4-amine To the solution of 2,4-dichloro-5,6-dimethylpyrimidine (0.585 g, 3.304 mmol, Example 1, Step C) in N,N-dimethylformamide (10 mL), (4,4-difluorocyclohexyl)amine hydrochloride (0.652 g, 3.800 mmol) and triethylamine (1.338 g, 13.218 mmol) were added, and reaction mixture was heated at 50° C. overnight. Volatiles were removed under reduced pressure, and the residue was poured into water (300 mL). The mixture was extracted with ether (3×50 mL), dried over sodium sulfate, filtered, and concentrated. The residue was subjected to column chromatography on silica eluting with a mixture of hexane/ethyl acetate (gradient 4:1-2:1) to provide 621 mg (68%) of the titled compound as a white solid. $^1$H NMR (300 MHz, DMSO-$d_6$) δ ppm 1.18-1.24 (m, 1H), 1.60-1.72 (m, 2H), 1.80-2.10 (m, 8H) 2.21 (s, 3H), 4.00-4.10 (m, 1H), 6.73 (d, J=7.79 Hz, 1H); MS (ESI) m/z 318.6 (M+1)$^+$.

Step B $N^4$-(4,4-difluorocyclohexyl)-5,6-dimethyl-$N^2$-[(4-methylpyridin-2-yl)methyl]pyrimidine-2,4-diamine The titled compound was synthesized according to the general procedure described for preparation of $N^4$-cyclohexyl-5,6-dimethyl-$N^2$-(pyridin-2-ylmethyl)pyrimidine-2,4-diamine (Example 1) using [(4-methylpyridin-2-yl)methyl]amine instead of (pyridin-2-ylmethyl)amine and 2-chloro-N-(4,4-difluorocyclohexyl)-5,6-dimethylpyrimidin-4-amine (Step A) instead of 2-chloro-N-cyclohexyl-5,6-dimethylpyrimidin-4-amine. The product was purified by crystallization from ethanol to afford the titled compound (45% yield) as the hydrochloride salt as a light-yellow solid. $^1$H NMR (300 MHz, DMSO-$d_6$) δ ppm 1.45-1.55 (m, 4H), 1.80-2.05 (m, 7H), 2.28 (s, 3H), 2.52 (s, 3H), 4.05 (bs, 1H), 4.99 (d, J=5.37 Hz, 2H), 7.65-7.78 (m, 3H) 8.31 (s, 1H), 8.67 (d, J=5.91 Hz, 1H), 13.42 (s, 1H); MS (ESI) m/z 362.4 (M+1)$^+$.

Example 29

$N^4$-cyclopentyl-5,6-dimethyl-$N^2$-(pyridin-2-ylmethyl)pyrimidine-2,4-diamine

Step A 5,6-dimethyl-2-(methylthio)pyrimidin-4(3H)-one

To a stirred solution of 5,6-dimethyl-2-thioxo-2,3-dihydropyrimidin-4(1H)-one (10.0 g, 64.0 mmol, Example 1, Step A) and sodium hydroxide (10.0 g, 260.0 mmol) in water (150 mL) at ambient temperature was added methyl iodide (15.0 g, 320.0 mmol), and the reaction mixture was stirred at ambient temperature overnight. Then the reaction mixture was acidified with acetic acid (50 mL), and the solid was collected by filtration and dried to afford 7.0 g (64%) of the titled compound as a white solid. $^1$H NMR (300 MHz, DMSO-$d_6$) δ ppm 1.87 (s, 3H), 2.18 (s, 3H), 2.45 (s, 3H), 12.38 (bs, 1H).

Step B 5,6-dimethyl-2-[(pyridin-2-ylmethyl)amino]pyrimidin-4(3H)-one

To a stirred solution of (pyridin-2-ylmethyl)amine (5.8 g, 54 mmol) in dimethyl sulfoxide (15 mL) at ambient temperature was added 5,6-dimethyl-2-(methylthio)pyrimidin-4(3H)-one (7 g, 41 mmol, Step A), and the resulting mixture was stirred at 150° C. overnight. Then water (100 mL) was added carefully into the hot reaction mixture. Upon cooling to ambient temperature, diethyl ether (30 mL) was added. The formed precipitate was collected by filtration and dried to afford 7.0 g (74%) of the titled product as a white solid. $^1$H NMR (300 MHz, DMSO-$d_6$) δ ppm 1.77 (s, 3H), 2.04 (s, 3H), 4.55 (s, 2H), 6.81 (bs, 1H), 7.23-7.40 (m, 2H), 7.77 (t, J=7.5 Hz, 1H), 8.53 (bs, 1H), 10.84 (bs, 1H).

Step C 4-chloro-5,6-dimethyl-N-(pyridin-2-ylmethyl)pyrimidin-2-amine

A solution of 5,6-dimethyl-2-[(pyridin-2-ylmethyl)amino]pyrimidin-4(3H)-one (7.0 g, 32.6 mmol, Step B) in phosphorus (V) oxychloride (30 mL) with addition of 1 drop of dimethylformamide was refluxed overnight under nitrogen. Then excess phosphorus (V) oxychloride was removed under reduced pressure. Toluene (30 mL) was added, and the reaction mixture was evaporated under reduced pressure. The residue was diluted with 5% aqueous sodium bicarbonate (100 mL) and extracted with ethyl acetate (2×200 mL). The solvent was evaporated under reduced pressure, and the residue was subjected to column chromatography eluted with hexane/ethyl acetate (2:1). The titled compound 6.1 g (74%) was obtained as a light-yellow solid. $^1$H NMR (300 MHz, DMSO-$d_6$) δ ppm 2.10 (s, 3H), 2.39 (s, 3H), 4.54 (s, 2H), 7.20-7.30 (m, 2H), 7.68-7.76 (m, 2H), 7.76 (bs, 1H).

Step D $N^4$-cyclopentyl-5,6-dimethyl-$N^2$-(pyridin-2-ylmethyl)pyrimidine-2,4-diamine A solution of 4-chloro-5,6-dimethyl-N-(pyridin-2-ylmethyl)pyrimidin-2-amine (200 mg, 0.8 mmol, Step C) and cyclopentanamine (85 mg, 1 mmol) in acetonitrile (5 mL) was treated with 3.5 M hydrogen chloride in dioxane (0.2 mL), and the resultant mixture was refluxed overnight. The reaction mixture was diluted with water (50 mL), and the resultant precipitate was collected by filtration. The precipitate was purified by crystallization from ethanol (10 mL) to afford 42 mg (19%) of the titled compound as the hydrochloride salt as a white solid. $^1$H NMR (300 MHz, DMSO-$d_6$) δ ppm 1.40-1.50 (m, 4H), 1.50-1.67 (m, 4H), 1.88 (s, 3H), 2.27 (s, 3H), 4.00-4.12 (m, 1H), 4.92 (d, J=4.57 Hz, 2H), 7.71-4.83 (m, 2H), 7.83 (d, J=8.06 Hz, 1H), 8.17-8.25

(m, 1H), 8.33-8.39 (m, 1H), 8.76 (d, J=5.10 Hz, 1H), 13.24 (bs, 1H); MS (ESI) m/z 398.5 (ESI) (M+1)$^+$.

Example 30

5,6-dimethyl-N$^2$-(pyridin-2-ylmethyl)-N$^4$-(tetrahydro-2H-pyran-4-yl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using tetrahydro-2H-pyran-4-amine instead of cyclopentanamine. The crude material was purified by column chromatography eluting with mixture of chloroform/ethanol/20% water solution of ammonia (200:10:1), and then the final product was washed with diethyl ether to afford the titled compound as a light-yellow solid. $^1$H NMR (300 MHz, DMSO-d$_6$) δ ppm 1.39 (bs, 2H), 1.52 (bs, 2H), 1.79 (d, J=16.39 Hz, 3H), 2.06 (d, J=8.87 Hz, 3H), 3.17 (d, J=11.01 Hz, 2H), 3.74 (d, 2H), 3.85 (bs, 1H), 4.44 (d, J=6.18 Hz, 2H), 5.81 (d, J=7.52 Hz, 1H), 6.73 (s, 1H), 7.12-7.16 (m, 1H), 7.23 (d, J=7.79 Hz, 1H), 7.65 (t, J=7.66 Hz, 1H), 8.45 (d, J=4.84 Hz, 1H); MS (ESI) m/z 314.4 (M+1)$^+$.

Example 31

5,6-dimethyl-N$^2$-(pyridin-2-ylmethyl)-N$^4$-[4-(trifluoromethyl)cyclohexyl]pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using 4-(trifluoromethyl)cyclohexanamine instead of cyclopentanamine. The crude material was purified by HPLC (column: YMC-PACK ODS-AQ C18, 250 mm×20 mm, 10 μm; gradient: 20-50% acetonitrile in 0.02% trifluoroacetic acid/water over fifteen minutes; 50-100% acetonitrile in 0.02% trifluoroacetic acid/water over five minutes; flow rate: 25 mL/min; temperature: 25° C.) to afford the titled compound as the trifluoroacetate as a white solid. $^1$H NMR (300 MHz, DMSO-d$_6$) δ ppm 1.19 (d, J=10.30 Hz, 2H), 1.28-1.36 (m, 2H), 1.50-1.62 (m, 2H), 1.78 (d, J=5 Hz, 2H), 1.88 (s, 3H), 2.10-2.22 (m, 1H), 2.25 (s, 3H), 3.60-3.68 (m, 1H), 4.69 (d, J=5.04 Hz, 2H), 7.36-7.49 (m, 2H), 7.66 (d, J=7.72 Hz, 1H), 7.90 (t, J=7.72 Hz, 1H), 8.39-8.43 (m, 1H), 8.56 (d, J=4.60 Hz, 1H), 12.66 (bs, 1H); MS (ESI) m/z 380.8 (M+1)$^+$.

Example 32

N$^4$-(4,4-difluorocyclohexyl)-5,6-dimethyl-N$^2$-(pyridin-2-ylmethyl)pyrimidine-2,4-diamine A solution of 4-chloro-5,6-dimethyl-N-(pyridin-2-ylmethyl)pyrimidin-2-amine (200 mg, 0.8 mmol, Example 29, Step C) and (4,4-difluorocyclohexyl)amine hydrochloride (172 mg, 1 mmol) in acetonitrile (5 mL) was refluxed overnight. The reaction mixture was diluted with water (50 mL) and a formed precipitate was collected by filtration. The crude material was purified by HPLC (column: YMC-PACK ODS-AQ C18, 250 mm×20 mm, 10 μm; gradient: 20-50% acetonitrile in 0.02% trifluoroacetic acid/water over fifteen minutes; 50-100% acetonitrile in 0.02% trifluoroacetic acid/water over five minutes; flow rate: 25 mL/min; temperature: 25° C.) to afford 114 mg, 25% of the titled compound as the trifluoroacetic acid salt as a white solid. $^1$H NMR (300 MHz, DMSO-d$_6$) δ ppm 1.45-1.55 (m, 4H), 1.70-1.82 (m, 2H), 1.88 (s, 3H), 1.90-2.00 (m, 2H), 2.25 (s, 3H), 3.90 (bs, 1H), 4.70 (d, J=5.37 Hz, 2H), 7.38 (t, J=6.25 Hz, 1H), 7.47 (d, J=7.52 Hz, 1H), 7.64 (d, J=7.52 Hz, 1H), 7.90 (t, J=7.52 Hz, 1H), 8.46-8.52 (m, 1H), 8.57 (d, J=4.57 Hz, 1H), 12.78 (bs, 1H); MS (ESI) m/z 348.8 (M+1)$^+$. N$^4$-(4,4-Difluorocyclohexyl)-5,6-dimethyl-N$^2$-(pyridin-2-ylmethyl)pyrimidine-2,4-diamine trifluoroacetate was purified by column chromatography eluting with mixture of chloroform/ethanol/20% water solution of ammonia (200:10:1) to afford 58 mg (68%) of the titled compound as a white solid. $^1$H NMR (300 MHz, DMSO-d$_6$) δ ppm 1.40-1.51 (m, 2H), 1.60-1.71 (m, 3H), 1.81 (bs, 4H), 1.90-1.98 (m, 2H), 2.07 (s, 3H), 3.76-3.84 (m, 1H), 4.46 (d, J=5.91 Hz, 2H), 5.84 (d, J=7.25 Hz, 1H), 6.70-6.75 (m, 1H), 7.10-7.22 (m, 1H), 7.24 (d, J=7.79 Hz, 1H), 7.67 (t, J=7.52 Hz, 1H), 8.45 (d, J=4.30 Hz, 1H); MS (ESI) m/z 348.8 (M+1)$^+$.

Example 33

N$^4$-(2,3-dihydro-1H-inden-1-yl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using 2,3-dihydro-1H-inden-1-ylamineindan-1-amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 1.85 (bs, 4H), 2.11 (s, 3H), 2.20-2.28 (m, 1H), 2.70-2.76 (m, 1H), 2.85-2.95 (m, 1H), 4.40-4.52 (m, 2H), 5.60-5.65 (m, 1H), 6.37 (d, J=8.33 Hz, 1H), 6.71 (s, 1H), 7.06 (s, 2H), 7.10-7.22 (m, 3H), 7.28 (d, J=7.79 Hz, 1H), 7.68 (t, J=7.79 Hz, 1H), 8.42 (s, 1H); MS (ESI) m/z 346.1 (M+1)$^+$.

Example 34

3-({5,6-dimethyl-2-[(pyridin-2-ylmethyl)amino] pyrimidin-4-yl}amino)cyclopentanol The titled compound was synthesized according to the procedure described for preparation of N$^4$-cyclopentyl-5,6-dimethyl-N$^2$-(pyridin-2-ylmethyl)pyrimidine-2,4-diamine (Example 29) using 3-aminocyclopentanol hydrochloride instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, methanol-d$_4$) δ ppm 1.50-1.58 (m, 1H), 1.70-1.78 (m, 3H), 1.96 (bs, 4H), 2.34 (s, 3H), 3.32 (s, 3H), 4.20-4.32 (m, 2H), 7.69-7.75 (m, 1H), 7.79-7.85 (m, 1H), 8.20-8.29 (m, 1H), 8.69 (bs, 1H); MS (ESI) m/z 314.8 (M+1)$^+$.

Example 35

5,6-dimethyl-N$^2$-(pyridin-2-ylmethyl)-N$^4$-(1,2,3,4-tetrahydronaphthalen-1-yl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using 1,2,3,4-tetrahydronaphthalen-1-ylamine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-$d_6$) δ ppm 1.60-1.69 (m, 3H), 1.83 (bs, 4H), 2.09 (s, 3H), 2.66-2.75 (m, 2H), 4.46 (d, J=5.37 Hz, 2H), 5.31 (bs, 1H), 6.33 (d, J=8.33 Hz, 1H), 6.70-6.78 (m, 1H), 7.07 (dd, $J_1$=15.31 Hz, J2=6.45 Hz, 4H), 7.15 (d, J=5.64 Hz, 1H), 7.26 (d, J=7.52 Hz, 1H), 7.64 (d, J=7.25 Hz, 1H), 8.42 (d, J=4.03 Hz, 1H); MS (ESI) m/z 361.0 (M+1)$^+$.

Example 36

$N^4$-(3,4-dihydro-2H-chromen-4-yl)-5,6-dimethyl-$N^2$-(pyridin-2-ylmethyl)pyrimidine-2,4-diamine The titled compound was synthesized according to the procedure described for preparation of $N^4$-cyclopentyl-5,6-dimethyl-$N^2$-(pyridin-2-ylmethyl)pyrimidine-2,4-diamine (Example 29) using 3,4-dihydro-2H-chromen-4-ylamine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (400 MHz, CDCl$_3$) δ ppm 1.89 (s, 3H), 2.10 (bs, 1H), 2.42 (s, 3H), 4.11 (bs, 1H), 4.27 (bs, 1H), 4.93 (bs, 1H), 5.04 (bs, 1H), 5.31 (bs, 1H), 5.48 (bs, 1H), 6.75-6.88 (m, 3H), 7.20 (bs, 1H), 7.27 (bs, 1H), 7.42 (bs, 1H), 7.74 (bs, 1H), 8.02 (bs, 1H), 8.59 (bs, 1H), 10.63 (bs, 1H); MS (ESI) m/z 362.9 (M+1)$^+$.

Example 37 cis-4-({5,6-dimethyl-2-[(pyridin-2-ylmethyl)amino]pyrimidin-4-yl}amino)-1-methylcyclohexanol The titled compound was synthesized according to the procedure described for preparation of $N^4$-cyclopentyl-5,6-dimethyl-$N^2$-(pyridin-2-ylmethyl)pyrimidine-2,4-diamine (Example 29) using cis-4-amino-1-methylcyclohexanol instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (400 MHz, CDCl$_3$) δ ppm 1.25 (s, 3H), 1.29 (bs, 1H), 1.40-1.52 (m, 3H), 1.55-1.65 (m, 2H), 1.67-1.78 (m, 2H), 1.87 (s, 3H) 2.26 (s, 3H) 3.70-3.82 (m, 1H), 4.34 (d, J=7 Hz, 1H), 4.71 (d, J=5.4 Hz, 2H), 7.13 (t, J=5.64 Hz, 1H), 7.35 (d, J=8.06 Hz, 1H), 7.54-7.62 (m, 1H), 8.54 (d, J=4.56 Hz, 1H); MS (ESI) m/z 342.4 (M+1)$^+$.

Example 38 trans-4-({5,6-dimethyl-2-[(pyridin-2-ylmethyl)amino]pyrimidin-4-yl}amino)-1-methylcyclohexanol The titled compound was synthesized according to the procedure described for preparation of $N^4$-cyclopentyl-5,6-dimethyl-$N^2$-(pyridin-2-ylmethyl)pyrimidine-2,4-diamine (Example 29) using trans-4-amino-1-methylcyclohexanol instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (400 MHz, CDCl$_3$) δ ppm 1.16-1.32 (m, 5H), 1.38-1.46 (m, 2H), 1.48-1.59 (m, 2H), 1.80-1.90 (m, 2H), 1.92-1.99 (m, 3H), 2.01-2.12 (m, 2H), 2.25 (s, 3H), 3.90-3.96 (m, 1H), 4.20-4.31 (m, 1H), 4.43 (d, J=5.91 Hz, 2H), 5.50-5.62 (m, 1H), 7.20-7.26 (m, 1H), 7.34 (d, J=7.79 Hz, 1H), 7.56 (dd, $J_1$=7.76 Hz, $J_1$=1.07, Hz, 1H), 8.54 (d, J=4.83 Hz, 1H); MS (ESI) m/z 342.8 (M+1)$^+$.

Example 39

$N^4$-(bicyclo[2.2.1]hept-2-yl)-5,6-dimethyl-$N^2$-(pyridin-2-ylmethyl)pyrimidine-2,4-diamine The titled compound was synthesized according to the procedure described for preparation of $N^4$-cyclopentyl-5,6-dimethyl-$N^2$-(pyridin-2-ylmethyl)pyrimidine-2,4-diamine (Example 29) using bicyclo[2.2.1]hept-2-ylamine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-$d_6$) δ ppm 0.80-0.94 (m, 1H), 0.98-1.06 (m, 1H), 1.10-1.19 (m, 1H), 1.26-1.36 (m, 2H), 1.48-1.56 (m, 1H), 1.65-1.77 (m, 1H), 1.93 (s, 3H), 2.07 (s, 3H), 2.12-2.20 (m, 1H), 2.22-2.30 (m, 1H), 2.50-2.58 (m, 1H), 3.70-3.80 (m, 1H) 4.42-4.51 (m, 2H), 7.20-7.27 (m, 1H) 7.50-7.58 (m, 1H), 7.68-7.80 (m, 1H), 8.65 (d, J=4.92 Hz, 1H); MS (ESI) m/z 324.0 (M+1)$^+$.

Example 40

5,6-dimethyl-$N^4$-(2-methylcyclohexyl)-$N^2$-(pyridin-2-ylmethyl)pyrimidine-2,4-diamine The titled compound was synthesized according to the procedure described for preparation of $N^4$-cyclopentyl-5,6-dimethyl-$N^2$-(pyridin-2-ylmethyl)pyrimidine-2,4-diamine (Example 29) using 2-methylcyclohexanamine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (400 MHz, CDCl$_3$) δ ppm 0.93 (bs, 3H), 1.28-1.42 (m, 6H), 1.62-1.70 (m, 1H), 1.78-1.89 (m, 2H), 1.93 (s, 3H), 2.07 (s, 3H), 2.95-3.04 (m, 1H), 4.43 (bs, 2H), 7.22 (t, J=7.30 Hz, 1H), 7.56 (d, J=7.76 Hz, 1H), 7.68-7.75 (m, 1H), 8.65 (d, J=4.92 Hz, 1H); MS (ESI) m/z 326.4.0 (M+1)$^+$.

Example 41

$N^4$-(2,3-dimethylcyclohexyl)-5,6-dimethyl-$N^2$-(pyridin-2-ylmethyl)pyrimidine-2,4-diamine The titled compound was synthesized according to the procedure described for preparation of $N^4$-cyclopentyl-5,6-dimethyl-$N^2$-(pyridin-2-ylmethyl)pyrimidine-2,4-diamine (Example 29) using 2,3-dimethylcyclohexanamine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (400 MHz, CDCl$_3$) δ ppm 0.75-0.76 (m, 3H), 0.85-0.95 (m, 3H), 1.55-1.74 (m, 8H), 1.86-1.97 (m, 4H), 2.07 (s, 3H), 3.10-

3.18 (m, 1H), 4.43 (bs, 2H), 7.20-7.26 (m, 1H), 7.50-7.57 (m, 1H), 7.67-7.73 (m, 1H), 8.60-7.68 (m, 1H); MS (ESI) m/z 340.4 (M+1)$^+$.

Example 42

2-({5,6-dimethyl-2-[(pyridin-2-ylmethyl)amino] pyrimidin-4-yl}amino)cyclohexanol The titled compound was synthesized according to the procedure described for preparation of N$^4$-cyclopentyl-5,6-dimethyl-N$^2$-(pyridin-2-ylmethyl)pyrimidine-2,4-diamine (Example 29) using 2-aminocyclohexanol instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (400 MHz, methanol-d$_6$) δ ppm 1.16-1.22 (m, 1H), 1.30-1.41 (m, 3H), 1.50-162 (m, 3H), 1.68-1.74 (m, 1H), 1.91 (s, 3H), 2.20 (s, 3H), 3.72 (bs, 1H), 3.79 (bs, 1H), 4.61 (bs, 2H), 7.18-7.26 (m, 1H), 7.34-7.45 (m, 1H), 7.70-7.82 (m, 1H), 8.47 (bs, 1H); MS (ESI) m/z 328.8 (M+1)$^+$.

Example 43 rac-[(1R,2S)-2-({5,6-dimethyl-2-[(pyridin-2-ylmethyl)amino]pyrimidin-4-yl}amino)cyclohexyl] methanol The titled compound was synthesized according to the procedure described for preparation of N$^4$-cyclopentyl-5,6-dimethyl-N$^2$-(pyridin-2-ylmethyl)pyrimidine-2,4-diamine (Example 29) using rac-[(1R,2S)-2-aminocyclohexyl] methanol instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (400 MHz, methanol-d$_6$) δ ppm 1.35 (bs, 2H), 1.50 (bs, 6H), 1.89 (bs, 3H), 2.20 (bs, 3H), 3.40-3.48 (m, 1H), 3.60-3.68 (m, 1H), 4.10-4.18 (m, 1H), 4.64 (bs, 2H), 7.26 (t, J=5.64 Hz, 1H), 7.40 (d, J=8.06 Hz, 1H), 7.75 (d, J=7.79 Hz, 1H), 8.46 (d, J=4.83, 1H); MS (ESI) m/z 342.8 (M+1)$^+$.

Example 44

N$^4$-(cyclopentylmethyl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using (cyclopentylmethyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 1.00-1.09 (m, 2H), 1.30-1.38 (m, 2H), 1.38-1.49 (m, 4H), 1.80-1.94 (m, 4H), 2.26 (s, 3H), 3.14 (bs, 2H), 4.70 (bs, 2H), 7.37-7.42 (m, 2H), 7.91 (t, J=7.52, 1H), 8.09-8.13 (m, 1H), 8.43 (s, 1H), 8.55-8.62 (m, 1H), 12.65 (bs, 1H); MS (ESI) m/z 312.8 (M+1)$^+$.

Example 45

N$^4$-cycloheptyl-5,6-dimethyl-N$^2$-(pyridin-2-ylmethyl)pyrimidine-2,4-diamine

The titled compound was synthesized according to the procedure described for preparation of N$^4$-cyclopentyl-5,6-dimethyl-N$^2$-(pyridin-2-ylmethyl)pyrimidine-2,4-diamine (Example 29) using 1-cycloheptylamine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 1.26-1.32 (m, 2H), 1.38-1.50 (m, 8H), 1.68 (bs, 2H), 1.81 (s, 3H), 2.07 (s, 3H), 3.80-3.88 (m, 1H), 4.49 (d, J=9.91, 2H), 5.70 (d, J=7.25, H), 6.63 (brs, 1H), 7.15-7.20 (m, 1H), 7.21-7.28 (m, 1H), 7.68 (t, J=7.25, 1H), 8.46 (bs, 1H); MS (ESI) m/z 326.9 (M+1)$^+$.

Example 46

N$^4$-(2,3-dihydro-1H-inden-2-yl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using 2,3-dihydro-1H-inden-2-ylamine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 1.86 (s, 3H), 2.11 (s, 3H), 2.76 (bs, 2H), 2.99 (bs, 2H), 4.49 (bs, 2H), 4.61 (bs, 1H), 6.23 (bs, 1H), 6.72-6.79 (m, 1H), 7.12 (bs, 4H), 7.216-7.23 (m, 1H), 7.21-7.29 (m, 1H), 7.65-7.73 (m, 1H), 8.41 (bs, 1H); MS (ESI) m/z 346.8 (M+1)$^+$.

Example 47

N$^4$-cyclobutyl-5,6-dimethyl-N$^2$-(pyridin-2-ylmethyl) pyrimidine-2,4-diamine

The titled compound was synthesized according to the procedure described for preparation of N$^4$-cyclopentyl-5,6-dimethyl-N$^2$-(pyridin-2-ylmethyl)pyrimidine-2,4-diamine (Example 29) using cyclobutanamine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (400 MHz, methanol-d$_4$) δ ppm 1.60-1.68 (m, 2H), 1.83-1.96 (m, 5H), 2.108-2.15 (m, 2H), 2.20 (s, 3H), 4.26-4.32 (m, 1H), 4.62 (bs, 2H), 7.28 (t, J=6.4 Hz, 1H), 7.41 (d, J=8.1 Hz, 1H), 7.76 (t, J=5.9 Hz, 1H), 8.47 (d, J=4.4 Hz, 1H); MS (ESI) m/z 284.2 (M+1)$^+$.

Example 48

5,6-dimethyl-N$^4$-(pentan-3-yl)-N$^2$-(pyridin-2-ylmethyl)pyrimidine-2,4-diamine The titled compound was synthesized according to the procedure described for preparation of N$^4$-cyclopentyl-5,6- dimethyl-N²-(pyridin-2-ylmethyl)pyrimidine-2,4-diamine (Example 29) using cyclobutanamine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 0.81 (t, J=7.3 Hz, 3H), 1.36-1.43 (m, 2H), 1.50-1.57 (m, 2H), 1.90 (s, 3H), 2.26 (s, 3H), 3.94-4.00 (m, 1H), 4.17 (bs, 1H), 4.72 (d, J=5.9 Hz, 2H), 5.72 (bs, 1H), 7.13 (t, J=7.5 Hz, 1H), 7.36 (d, J=7.3 Hz, 1H), 7.60 (t, J=7.5 Hz, 1H), 8.54 (d, J=4.8 Hz, 1H); MS (ESI) m/z 300.1 (M+1)$^+$.

Example 49

N⁴-(3-fluorophenyl)-5,6-dimethyl-N²-(pyridin-2-ylmethyl)pyrimidine-2,4-diamine

The titled compound was synthesized according to the procedure described for preparation of N⁴-cyclopentyl-5,6-dimethyl-N²-(pyridin-2-ylmethyl)pyrimidine-2,4-diamine (Example 29) using (3-fluorophenyl)amine hydrochloride instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 2.04 (s, 3H), 2.20 (s, 3H), 4.51 (d, J=5.6 Hz, 2H), 6.67 (t, J=5.9 Hz, 1H), 7.05-7.29 (m, 4H), 7.60 (bs, 1H), 7.69 (t, J=8.1 Hz, 1H), 8.08 (s, 1H), 8.48 (d, J=4.0 Hz, 1H); MS (ESI) m/z 324.4 (M+1)$^+$.

Example 50

N⁴-(4-fluorophenyl)-5,6-dimethyl-N²-(pyridin-2-ylmethyl)pyrimidine-2,4-diamine

The titled compound was synthesized according to the procedure described for preparation of N⁴-cyclopentyl-5,6-dimethyl-N²-(pyridin-2-ylmethyl)pyrimidine-2,4-diamine (Example 29) using (4-fluorophenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.07 (s, 3H), 2.34 (s, 3H), 4.69 (d, J=5.9 Hz, 2H), 5.98 (bs, 1H), 6.32 (s, 1H), 6.94 (t, J=8.3 Hz, 1H), 7.16 (t, J=7.5 Hz, 1H), 7.31 (d, J=7.6 Hz, 1H), 7.36-7.42 (m, 2H), 7.61 (t, J=7.5 Hz, 1H), 8.58 (d, J=5.4 Hz, 1H); MS (ESI) m/z 324.0 (M+1)$^+$.

Example 51

N⁴-(2-fluorophenyl)-5,6-dimethyl-N²-(pyridin-2-ylmethyl)pyrimidine-2,4-diamine

The titled compound was synthesized according to the procedure described for preparation of N⁴-cyclopentyl-5,6-dimethyl-N²-(pyridin-2-ylmethyl)pyrimidine-2,4-diamine (Example 29) using (2-fluorophenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 2.03 (s, 3H), 2.18 (s, 3H), 4.38 (bs, 2H), 6.84 (bs, 1H), 6.96-7.22 (m, 5H), 7.45-7.78 (m, 3H), 8.15 (bs, 1H); MS (ESI) m/z 324.5 (M+1)$^+$.

Example 52

5,6-dimethyl-N⁴-phenyl-N²-(pyridin-2-ylmethyl)pyrimidine-2,4-diamine

The titled compound was synthesized according to the procedure described for preparation of N⁴-cyclopentyl-5,6-dimethyl-N²-(pyridin-2-ylmethyl)pyrimidine-2,4-diamine (Example 29) using aniline instead of cyclopentanamine. The crude material was purified by column chromatography eluting with mixture of chloroform/ethanol/20% water solution of ammonia (200:10:1), and then the final product was washed with diethyl ether to afford the titled compound as a light-grey solid. $^1$H NMR (300 MHz, DMSO-d$_6$) δ ppm 2.03 (s, 3H), 2.19 (s, 3H), 4.48 (d, J=5.8 Hz, 2H), 6.88 (t, J=7.5 Hz, 1H), 6.95 (bs, 1H), 7.11 (bs, 2H), 7.20 (t, J=6.2 Hz, 1H), 7.26 (d, J=7.8 Hz, 1H), 7.52 (bs, 2H), 7.69 (t, J=6.9 Hz, 1H), 7.90 (s, 1H), 8.51 (d, J=4.3 Hz, 1H); MS (ESI) m/z 306.1 (M+1)$^+$.

Example 53

5,6-dimethyl-N²-(pyridin-2-ylmethyl)-N⁴-[3-(trifluoromethoxy)phenyl]pyrimidine-2,4-diamine The titled compound was synthesized according to the procedure described for preparation of N⁴-cyclopentyl-5,6-dimethyl-N²-(pyridin-2-ylmethyl)pyrimidine-2,4-diamine (Example 29) using [3-(trifluoromethoxy)phenyl]amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.09 (s, 3H), 2.35 (s, 3H), 4.73 (d, J=5.6 Hz, 2H), 6.08 (bs, 1H), 6.48 (bs, 1H), 6.88 (d, J=7.3 Hz, 1H), 7.16 (t, J=7.3 Hz, 1H), 7.22-7.34 (m, 3H), 7.62 (t, J=9.4 Hz, 1H), 7.75 (s, 1H), 8.57 (d, J=3.2 Hz, 1H); MS (ESI) m/z 390.7 (M+1)$^+$.

Example 54

5,6-dimethyl-N²-(pyridin-2-ylmethyl)-N⁴-[3-(trifluoromethyl)phenyl]pyrimidine-2,4-diamine The titled compound was synthesized according to the procedure described for preparation of N⁴-cyclopentyl-5,6-dimethyl-N²-(pyridin-2-ylmethyl)pyrimidine-2,4-diamine (Example 29) using [3-(trifluoromethyl)phenyl]amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.09 (s, 3H), 2.34 (s, 3H), 4.73 (d, J=5.6 Hz, 2H), 5.91 (bs, 1H), 6.47 (bs, 1H), 7.15 (t, J=8.2 Hz, 1H), 7.24-7.40 (m, 3H), 7.57-7.67 (m, 2H), 8.09 (s, 1H), 8.57 (d, J=2.4 Hz, 1H); MS (ESI) m/z 374.7 (M+1)$^+$.

Example 55

N⁴-(2,6-difluorophenyl)-5,6-dimethyl-N²-(pyridin-2-ylmethyl)pyrimidine-2,4-diamine The titled compound was synthesized according to the procedure described for preparation of N⁴-cyclopentyl-5,6- dimethyl-N²-(pyridin-2-ylmethyl)pyrimidine-2,4-diamine (Example 29) using (2,6-difluorophenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.11 (s, 3H), 2.33 (s, 3H), 4.50 (bs, 2H), 5.88 (bs, 2H), 6.80-7.01 (m, 2H), 7.03-7.21 (m, 3H), 7.53 (bs, 1H), 8.47 (bs, 1H); MS (ESI) m/z 342.6 (M+1)$^+$.

Example 56

5,6-dimethyl-N²-(pyridin-2-ylmethyl)-N⁴-[4-(trifluoromethoxy)phenyl]pyrimidine-2,4-diamine The titled compound was synthesized according to the procedure described for preparation of N⁴-cyclopentyl-5,6-dimethyl-N²-(pyridin-2-ylmethyl)pyrimidine-2,4-diamine (Example 29) using [4-(trifluoromethoxy)phenyl]amine instead of cyclopentanamine. The crude material was purified by column chromatography eluting with mixture of chloroform/ethanol/20% water solution of ammonia (200:10:1), and then the final product was washed with diethyl ether to afford the titled compound as a light-yellow solid. $^1$H NMR (300 MHz, CDCl$_3$) δ ppm 2.07 (s, 3H), 2.34 (s, 3H), 4.70 (d, J=3.6 Hz, 2H), 5.92 (bs, 1H), 6.44 (bs, 1H), 7.01-7.21 (m, 3H), 7.16 (bs, 1H), 7.44-7.61 (m, 3H), 8.58 (bs, 1H); MS (ESI) m/z 390.7 (M+1)$^+$.

Example 57

5,6-dimethyl-N²-(pyridin-2-ylmethyl)-N⁴-[4-(trifluoromethyl)phenyl]pyrimidine-2,4-diamine The titled compound was synthesized according to the procedure described for preparation of N⁴-cyclopentyl-5,6-dimethyl-N²-(pyridin-2-ylmethyl)pyrimidine-2,4-diamine (Example 29) using [4-(trifluoromethyl)phenyl]amine instead of cyclopentanamine. The crude material was purified by column chromatography eluting with mixture of chloroform/ethanol/20% water solution of ammonia (200:10:1), and then the final product was washed with diethyl ether to afford the titled compound as a light-yellow solid. $^1$H NMR (300 MHz, CDCl$_3$) δ ppm 2.10 (s, 3H), 2.37 (s, 3H), 4.72 (d, J=5.4 Hz, 2H), 6.07 (bs, 1H), 6.55 (bs, 1H), 7.18 (t, J=7.0 Hz, 1H), 7.34 (d, J=7.5 Hz, 1H), 7.48 (d, J=8.6 Hz, 2H), 7.58-7.65 (m 3H), 8.58 (d, J=3.2 Hz, 1H); MS (ESI) m/z 374.7 (M+1)$^+$.

Example 58

N⁴-(3,4-difluorophenyl)-5,6-dimethyl-N²-(pyridin-2-ylmethyl)pyrimidine-2,4-diamine The titled compound was synthesized according to the procedure described for preparation of N⁴-cyclopentyl-5,6-dimethyl-N²-(pyridin-2-ylmethyl)pyrimidine-2,4-diamine (Example 29) using (3,4-difluorophenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a light-yellow solid. $^1$H NMR (300 MHz, CDCl$_3$) δ ppm 2.05 (s, 3H), 2.32 (s, 3H), 4.70 (d, J=5.5 Hz, 2H), 5.87 (bs, 1H), 6.32 (bs, 1H), 6.95-7.05 (m, 2H), 7.16 (t, J=7.0 Hz, 1H), 7.32 (d, J=8.1 Hz, 1H), 7.57-7.66 (m, 2H), 8.58 (d, J=3.6 Hz, 1H); MS (ESI) m/z 342.7 (M+1)$^+$.

Example 59

5,6-dimethyl-N²-(pyridin-2-ylmethyl)-N⁴-[2-(trifluoromethoxy)phenyl]pyrimidine-2,4-diamine The titled compound was synthesized according to the procedure described for preparation of N⁴-cyclopentyl-5,6-dimethyl-N²-(pyridin-2-ylmethyl)pyrimidine-2,4-diamine (Example 29) using [2-(trifluoromethoxy)phenyl]amine instead of cyclopentanamine. The crude material was purified by column chromatography eluting with mixture of chloroform/ethanol/20% water solution of ammonia (200:10:1), and then the final product was washed with diethyl ether to afford the titled compound as a light-yellow solid. $^1$H NMR (300 MHz, CDCl$_3$) δ ppm 1.09 (s, 3H), 2.35 (s, 3H), 4.74 (d, J=5.5 Hz, 2H), 6.81 (s, 1H), 6.98 (t, J=7.8 Hz, 1H), 7.16 (t, J=7.0 Hz, 2H), 7.23 (d, J=7.3 Hz, 1H), 7.36 (d, J=7.8 Hz, 1H), 7.62 (t, J=7.3 Hz, 1H), 8.43 (d, J=7.5 Hz, 1H), 8.59 (d, J=3.8 Hz, 1H); MS (ESI) m/z 390.5 (M+1)$^+$.

Example 60

N⁴-(2,5-difluorophenyl)-5,6-dimethyl-N²-(pyridin-2-ylmethyl)pyrimidine-2,4-diamine The titled compound was synthesized according to the procedure described for preparation of N⁴-cyclopentyl-5,6-dimethyl-N²-(pyridin-2-ylmethyl)pyrimidine-2,4-diamine (Example 29) using (2,5-difluorophenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a light-yellow solid. $^1$H NMR (300 MHz, CDCl$_3$) δ ppm 2.09 (s, 3H), 2.35 (s, 3H), 4.75 (d, J=4.8 Hz, 2H), 5.96 (bs, 1H), 6.656-6.62 (m, 1H), 6.67 (bs, 1H), 7.01 (m, 1H), 7.16 (t, J=5.4 Hz, 1H), 7.37 (d, J=7.8 Hz, 1H), 7.62 (t, J=7.8 Hz, 1H), 8.29 (bs, 1H), 8.59 (d, J=3.4 Hz, 1H); MS (ESI) m/z 342.7 (M+1)$^+$.

Example 61

N⁴-(1,3-benzodioxol-5-yl)-5,6-dimethyl-N²-(pyridin-2-ylmethyl)pyrimidine-2,4-diamine The titled compound was synthesized according to the procedure described for preparation of N⁴-cyclopentyl-5,6-dimethyl-N²-(pyridin-2-ylmethyl)pyrimidine-2,4-diamine (Example 29) using 1,3-benzodioxol-5-amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.04 (s, 3H), 2.32 (s, 3H), 4.69 (d, J=4.2 Hz, 2H), 5.76 (bs, 1H), 5.95 (s, 2H), 6.22 (s, 1H), 6.67-7.75 (m, 2H), 7.14 (t, J=6.4 Hz, 1H), 7.21 (s, 1H), 7.32 (d, J=7.8 Hz, 1H), 7.60 (t, J=7.6 Hz, 1H), 8.56 (d, J=3.6 Hz, 1H); MS (ESI) m/z 350.7 (M+1)$^+$.

Example 62

N$^4$-(4-chlorophenyl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using (4-chlorophenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.06 (s, 3H), 2.33 (s, 3H), 4.60 (d, J=3.0 Hz, 2H), 5.77 (bs, 1H), 6.30 (bs, 1H), 7.13-7.20 (m, 3H), 7.32 (d, J=6.8 Hz, 1H), 7.43 (d, J=7.8 Hz, 2H), 7.61 (t, J=7.6 Hz, 1H), 8.58 (d, J=3.4 Hz, 1H); MS (ESI) m/z 340.6 (M+1)$^+$.

Example 63

5,6-dimethyl-N$^4$-(4-methylphenyl)-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using p-toluidine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.06 (s, 3H), 2.31 (s, 3H), 2.33 (s, 3H), 4.71 (d, J=2.8 Hz, 2H), 5.75 (bs, 1H), 6.28 (s, 1H), 7.06 (d, J=7.3 Hz, 2H), 7.15 (t, J=6.8 Hz, 1H), 7.30-7.38 (m, 3H), 7.61 (t, J=7.4 Hz, 1H), 8.58 (d, J=4.0 Hz, 1H); MS (ESI) m/z 320.7 (M+1)$^+$.

Example 64

N$^4$-(3,5-difluorophenyl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using (3,5-difluorophenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.07 (s, 3H), 2.34 (s, 3H), 4.73 (d, J=3.1 Hz, 2H), 5.93 (bs, 1H), 6.39-6.49 (m, 2H), 7.13-7.22 (m, 3H), 7.34 (d, J=7.8 Hz, 1H), 7.63 (t, J=5.9 Hz, 1H), 8.59 (d, J=3.8 Hz, 1H); MS (ESI) m/z 342.7 (M+1)$^+$.

Example 65

N$^4$-(3-chlorophenyl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using (3-chlorophenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 2.03 (s, 3H), 2.20 (s, 3H), 4.51 (d, J=3.0 Hz, 2H), 6.91 (d, J=6.8 Hz, 1H), 7.02-7.15 (m, 2H), 7.20 (t, J=6.4 Hz, 1H), 7.26 (d, J=8.1 Hz, 1H), 7.55 (bs, 1H), 7.69 (t, J=7.9 Hz, 1H), 7.78 (s, 1H), 8.10 (s, 1H), 8.49 (d, J=3.8 Hz, 1H); MS (ESI) m/z 340.1 (M+1)$^+$.

Example 66

N$^4$-(2-chlorophenyl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using (2-chlorophenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.13 (s, 3H), 2.38 (s, 3H), 4.75 (d, J=2.8 Hz, 2H), 6.05 (bs, 1H), 6.94 (t, J=6.4 Hz, 1H), 7.06-7.20 (m, 3H), 7.36 (d, J=6.8 Hz, 2H), 7.62 (t, J=7.6 Hz, 1H), 8.40 (d, J=5.8 Hz, 1H), 8.60 (d, J=3.4 Hz, 1H); MS (ESI) m/z 340.6 (M+1)$_+$.

Example 67

5,6-dimethyl-N$^4$-(2-methylphenyl)-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using o-toluidine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.08 (s, 3H), 2.27 (s, 3H), 2.34 (s, 3H), 4.66 (d, J=3.2 Hz, 2H), 5.70 (bs, 1H), 6.14 (s, 1H), 7.01 (t, J=6.3 Hz, 1H), 7.13 (t, J=6.3 Hz, 2H), 7.18 (d, J=7.5 Hz, 1H), 7.24 (d, J=7.8 Hz, 1H), 7.58 (t, J=7.8 Hz, 1H), 7.84 (d, J=7.8 Hz, 1H), 8.54 (d, J=4.8 Hz, 1H); MS (ESI) m/z 320.7 (M+1)$^+$.

Example 68

N$^4$-(2,6-dimethylphenyl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using (2,6-dimethylphenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.09 (s, 3H), 2.14 (s, 6H), 2.31 (s, 3H), 4.40 (d, J=3.2 Hz, 2H), 5.52 (bs, 1H), 5.71 (s, 1H), 6.90 (bs, 1H), 7.04-7.14 (m, 4H), 7.46 (t, J=9.4 Hz, 1H), 8.45 (d, J=4.8 Hz, 1H); MS (ESI) m/z 335.0 (M+1)$^+$.

Example 69

5,6-dimethyl-N$^4$-(3-methylphenyl)-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using m-toluidine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.07 (s, 3H), 2.28 (s, 3H), 2.33 (s, 3H), 4.74 (d, J=3.0 Hz, 2H), 5.79 (bs, 1H), 6.31 (s, 1H), 6.84 (d, J=8.1 Hz, 1H), 7.10-7.17 (m, 2H), 7.30-7.40 (m, 3H), 7.60 (t, J=7.8 Hz, 1H), 8.57 (d, J=2.8 Hz, 1H); MS (ESI) m/z 320.7 (M+1)$^+$.

Example 70

N$^4$-(1,1-dioxidotetrahydrothiophen-3-yl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using (1,1-dioxidotetrahydro-3-thienyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 1.91 (s, 3H), 2.22 (m, 1H), 2.29 (s, 3H), 2.20-2.26 (m, 1H), 2.80-2.91 (m, 1H), 2.95 (bs, 1H), 3.05-3.15 (m, 1H), 3.18-3.24 (m, 1H), 4.69 (bs, 2H), 4.80-4.89 (m, 2H), 5.92 (bs, 1H), 7.17 (t, J=3.9 Hz, 1H), 7.34 (d, J=5.8 Hz, 1H), 7.64 (t, J=6.4 Hz, 1H), 8.57 (d, J=2.8 Hz, 1H); MS (ESI) m/z 348.8 (M+1)$^+$.

Example 71

N$^4$-(5-fluoro-2-methylphenyl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using (5-fluoro-2-methylphenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 2.03 (s, 3H), 2.11 (s, 3H), 2.17 (s, 3H), 4.39 (d, J=1.6 Hz, 2H), 7.77-7.88 (m, 2H), 7.09-7.20 (m, 3H), 7.34 (d, J=9.8 Hz, 1H), 7.45 (s, 1H), 7.64 (t, J=7.5 Hz, 1H), 8.43 (d, J=2.8 Hz, 1H); MS (ESI) m/z 338.8 (M+1)$^+$.

Example 72

N$^4$-(2-fluoro-6-methylphenyl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using (2-fluoro-6-methylphenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, methanol-d$_4$) δ ppm 2.07 (s, 3H), 2.11 (s, 3H), 2.23 (s, 3H), 4.29 (s, 2H), 6.88 (t, J=9.1 Hz, 1H), 6.97 (t, J=5.9 Hz, 2H), 7.13 (m, 1H), 7.26 (t, J=7.3 Hz, 1H), 7.61 (t, J=7.3 Hz, 1H), 8.34 (d, J=5.0 Hz, 1H); MS (ESI) m/z 338.8 (M+1)$^+$.

Example 73

N$^4$-(4,5-difluoro-2-methylphenyl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using (4,5-difluoro-2-methylphenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 2.02 (s, 3H), 2.06 (s, 3H), 2.16 (s, 3H), 4.34 (bs, 2H), 6.81 (bs, 1H), 7.07-7.41 (m, 4H), 7.56 (bs, 1H), 7.63 (d, J=7.3 Hz, 1H), 8.42 (d, J=4.2 Hz, 1H); MS (ESI) m/z 356.6 (M+1)$^+$.

Example 74

5,6-dimethyl-N$^4$-(1-methyl-1H-pyrazol-5-yl)-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using 1-methyl-1H-pyrazol-5-amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, methanol-d$_4$) δ ppm 2.09 (s, 3H), 2.27 (s, 3H), 3.38 (s, 3H), 4.42 (s, 2H), 5.98 (s, 1H), 7.14 (d, J=7.5 Hz, 1H), 7.24 (t, J=6.7 Hz, 1H), 7.38 (s, 1H), 7.70 (t, J=7.0 Hz, 1H), 8.43 (d, J=5.2 Hz, 1H); MS (ESI) m/z 310.2 (M+1)$^+$.

Example 75

N$^4$-(4-fluoro-2-methylphenyl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using (4-fluoro-2-methylphenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 2.01 (s, 3H), 2.07 (s, 3H), 2.15 (s, 3H), 4.30 (bs, 2H), 6.68 (bs, 1H), 6.84-6.89 (m, 1H), 6.98-7.10 (m, 2H), 7.17 (t, J=7.3 Hz, 2H), 7.57-7.67 (m, 2H), 8.43 (d, J=4.2 Hz, 1H); MS (ESI) m/z 338.8 (M+1)$^+$.

Example 76

N$^4$-(3-fluoro-2-methylphenyl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using (3-fluoro-2-methylphenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 1.94 (s, 3H), 2.06 (s, 3H), 2.14 (s, 3H), 4.32 (bs, 2H), 6.76 (bs, 1H), 6.86-6.95 (m, 1H), 7.01-7.13 (m, 3H), 7.17 (t, J=6.4 Hz, 1H), 7.63 (t, J=8.4 Hz, 1H), 7.75 (s, 1H), 8.43 (d, J=4.2 Hz, 1H); MS (ESI) m/z 338.2 (M+1)$^+$.

Example 77

N$^4$-cyclohexyl-N$^4$,5,6-trimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using N-methylcyclohexanamine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 1.09-1.31 (m, 3H), 1.39-1.52 (m, 2H), 1.59-1.80 (m, 5H), 2.02 (s, 3H), 2.27 (s, 3H), 2.73 (s, 3H), 3.49-3.59 (m, 1H), 4.71 (d, J=6.2, 2H), 5.54 (bs, 1H), 7.11-7.15 (m, 1H), 7.35 (d, J=8.3, 1H), 7.57-7.62 (m, 1H), 8.52-8.55 (m, 1H); MS (ESI) m/z 326.2 (M+1)$^+$.

Example 78

N$^4$-(3,3-difluorocyclopentyl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using 3,3-difluorocyclopentylamine hydrochloride instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, methanol-d$_4$) δ ppm 1.73-2.27 (m, 9H), 2.36 (s, 3H), 3.30-3.34 (m, 2H), 4.30-4.40 (m, 1H), 7.73 (t, J=6.4, 1H), 7.84 (d, J=8.1, 1H), 8.28 (t, J=6.7, 1H), 8.70 (d, J=5.1, 1H); MS (ESI) m/z 334 (M+1)$^+$.

Example 79 trans-4-({5,6-dimethyl-2-[(pyridin-2-ylmethyl)amino]pyrimidin-4-yl}amino)cyclohexanol The titled compound was synthesized according to the procedure described for preparation of N$^4$-cyclopentyl-5,6-dimethyl-N$^2$-(pyridin-2-ylmethyl)pyrimidine-2,4-diamine (Example 29) using trans-4-aminocyclohexanol instead of cyclopentanamine. The crude material was purified by crystallization from ethanol to afford the titled compound as a hydrochloride salt as a white solid. $^1$H NMR (300 MHz, methanol-d$_4$) δ ppm 1.18-1.26 (m, 2H), 1.32-1.44 (m, 2H), 1.67 (d, J=11.28 Hz, 2H), 1.80-1.99 (m, 5H), 2.33 (s, 3H), 3.45-3.55 (m, 1H), 3.75-3.83 (m, 1H), 4.72 (s, 2H), 7.33 (bs, 1H), 7.44 (d, J=7.79 Hz, 1H), 7.83 (t, J=7.12 Hz, 1H), 8.53 (d, J=4.30 Hz, 1H); MS (ESI) m/z 328.3 (M+1)$^+$.

Example 80

N$^4$-(3,3-difluorocyclohexyl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using (3,3-difluorocyclohexyl)amine hydrochloride instead of cyclopentanamine. The crude material was purified by HPLC (column: YMC-PACK ODS-AQ C18, 250 mm×20 mm, 10 μm; gradient: 20-50% acetonitrile in 0.02% trifluoroacetic acid/water over fifteen minutes; 50-100% acetonitrile in 0.02% trifluoroacetic acid/water over five minutes; flow rate: 25 mL/min; temperature: 25° C.) to afford the titled compound as a trifluoroacetate salt as a white solid. $^1$H NMR (300 MHz, DMSO-d$_6$) δ ppm 1.80-2.11 (m, 14H), 3.75 (bs, 1H), 4.40-4.49 (m, 2H), 5.31 (bs, 2H), 7.20-7.28 (m, 1H), 7.56 (bs, 1H), 7.73 (bs, 1H), 8.65 (bs, 1H); MS (ESI) m/z 348.1 (M+1)$^+$.

Example 81

5,6-dimethyl-N$^4$-(1-methylpiperidin-4-yl)-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using 1-methylpiperidin-4-amine instead of cyclopentanamine. The crude material was purified by column chromatography eluting with mixture of chloroform/ethanol/20% water solution of ammonia (200:10:1), and then the final product was washed with diethyl ether to afford the titled compound as a light-grey solid. $^1$H NMR (300 MHz, DMSO-d$_6$) δ ppm 1.68 (bs, 4H) 1.85 (s, 3H) 2.13 (bs, 3H) 2.57 (bs, 3H) 2.66 (bs, 2H) 3.13 (d, J=11.82 Hz, 2H) 3.81 (bs, 1H) 4.52 (d, J=5.91 Hz, 2H) 6.52 (s, 1H) 7.15-7.22 (m, 1H) 7.27 (d, J=7.79 Hz, 1H) 7.70 (d, J=7.66 Hz, 1H) 8.48 (d, J=4.03 Hz, 1H); MS (ESI) m/z 327.5 (M+1)$^+$.

Example 82 tert-butyl 4-({5,6-dimethyl-2-[(pyridin-2-ylmethyl)amino]pyrimidin-4-yl}amino)piperidine-1-carboxylate The titled compound was synthesized according to the procedure described for preparation of N$^4$-cyclopentyl-5,6- dimethyl-N²-(pyridin-2-ylmethyl)pyrimidine-2,4-diamine (Example 29) using 1-methylpiperidin-4-amine instead of cyclopentanamine. The crude material was purified by column chromatography eluting with mixture of chloroform/ethanol/20% water solution of ammonia (200:10:1), and then the final product was washed with diethyl ether to afford the titled compound as a light-grey solid. $^1$H NMR (300 MHz, DMSO-d$_6$) δ ppm 1.20-1.30 (m, 2H), 1.39 (s, 9H), 1.50-1.60 (m, 2H), 1.80 (s, 3H), 2.06 (s, 3H), 2.60-2.68 (m, 2H), 3.76-3.90 (m, 3H), 4.48 (d, J=5.4 Hz, 2H), 5.81 (d, J=5.4 Hz, 1H), 6.71 (bs, 1H), 7.18 (t, J=4.4 Hz, 1H), 7.22 (d, J=5.4 Hz, 1H), 7.67 (t, J=8.1 Hz, 1H), 8.45 (d, J=4.4 Hz, 1H); MS (ESI) m/z 413.2 (M+1)$^+$.

Example 83

5,6-dimethyl-N⁴-(piperidin-4-yl)-N²-(pyridin-2-ylmethyl)pyrimidine-2,4-diamine tert-Butyl 4-({5,6-dimethyl-2-[(pyridin-2-ylmethyl)amino]pyrimidin-4-yl}amino)piperidine-1-carboxylate (100 mg, 0.24 mmol, Example 82) was suspended in a solution of 3 M hydrogen chloride in dioxane (10 mL). The reaction mixture was stirred at ambient temperature overnight, and then the solvent was removed under reduced pressure. The residue was purified by flash chromatography on silica gel eluted with mixture of chloroform/ethanol/20% water solution of ammonia (200:10:1) to afford the titled compound as a light-grey solid. $^1$H NMR (300 MHz, DMSO-d$_6$) δ ppm 1.25-1.32 (m, 2H), 1.84-1.92 (m, 5H), 2.25 (s, 3H), 12.43 (bs, 1H), 2.60-2.65 (m, 2H), 3.02-3.08 (m, 2H), 3.985-3.94 (m, 1H), 4.25 (d, J=8.3 Hz, 2H), 4.68 (d, J=5.3 Hz, 2H), 5.59 (bs, 1H), 7.12 (t, J=4.6 Hz, 1H), 7.36 (d, J=8.1 Hz, 1H), 7.60 (t, J=6.4 Hz, 1H), 8.54 (d, J=4.2 Hz, 1H); MS (ESI) m/z 313.2 (M+1)$^+$.

Example 84

N⁴-(2,6-diisopropylphenyl)-5,6-dimethyl-N²-(pyridin-2-ylmethyl)pyrimidine-2,4-diamine The titled compound was synthesized according to the procedure described for preparation of N⁴-cyclopentyl-5,6-dimethyl-N²-(pyridin-2-ylmethyl)pyrimidine-2,4-diamine (Example 29) using (2,6-diisopropylphenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 1.13 (d, J=32.78 Hz, 12H), 2.12 (s, 3H), 2.31 (s, 3H), 3.00-3.12 (m, 2H), 4.40 (d, J=5.10 Hz, 2H). 5.40 (s, 1H), 5.65 (s, 1H), 6.85 (s, 1H), 7.04 (bs, 1H), 7.19 (d, J=7.52 Hz, 2H), 7.20-7.30 (m, 1H), 7.42 (t, J=7.52 Hz, 1H), 8.43 (d, J=4.03 Hz, 1H); MS (ESI) m/z 390.5 (M+1)$^+$.

Example 85

3-({5,6-dimethyl-2-[(pyridin-2-ylmethyl)amino]pyrimidin-4-yl}amino)cyclohexanol

The titled compound was synthesized according to the procedure described for preparation of N⁴-cyclopentyl-5,6-dimethyl-N²-(pyridin-2-ylmethyl)pyrimidine-2,4-diamine (Example 29) using 3-aminocyclohexanol instead of cyclopentanamine. The crude material was purified by crystallization from ethanol to afford to afford the titled compound as a hydrochloride salt as a white solid. $^1$H NMR (300 MHz, methanol-d$_4$) δ ppm 1.35-1.65 (m, 11H), 2.33 (s, 3H), 3.90-4.15 (m, 2H), 4.80-4.95 (m, 2H), 7.68-7.75 (m, 2H), 8.20-8.26 (m, 1H), 8.66 (d, J=11.15 Hz, 1H); MS (ESI) m/z 328.8 (M+1)$^+$.

Example 86

N⁴-cyclohexyl-5,6-dimethyl-N²-[(5-methylpyridin-2-yl)methyl]pyrimidine-2,4-diamine The titled compound was synthesized according to the general procedure described for preparation of N⁴-cyclohexyl-5,6-dimethyl-N²-(pyridin-2-ylmethyl)pyrimidine-2,4-diamine (Example 1) using [(5-methylpyridin-2-yl)methyl]amine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 0.97-1.33 (m, 5H), 1.51-1.69 (m, 5H), 1.87 (s, 3H), 2.24 (d, J=6.0 Hz, 6H), 3.73 (s, 1H), 4.57 (d, J=5.6 Hz, 2H), 7.20 (d, J=7.79 Hz, 1H), 7.56 (d, J=8.06 Hz, 2H), 8.06 (t, J=5.6 Hz, 1H), 8.33 (s, 1H), 12.90 (bs, 1H); MS (ESI) m/z 326.1 (M+1)$^+$.

Example 87

N⁴-cyclohexyl-5,6-dimethyl-N²-[1-(pyridin-2-yl)ethyl]pyrimidine-2,4-diamine

The titled compound was synthesized according to the procedure described for preparation of N⁴-cyclohexyl-5,6-dimethyl-N²-(pyridin-2-ylmethyl)pyrimidine-2,4-diamine (Example 1) using (1-pyridin-2-ylethyl)amine instead of (pyridin-2-ylmethyl)amine. The product was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 1.12-1.28 (m, 6H), 1.43-11.52 (m, 5H), 1.71-1.74 (m, 2H), 1.88 (s, 3H), 2.22 (s, 3H), 5.06-5.10 (m, 1H), 7.31 (t, J=8.06 Hz, 1H), 7.44 (d, J=8.06 Hz, 1H), 7.58 (d, J=8.06 Hz, 1H), 7.84 (t, J=8.06 Hz, 2H), 8.22 (d, J=2.0 Hz, 1H), 8.58 (d, J=2.0 Hz, 1H), 12.21 (bs, 1H); MS (ESI) m/z 326.5 (M+1)$^+$.

Example 88

N⁴-(2,4-difluorophenyl)-5,6-dimethyl-N²-(pyridin-2-ylmethyl)pyrimidine-2,4-diamine The titled compound was synthesized according to the procedure described for preparation of N⁴-cyclopentyl-5,6-dimethyl-N²-(pyridin-2-ylmethyl)pyrimidine-2,4-diamine (Example 29) using (2,4-difluorophenyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.09 (s, 3H), 2.37 (s, 3H), 4.71 (d, J=5.6 Hz, 2H), 6.06 (bs, 1H), 6.47 (bs, 1H), 7.75 (t, J=9.4 Hz, 1H), 7.85 (t, J=10.0 Hz, 1H), 7.17 (t, J=7.3 Hz, 1H), 7.33

(d, J=7.8 Hz, 1H), 7.62 (t, J=7.5 Hz, 1H), 8.12 (bs, 1H), 8.58 (d, J=2.8 Hz, 1H); MS (ESI) m/z 342.6 (M+1)$^+$.

Example 89

5-ethyl-$N^4$-(4-fluorophenyl)-6-methyl-$N^2$-(pyridin-2-ylmethyl)pyrimidine-2,4-diamine Step A 2-chloro-5-ethyl-N-(4-fluorophenyl)-6-methylpyrimidin-4-amine The titled compound was synthesized according to the procedure described for preparation of 2-chloro-N-cyclohexyl-5,6-dimethylpyrimidin-4-amine (Example 1, Step D) using 2,4-dichloro-5-ethyl-6-methylpyrimidine instead 2,4-dichloro-5,6-dimethylpyrimidine and 4-fluoroaniline instead of cyclohexylamine. The titled compound was obtained as a white solid. MS (ESI) m/z 266.7, 268.7 (M+1)$^+$.

Step B 5-ethyl-$N^4$-(4-fluorophenyl)-6-methyl-$N^2$-(pyridin-2-ylmethyl)pyrimidine-2,4-diamine The titled compound was synthesized according to the general procedure described for preparation of $N^4$-cyclohexyl-5,6-dimethyl-$N^2$-(pyridin-2-ylmethyl)pyrimidine-2,4-diamine (Example 1) using 2-chloro-5-ethyl-N-(4-fluorophenyl)-6-methylpyrimidin-4-amine (Step A) instead of 2-chloro-N-cyclohexyl-5,6-dimethylpyrimidin-4-amine. The product was purified by column chromatography eluting with mixture of chloroform/ethanol/20% water solution of ammonia (200:10:1), and then the final product was washed with diethyl ether to afford the titled compound as a light-grey solid. $^1$H NMR (300 MHz, methanol-$d_4$) δ ppm 1.09-1.20 (m, 3H), 2.25-2.35 (m, 3H), 2.52-2.62 (m, 2H), 4.57 (bs, 2H), 6.80-6.88 (m, 2H), 7.20-7.36 (m, 4H) 7.65-7.76 (m, 1H) 8.50 (bm, 1H); MS (ESI) m/z 338.8 (M+1)$^+$.

Example 90

$N^4$-(4,4-difluorocyclohexyl)-$N^2$-[(4-ethylpyridin-2-yl)methyl]-5,6-dimethylpyrimidine-2,4-diamine Step A 2-chloro-N-(4,4-difluorocyclohexyl)-5,6-dimethylpyrimidin-4-amine To the solution of 2,4-dichloro-5,6-dimethylpyrimidine (0.585 g, 3.304 mmol) in N,N-dimethylformamide (10 mL), (4,4-difluorocyclohexyl)amine hydrochloride (0.652 g, 3.800 mmol) and triethylamine (1.338 g, 13.218 mmol) were added, and reaction mixture was heated at 50° C. overnight. Volatiles were removed under reduced pressure, and the residue was poured into water (300 mL). The product was extracted with ether (3×50 mL), dried over sodium sulfate, filtered, and concentrated under reduced pressure. The residue was subjected to column chromatography on silica eluting with a mixture of hexane/ethyl acetate (gradient 4:1-2:1) to provide 621 mg (68%) of the titled compound as a white solid. $^1$H NMR (300 MHz, DMSO-$d_6$) δ ppm 1.18-1.24 (m, 1H), 1.60-1.72 (m, 2H), 1.80-2.10 (m, 8H) 2.21 (s, 3H), 4.00-4.10 (m, 1H), 6.73 (d, J=7.79 Hz, 1H); MS (ESI) m/z 318.6 (M+1)$^+$.

Step B $N^4$-(4,4-difluorocyclohexyl)-$N^2$-[(4-ethylpyridin-2-yl)methyl]-5,6-dimethylpyrimidine-2,4-diamine The titled compound was synthesized according to the general procedure described for preparation of $N^4$-cyclohexyl-5,6-dimethyl-$N^2$-(pyridin-2-ylmethyl)pyrimidine-2,4-diamine (Example 1) using [(4-ethylpyridin-2-yl)methyl]amine instead of (pyridin-2-ylmethyl)amine and 2-chloro-N-(4,4-difluorocyclohexyl)-5,6-dimethylpyrimidin-4-amine (Step A) instead of 2-chloro-N-cyclohexyl-5,6-dimethylpyrimidin-4-amine. The product was purified by crystallization from ethanol to afford the titled compound as the hydrochloride salt as a light-yellow solid. $^1$H NMR (300 MHz, DMSO-$d_6$) δ ppm 1.16 (t, J=7.59 Hz, 3H), 1.57-1.1.89 (m, 11H) 2.25 (s, 3H) 2.62 (m, 2H) 3.95 (s, 1H) 4.64 (d, J=5.12 Hz, 2H) 7.17 (d, J=5.12 Hz, 1H) 7.24 (s, 1H) 7.64 (d, J=6.40 Hz, 1H) 8.31 (s, 1H) 8.40 (d, J=4.94 Hz, 1H) 12.58 (bs, 1H); MS (ESI) m/z 375.9 (M+1)$^+$.

Example 91

5,6-dimethyl-$N^2$-(pyridin-2-ylmethyl)-$N^4$-(tetrahydrofuran-2-ylmethyl)pyrimidine-2,4-diamine The titled compound was synthesized according to the procedure described for preparation of $N^4$-cyclopentyl-5,6-dimethyl-$N^2$-(pyridin-2-ylmethyl)pyrimidine-2,4-diamine (Example 29) using (tetrahydrofuran-2-ylmethyl)amine instead of cyclopentanamine. The crude material was purified by HPLC (column: YMC-PACK ODS-AQ C18, 250 mm×20 mm, 10 μm; gradient: 20-50% acetonitrile in 0.02% trifluoroacetic acid/water over fifteen minutes; 50-100% acetonitrile in 0.02% trifluoroacetic acid/water over five minutes; flow rate: 25 mL/min; temperature: 25° C.) to afford the titled compound as a trifluoroacetate salt as a light-grey solid. $^1$H NMR (300 MHz, DMSO-$d_6$) δ ppm δ 1.34 (s, 1H), 1.59-1.78 (m, 3H), 1.88 (s, 3H), 2.25 (s, 3H), 3.23-3.29 (m, 2H), 3.46-3.50 (m, 1H), 3.64 (dd, $J_1$=13.84, $J_2$=7.12 Hz, 2H), 4.70 (m, 2H), 7.43 (m, 1H), 7.47 (d, J=7.79 Hz, 1H), 7.94 (t, J=7.12 Hz, 1H), 8.14 (d, J=5.10 Hz, 1H), 8.59 (d, J=4.30 Hz, 1H), 8.63 (t, J=5.37 Hz, 1H), 12.89 (bs, 1H); MS (ESI) m/z 314.1 (M+1)$^+$.

Example 92

$N^4$-(cyclohexylmethyl)-5,6-dimethyl-$N^2$-(pyridin-2-ylmethyl)pyrimidine-2,4-diamine The titled compound was synthesized according to the procedure described for preparation of $N^4$-cyclopentyl-5,6-dimethyl-$N^2$-(pyridin-2-ylmethyl)pyrimidine-2,4-diamine (Example 29) using 1-cyclohexylmethanamine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-$d_6$) δ ppm 0.66-0.73 (m, 2H), 1.00 (bs, 3H), 1.35 (bs, 1H), 1.42-1.58 (m, 5H), 1.86 (s, 3H), 2.18 (s, 3H), 3.06 (bs, 2H), 4.58 (bs, 2H), 7.26 (bs, 2H), 7.40-7.46 (m, 1H), 7.68-7.74 (m, 1H), 8.49 (bs, 1H); MS (ESI) m/z 326.5 (M+1)$^+$.

Example 93

5,6-dimethyl-N$^4$-(pyridin-3-yl)-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using pyridin-3-amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.11 (s, 3H), 2.35 (s, 3H), 4.71 (d, J=3.0 Hz, 2H), 5.97 (bs, 1H), 6.41 (bs, 1H), 7.13-7.20 (m, 2H), 7.31 (d, J=7.4 Hz, 1H), 7.62 (t, J=7.6 Hz, 1H), 8.05 (d, J=4.0 Hz, 1H), 8.26 (bs, 1H), 8.56-8.63 (m, 2H); MS (ESI) m/z 307.9 (M+1)$^+$.

Example 94

5,6-dimethyl-N$^2$-(pyridin-2-ylmethyl)-N$^4$-(1,3,4-thiadiazol-2-yl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using 1,3,4-thiadiazol-2-amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, DMSO-d$_6$) δ ppm 2.10 (s, 3H), 2.25 (s, 3H), 4.68 (d, J=2.0 Hz, 2H), 7.18-7.51 (m, 3H), 7.70 (t, J=7.8 Hz, 1H), 8.50 (s, 1H), 9.01 (s, 1H), 10.93 (bs, 1H); MS (ESI) m/z 314.1 (M+1)$^+$.

Example 95

5,6-dimethyl-N$^4$-(1,2-oxazol-3-yl)-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using isoxazol-3-amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.08 (s, 3H), 2.35 (s, 3H), 4.74 (d, J=2.8 Hz, 2H), 5.97 (bs, 1H), 6.98 (s, 1H), 7.17 (t, J=6.4 Hz, 1H), 7.31-7.44 (m, 2H), 7.63 (t, J=6.5 Hz, 1H), 8.17 (s, 1H), 8.56 (d, J=4.6 Hz, 1H); MS (ESI) m/z 297.8 (M+1)$^+$.

Example 96

5,6-dimethyl-N$^4$-(5-methyl-1,2-oxazol-3-yl)-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using 5-methylisoxazol-3-amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 2.06 (s, 3H), 2.35 (s, 3H), 4.75 (d, J=2.8 Hz, 2H), 5.92 (bs, 1H), 6.54 (s, 1H), 7.18 (m, 1H), 7.36 (d, J=7.8 Hz, 1H), 7.64 (t, J=7.5 Hz, 1H), 8.59 (d, J=4.0 Hz, 1H); MS (ESI) m/z 311.5 (M+1)$^+$.

Example 97

N$^4$-(4-fluorobenzyl)-5,6-dimethyl-N$^2$-(pyridin-2-ylmethyl)pyrimidine-2,4-diamine The titled compound was synthesized according to the procedure described for preparation of N$^4$-cyclopentyl-5,6-dimethyl-N$^2$-(pyridin-2-ylmethyl)pyrimidine-2,4-diamine (Example 29) using (4-fluorobenzyl)amine instead of cyclopentanamine. The crude material was purified by column chromatography eluting with mixture of chloroform/ethanol/20% water solution of ammonia (200:10:1), and then the final product was washed with diethyl ether to afford the titled compound as a white solid. $^1$H NMR (300 MHz, CDCl$_3$) δ ppm 1.92 (s, 3H), 2.27 (s, 3H), 4.56 (d, J=3.8 Hz, 2H), 4.72 (d, J=2.8 Hz, 2H), 4.78 (bs, 1H), 5.70 (bs, 1H), 6.94 (t, J=8.6 Hz, 2H), 7.13 (d, J=7.8 Hz, 1H), 7.20 (t, J=7.5 Hz, 2H), 7.29 (bs, 1H), 7.57 (t, J=7.5 Hz, 1H), 8.57 (d, J=3.2 Hz, 1H); MS (ESI) m/z 338.8 (M+1)$^+$.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

What is claimed is:
1. A compound having formula (I), or a pharmaceutically acceptable salt thereof,

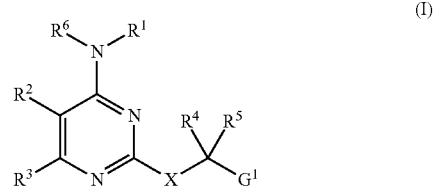

wherein:
R$^1$ is cyclohexyl optionally substituted with 1, 2, 3, or 4 substituents selected from the group consisting of C$_1$-C$_{10}$-alkyl, C$_2$-C$_{10}$-alkenyl, C$_2$-C$_{10}$-alkynyl, C$_1$-C$_{10}$-haloalkyl, C$_2$-C$_{10}$-haloalkenyl, C$_2$-C$_{10}$-haloalkynyl, halogen, oxo, cyano, hydroxy, —O—C$_1$-C$_6$-alkyl, O—C$_1$-C$_6$-haloalkyl, —C$_1$-C$_3$-alkylene-O—H, C$_1$-C$_3$-alkylene-O—C$_1$-C$_6$-alkyl, —C$_1$-C$_3$-alkylene-O—C$_1$-C$_6$-haloalkyl, —C$_1$-C$_3$-alkylene-NH$_2$, —NH$_2$, —C(O)O—C$_1$-C$_6$-alkyl, —N(R$^{b1}$)C(O)R$^{b1}$, —CON(R$^{a1}$)(R$^{b1}$), —C(O)R$^{b1}$, —OC(O)R$^{b1}$, —OS(O)$_2$N(R$^{a1}$)(R$^{b1}$), —CO$_2$H, —CO$_2$R$^{b1}$, —N(R$^{b1}$)C(O)N(R$^{b1}$)$_2$, —S—R$^{b1}$, —S(O)$_2$R$^{b1}$, —S(O)R$^{b1}$, —SO$_2$N(R$^{a1}$)(R$^{b1}$), —N(R$^{a1}$)(R$^{a1}$), —N(R$^{b1}$)S(O)$_2$R$^{b1}$, —N(R$^{b1}$)C (O)O($R^{b1}$), —N($R^{b1}$)S(O)$_2$O($R^{b1}$), -$L^{1a}$-O—$R^{b1}$, -$L^{1a}$-CN, -$L^{1a}$-N($R^{b1}$)C(O)$R^{b1}$, -$L^{1a}$-CON($R^{a1}$)($R^{1b}$), -$L^{1a}$-C(O)$R^{b1}$, $L^{1a}$-OC(O)$R^{b1}$, -$L^{1a}$-CO$_2$H, -$L^{1a}$-CO$_2R^{b1}$, -$L^{1a}$-N($R^{b1}$)C(O)N($R^{b1}$)$_2$, $L^{1a}$-S—$R^{b1}$, -$L^{1a}$-S(O)$_2R^{b1}$, -$L^{1a}$-S(O)$R^{b1}$, -$L^{1a}$-SO$_2$—N($R^{a1}$)$R^{b1}$), -$L^{1a}$-($R^{a1}$) ($R^{b1}$), -$L^{1a}$-N($R^{b1}$)S(O)$_2R^{b1}$, and -$L^{1a}$-N($R^{b1}$)C(O)O ($R^{b1}$);

$R^2$ is methyl or ethyl;

$R^3$ is methyl or ethyl;

$R^4$ and $R^5$ are independently selected from the group consisting of hydrogen, $C_1$-$C_6$-alkyl, and $C_1$-$C_6$-haloalkyl;

$R^6$ is selected from the group consisting of hydrogen, $C_1$-$C_6$-alkyl, and $C_1$-$C_6$-haloalkyl;

$G^1$ is optionally substituted with 1, 2, 3, 4, or 5 substituents selected from the group consisting of halogen, $C_1$-$C_6$-alkyl, $C_1$-$C_6$-haloalkyl, —O—$R^f$, —CN, —N($R^f$)C(O)$R^f$, —CON($R^e$)($R^f$), —C(O)$R^f$, —OC(O)$R^f$, —CO$_2$H, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, —N($R^f$)C(O)O($R^f$), -$L^3$-O—$R^f$, -$L^3$-CN, -$L^3$-N($R^f$)C(O)$R^f$, -$L^3$-CON($R^e$)($R^f$), -$L^3$-C(O)$R^f$, -$L^3$-OC(O)$R^f$, -$L^3$-CO$_2$H, -$L^3$-CO$_2R^f$, -$L^3$-N($R^f$)C(O)N ($R^f$)$_2$, -$L^3$-S—$R^f$, -$L^3$-S(O)$_2R^f$, -$L^3$-S(O)$R^f$, -$L^3$-SO$_2$N ($R^e$)($R^f$), -L-N($R^e$)($R^f$), -$L^3$-N($R^f$)S(O)$_2R^f$, and -$L^3$-N ($R^f$)C(O)O($R^f$);

X is selected from O or NR;

$R^a$, at each occurrence, is each independently hydrogen, $C_1$-$C_6$-alkyl, $C_1$-$C_6$-haloalkyl, or $C_3$-$C_8$-cycloalkyl, wherein the $C_3$-$C_8$-cycloalkyl is optionally substituted with 1, 2, 3, or 4 substituents selected from the group consisting of halogen, oxo, $C_1$-$C_3$alkyl, and $C_1$-$C_3$-haloalkyl;

$R^{a1}$, at each occurrence, is each independently hydrogen, $C_1$-$C_6$-alkyl, $C_1$-$C_6$-haloalkyl, or $C_3$-$C_8$-cycloalkyl, wherein the $C_3$-$C_8$-cycloalkyl is optionally substituted with 1, 2, 3, or 4 substituents selected from the group consisting of halogen, oxo, $C_1$-$C_3$alkyl, and $C_1$-$C_3$-haloalkyl;

$R^b$ is each independently hydrogen, $C_1$-$C_6$-alkyl, or $C_1$-$C_6$-haloalkyl;

$R^{b1}$ is each independently hydrogen, $C_1$-$C_6$-alkyl, or $C_1$-$C_6$-haloalkyl;

$R^e$, at each occurrence, is each independently hydrogen, $C_1$-$C_6$-alkyl, $C_1$-$C_6$-haloalkyl, or $C_3$-$C_8$-cycloalkyl, wherein the $C_3$-$C_8$-cycloalkyl is optionally substituted with 1, 2, 3, or 4 substituents selected from the group consisting of halogen, oxo, $C_1$-$C_6$-alkyl, and $C_1$-$C_3$-haloalkyl;

$R^f$ is each independently hydrogen, $C_1$-$C_6$-alkyl, or $C_1$-$C_6$-haloalkyl;

$R^g$ is hydrogen or $C_1$-alkyl;

$L^1$, at each occurrence, is each independently $C_1$-$C_6$-alkylene or $C_3$-$C_8$-cycloalkyl, wherein $L^1$ is each optionally substituted with 1, 2, 3, or 4 halogen or 1 or 2 hydroxy;

$L^{1a}$, at each occurrence, is each independently $C_1$-$C_6$-alkylene or $C_3$-$C_8$cycloalkyl, wherein $L^{1a}$ is each optionally substituted with 1, 2, 3, or 4 halogen or 1 or 2 hydroxy; and $L^3$, at each occurrence, is each independently $C_1$-$C_6$-alkylene or $C_3$-$C_8$-cycloalkyl, wherein $L^3$ is each optionally substituted with 1, 2, 3, or 4 halogen.

2. The compound of claim 1, wherein X is O.

3. The compound of claim 1, wherein X is $NR^g$.

4. The compound of claim 1, wherein $R^2$ and $R^3$ are each methyl; $R^4$, $R^5$ and $R^6$ are each hydrogen; and X is $NR^g$, wherein $R^g$ is hydrogen.

5. A compound selected from the group consisting of:
$N^4$-cyclohexyl-5,6-dimethyl-$N^2$-(pyridin-2-ylmethyl)pyrimidine-2,4-diamine;
$N^2$-benzyl-$N^4$-cyclohexyl-5,6-dimethylpyrimidine-2,4-diamine;
$N^4$-cyclohexyl-5,6-dimethyl-$N^2$-(pyridin-3-ylmethyl)pyrimidine-2,4-diamine;
2-({[4-(cyclohexylamino)-5,6-dimethylpyrimidin-2-yl]amino}methyl)-6-methylpyridin-3-ol;
$N^4$-cyclohexyl-$N^2$-(4-methoxybenzyl)-5,6-dimethylpyrimidine-2,4-diamine;
$N^4$-cyclohexyl-$N^2$-(4-fluorobenzyl)-5,6-dimethylpyrimidine-2,4-diamine;
$N^4$-cyclohexyl-5,6-dimethyl-$N^2$-[4-(trifluoromethoxy)benzyl]pyrimidine-2,4-diamine;
$N^4$-cyclohexyl-$N^2$-(4-isopropylbenzyl)-5,6-dimethylpyrimidine-2,4-diamine;
$N^4$-cyclohexyl-5,6-dimethyl-$N^2$-[4-(trifluoromethyl)benzyl]pyrimidine-2,4-diamine;
$N^4$-cyclohexyl-$N^2$-(3-fluorobenzyl)-5,6-dimethylpyrimidine-2,4-diamine;
$N^4$-cyclohexyl-5,6-dimethyl-$N^2$-(1H-pyrazol-5-ylmethyl)pyrimidine-2,4-diamine;
$N^4$-cyclohexyl-5,6-dimethyl-$N^2$-[(1R)-1-phenylethyl]pyrimidine-2,4-diamine;
$N^4$-cyclohexyl-5,6-dimethyl-$N^2$-[(1S)-1-phenylethyl]pyrimidine-2,4-diamine;
$N^4$-cyclohexyl-5,6-dimethyl-$N^2$-[(4-methylpyridin-2-yl)methyl]pyrimidine-2,4-diamine;
$N^4$-cyclohexyl-$N^2$-[(4-methoxypyridin-2-yl)methyl]-5,6-dimethylpyrimidine-2,4-diamine;
$N^4$-cyclohexyl-5,6-dimethyl-$N^2$-[(6-methylpyridin-2-yl)methyl]pyrimidine-2,4-diamine;
$N^4$-cyclohexyl-5,6-dimethyl-$N^2$-{[5-(trifluoromethyl)pyridin-2-yl]methyl}pyrimidine-2,4-diamine;
$N^2$-[(4-tert-butylpyridin-2-yl)methyl]-$N^4$-cyclohexyl-5,6-dimethylpyrimidine-2,4-diamine;
$N^4$-cyclohexyl-5,6-dimethyl-$N^2$-(2-thienylmethyl)pyrimidine-2,4-diamine;
$N^4$-cyclohexyl-$N^2$-[(3,5-dimethyl-1,2-oxazol-4-yl)methyl]-5,6-dimethylpyrimidine-2,4-diamine;
$N^4$-cyclohexyl-5,6-dimethyl-$N^2$-[(1-methyl-1H-imidazol-4-yl)methyl]pyrimidine-2,4-diamine;
$N^4$-cyclohexyl-$N^2$-(3-methoxybenzyl)-5,6-dimethylpyrimidine-2,4-diamine;
$N^4$-cyclohexyl-5,6-dimethyl-$N^2$-[(3-methylpyridin-2-yl)methyl]pyrimidine-2,4-diamine;
$N^2$-[(4-chloropyridin-2-yl)methyl]-$N^4$-cyclohexyl-5,6-dimethylpyrimidine-2,4-diamine;
$N^4$-(4,4-difluorocyclohexyl)-5,6-dimethyl-$N^2$-[(4-methylpyridin-2-yl)methyl]pyrimidine-2,4-diamine;
$N^4$-cyclopentyl-5,6-dimethyl-$N^2$-(pyridin-2-ylmethyl)pyrimidine-2,4-diamine;
5,6-dimethyl-$N^2$-(pyridin-2-ylmethyl)-$N^4$-(tetrahydro-2H-pyran-4-yl)pyrimidine-2,4-diamine;
5,6-dimethyl-$N^2$-(pyridin-2-ylmethyl)-$N^4$-[4-(trifluoromethyl)cyclohexyl]pyrimidine-2,4-diamine;
$N^4$-(4,4-difluorocyclohexyl)-5,6-dimethyl-$N^2$-(pyridin-2-ylmethyl)pyrimidine-2,4-diamine;
$N^4$-(2,3-dihydro-1H-inden-1-yl)-5,6-dimethyl-$N^2$-(pyridin-2-ylmethyl)pyrimidine-2,4-diamine;
3-({5,6-dimethyl-2-[(pyridin-2-ylmethyl)amino]pyrimidin-4-yl}amino)cyclopentanol;

5,6-dimethyl-N²-(pyridin-2-ylmethyl)-N⁴-(1,2,3,4-tetrahydronaphthalen-1-yl)pyrimidine-2,4-diamine;
N⁴-(3,4-dihydro-2H-chromen-4-yl)-5,6-dimethyl-N²-(pyridin-2-ylmethyl)pyrimidine-2,4-diamine;
cis-4-({5,6-dimethyl-2-[(pyridin-2-ylmethyl)amino]pyrimidin-4-yl}amino)-1-methylcyclohexanol;
trans-4-({5,6-dimethyl-2-[(pyridin-2-ylmethyl)amino]pyrimidin-4-yl}amino)-1-methylcyclohexanol;
N⁴-(bicyclo[2.2.1]hept-2-yl)-5,6-dimethyl-N²-(pyridin-2-ylmethyl)pyrimidine-2,4-diamine;
5,6-dimethyl-N⁴-(2-methylcyclohexyl)-N²-(pyridin-2-ylmethyl)pyrimidine-2,4-diamine;
N⁴-(2,3-dimethylcyclohexyl)-5,6-dimethyl-N²-(pyridin-2-ylmethyl)pyrimidine-2,4-diamine;
2-({5,6-dimethyl-2-[(pyridin-2-ylmethyl)amino]pyrimidin-4-yl}amino)cyclohexanol;
[(1R,2S)-2-({5,6-dimethyl-2-[(pyridin-2-ylmethyl)amino]pyrimidin-4-yl}amino)cyclohexyl]methanol;
N⁴-(cyclopentylmethyl)-5,6-dimethyl-N²-(pyridin-2-ylmethyl)pyrimidine-2,4-diamine;
N⁴-cycloheptyl-5,6-dimethyl-N²-(pyridin-2-ylmethyl)pyrimidine-2,4-diamine;
N⁴-(2,3-dihydro-1H-inden-2-yl)-5,6-dimethyl-N²-(pyridin-2-ylmethyl)pyrimidine-2,4-diamine;
N⁴-cyclobutyl-5,6-dimethyl-N²-(pyridin-2-ylmethyl)pyrimidine-2,4-diamine;
5,6-dimethyl-N⁴-(pentan-3-yl)-N²-(pyridin-2-ylmethyl)pyrimidine-2,4-diamine;
N⁴-(3-fluorophenyl)-5,6-dimethyl-N²-(pyridin-2-ylmethyl)pyrimidine-2,4-diamine;
N⁴-(4-fluorophenyl)-5,6-dimethyl-N²-(pyridin-2-ylmethyl)pyrimidine-2,4-diamine;
N⁴-(2-fluorophenyl)-5,6-dimethyl-N²-(pyridin-2-ylmethyl)pyrimidine-2,4-diamine;
5,6-dimethyl-N⁴-phenyl-N²-(pyridin-2-ylmethyl)pyrimidine-2,4-diamine;
5,6-dimethyl-N²-(pyridin-2-ylmethyl)-N⁴-[3-(trifluoromethoxy)phenyl]pyrimidine-2,4-diamine;
5,6-dimethyl-N²-(pyridin-2-ylmethyl)-N⁴-[3-(trifluoromethyl)phenyl]pyrimidine-2,4-diamine;
N⁴-(2,6-difluorophenyl)-5,6-dimethyl-N²-(pyridin-2-ylmethyl)pyrimidine-2,4-diamine;
5,6-dimethyl-N²-(pyridin-2-ylmethyl)-N⁴-[4-(trifluoromethoxy)phenyl]pyrimidine-2,4-diamine;
5,6-dimethyl-N²-(pyridin-2-ylmethyl)-N⁴-[4-(trifluoromethyl)phenyl]pyrimidine-2,4-diamine;
N⁴-(3,4-difluorophenyl)-5,6-dimethyl-N²-(pyridin-2-ylmethyl)pyrimidine-2,4-diamine;
5,6-dimethyl-N²-(pyridin-2-ylmethyl)-N⁴-[2-(trifluoromethoxy)phenyl]pyrimidine-2,4-diamine;
N⁴-(2,5-difluorophenyl)-5,6-dimethyl-N²-(pyridin-2-ylmethyl)pyrimidine-2,4-diamine;
N⁴-(1,3-benzodioxol-5-yl)-5,6-dimethyl-N²-(pyridin-2-ylmethyl)pyrimidine-2,4-diamine;
N⁴-(4-chlorophenyl)-5,6-dimethyl-N²-(pyridin-2-ylmethyl)pyrimidine-2,4-diamine;
5,6-dimethyl-N⁴-(4-methylphenyl)-N²-(pyridin-2-ylmethyl)pyrimidine-2,4-diamine;
N⁴-(3,5-difluorophenyl)-5,6-dimethyl-N²-(pyridin-2-ylmethyl)pyrimidine-2,4-diamine;
N⁴-(3-chlorophenyl)-5,6-dimethyl-N²-(pyridin-2-ylmethyl)pyrimidine-2,4-diamine;
N⁴-(2-chlorophenyl)-5,6-dimethyl-N²-(pyridin-2-ylmethyl)pyrimidine-2,4-diamine;
5,6-dimethyl-N⁴-(2-methylphenyl)-N²-(pyridin-2-ylmethyl)pyrimidine-2,4-diamine;
N⁴-(2,6-dimethylphenyl)-5,6-dimethyl-N²-(pyridin-2-ylmethyl)pyrimidine-2,4-diamine;
5,6-dimethyl-N⁴-(3-methylphenyl)-N²-(pyridin-2-ylmethyl)pyrimidine-2,4-diamine;
N⁴-(1,1-dioxidotetrahydrothiophen-3-yl)-5,6-dimethyl-N²-(pyridin-2-ylmethyl)pyrimidine-2,4-diamine;
N⁴-(5-fluoro-2-methylphenyl)-5,6-dimethyl-N²-(pyridin-2-ylmethyl)pyrimidine-2,4-diamine;
N⁴-(2-fluoro-6-methylphenyl)-5,6-dimethyl-N²-(pyridin-2-ylmethyl)pyrimidine-2,4-diamine;
N⁴-(4,5-difluoro-2-methylphenyl)-5,6-dimethyl-N²-(pyridin-2-ylmethyl)pyrimidine-2,4-diamine;
5,6-dimethyl-N⁴-(1-methyl-1H-pyrazol-5-yl)-N²-(pyridin-2-ylmethyl)pyrimidine-2,4-diamine;
N⁴-(4-fluoro-2-methylphenyl)-5,6-dimethyl-N²-(pyridin-2-ylmethyl)pyrimidine-2,4-diamine;
N⁴-(3-fluoro-2-methylphenyl)-5,6-dimethyl-N²-(pyridin-2-ylmethyl)pyrimidine-2,4-diamine;
N⁴-cyclohexyl-N⁴,5,6-trimethyl-N²-(pyridin-2-ylmethyl)pyrimidine-2,4-diamine;
N⁴-(3,3-difluorocyclopentyl)-5,6-dimethyl-N²-(pyridin-2-ylmethyl)pyrimidine-2,4-diamine;
trans-4-({5,6-dimethyl-2-[(pyridin-2-ylmethyl)amino]pyrimidin-4-yl}amino)cyclohexanol;
N⁴-(3,3-difluorocyclohexyl)-5,6-dimethyl-N²-(pyridin-2-ylmethyl)pyrimidine-2,4-diamine;
5,6-dimethyl-N⁴-(1-methylpiperidin-4-yl)-N²-(pyridin-2-ylmethyl)pyrimidine-2,4-diamine;
tert-butyl 4-({5,6-dimethyl-2-[(pyridin-2-ylmethyl)amino]pyrimidin-4-yl}amino)piperidine-1-carboxylate;
5,6-dimethyl-N⁴-(piperidin-4-yl)-N²-(pyridin-2-ylmethyl)pyrimidine-2,4-diamine;
N⁴-(2,6-diisopropylphenyl)-5,6-dimethyl-N²-(pyridin-2-ylmethyl)pyrimidine-2,4-diamine;
3-({5,6-dimethyl-2-[(pyridin-2-ylmethyl)amino]pyrimidin-4-yl}amino)cyclohexanol;
N⁴-cyclohexyl-5,6-dimethyl-N²-[(5-methylpyridin-2-yl)methyl]pyrimidine-2,4-diamine;
N⁴-cyclohexyl-5,6-dimethyl-N²-[1-(pyridin-2-yl)ethyl]pyrimidine-2,4-diamine;
N⁴-(2,4-difluorophenyl)-5,6-dimethyl-N²-(pyridin-2-ylmethyl)pyrimidine-2,4-diamine;
5-ethyl-N⁴-(4-fluorophenyl)-6-methyl-N²-(pyridin-2-ylmethyl)pyrimidine-2,4-diamine;
N⁴-(4,4-difluorocyclohexyl)-N²-[(4-ethylpyridin-2-yl)methyl]-5,6-dimethylpyrimidine-2,4-diamine;
5,6-dimethyl-N²-(pyridin-2-ylmethyl)-N⁴-(tetrahydrofuran-2-ylmethyl)pyrimidine-2,4-diamine;
N⁴-(cyclohexylmethyl)-5,6-dimethyl-N²-(pyridin-2-ylmethyl)pyrimidine-2,4-diamine;
5,6-dimethyl-N⁴-(pyridin-3-yl)-N²-(pyridin-2-ylmethyl)pyrimidine-2,4-diamine;
5,6-dimethyl-N²-(pyridin-2-ylmethyl)-N⁴-(1,3,4-thiadiazol-2-yl)pyrimidine-2,4-diamine;
5,6-dimethyl-N⁴-(1,2-oxazol-3-yl)-N²-(pyridin-2-ylmethyl)pyrimidine-2,4-diamine;
5,6-dimethyl-N⁴-(5-methyl-1,2-oxazol-3-yl)-N²-(pyridin-2-ylmethyl)pyrimidine-2,4-diamine; and
N⁴-(4-fluorobenzyl)-5,6-dimethyl-N²-(pyridin-2-ylmethyl)pyrimidine-2,4-diamine.

6. A pharmaceutical composition comprising one or more compounds of claim 1 or pharmaceutically acceptable salts thereof; one or more excipients; and optionally one or more additional therapeutic agents.

7. A method for inhibiting replication of an respiratory syncytial virus, comprising exposing the virus to one or more compounds of claim 1 or pharmaceutically acceptable salts thereof, optionally in combination with one or more therapeutic agents.

8. The method of claim 7, wherein the respiratory syncytial virus is from a mutant of a respiratory syncytial virus.

* * * * *